United States Patent
Qiao et al.

(10) Patent No.: US 9,120,798 B2
(45) Date of Patent: Sep. 1, 2015

(54) AMINO-HETEROARYL 7-HYDROXY-SPIROPIPERIDINE INDOLINYL ANTAGONISTS OF P2Y1 RECEPTOR

(71) Applicant: Bristol-Myers Squibb Company, Princeton, NJ (US)

(72) Inventors: Jennifer X. Qiao, Princeton, NJ (US); Carol Hui Hu, New Hope, PA (US); Carl Thibeault, Mascouch (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/417,985

(22) PCT Filed: Jul. 29, 2013

(86) PCT No.: PCT/US2013/052446
§ 371 (c)(1),
(2) Date: Jan. 28, 2015

(87) PCT Pub. No.: WO2014/022253
PCT Pub. Date: Feb. 6, 2014

(65) Prior Publication Data
US 2015/0197521 A1  Jul. 16, 2015

Related U.S. Application Data

(60) Provisional application No. 61/678,190, filed on Aug. 1, 2012.

(51) Int. Cl.
*C07D 471/10* (2006.01)
*C07D 519/00* (2006.01)

(52) U.S. Cl.
CPC ............ *C07D 471/10* (2013.01); *C07D 519/00* (2013.01)

(58) Field of Classification Search
CPC ............................ C07D 471/10; C07D 519/00
See application file for complete search history.

(56) References Cited

U.S. PATENT DOCUMENTS 7,550,499 B2  6/2009  Tuerdi et al.
7,728,008 B2  6/2010  Qiao et al.

FOREIGN PATENT DOCUMENTS

WO  WO 2007/002637  1/2007
WO  WO 2008/048981  4/2008

OTHER PUBLICATIONS

Abbracchio, M.P. et al., "Characterization of the UDP-glucose receptor (re-named here the $P2Y_{14}$ receptor) adds diversity to the P2Y receptor family", Trends in Pharmacological Sciences, vol. 24, No. 2, pp. 52-55 (2003).

Abbracchio, M.P. et al., "Purinoceptors: Are There Families of P2X and P2Y Purinoceptors?", Pharmac. Ther., vol. 64, pp. 445-475 (1994).

Anbazhagan, M. et al., "Direct Conversion of Amidoximes to Amidines via Transfer Hydrogenation", Synthesis, No. 16, pp. 2467-2469 (2003).

Baurand, A. et al., "The $P2Y_1$ Receptor as a Target for New Antithrombotic Drugs: A Review of the $P2Y_1$ Antagonist MRS-2179", Cardiovascular Drug Reviews, vol. 21, No. 1, pp. 67-76 (2003).

Boeynaems, J.-M. et al., "Overview of P2Y Receptors as Therapeutic Targets", Drug Development Research, vol. 52, pp. 187-189 (2001).

Boger, D.L. et al., "Benzylic Hydroperoxide Rearrangement: Observations on a Viable and Convenient Alternative to the Baeyer-Villiger Rearrangement", J. Org. Chem., vol. 51, No. 26, pp. 5436-5439 (1986).

Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).

Bundgaard, H., ed., Design of Prodrugs, Elsevier Science Publishers B.V., publ. (1985).

Bundgaard, H., "Prodrugs as a means to improve the delivery of peptide drugs", Advanced Drug Delivery Reviews, vol. 8, pp. 1-38 (1992).

Burnstock, G. et al., "P2 Purinergic Receptors: Modulation of Cell Function and Therapeutic Potential", The Journal of Pharmacology and Experimental Therapeutics, vol. 295, No. 3, pp. 862-869 (2000).

Daniel, J.L. et al., "Molecular Basis for ADP-induced Platelet Activation: I. Evidence for Three Distinct ADP Receptors on Human Platelets", The Journal of Biological Chemistry, vol. 273, No. 4, pp. 2024-2029 (1998).

Fabre, J.-E. et al., "Decreased platelet aggregation, increased bleeding time and resistance to thromboembolism in $P2Y_1$-deficient mice", Nature Medicine, vol. 5, No. 10, pp. 1199-1202 (1999).

Gachet, C. et al., "The platelet P2 receptors in arterial thrombosis", Blood Cell, Molecules and Diseases, vol. 36, pp. 223-227 (2006).

(Continued)

*Primary Examiner* — Rita Desai
(74) *Attorney, Agent, or Firm* — Barry Jacobsen

(57) ABSTRACT

The present invention provides compounds of Formula (I): as defined in the specification and compositions comprising any of such novel compounds. These compounds are antagonists of $P2Y_1$ receptor which may be used as medicaments.

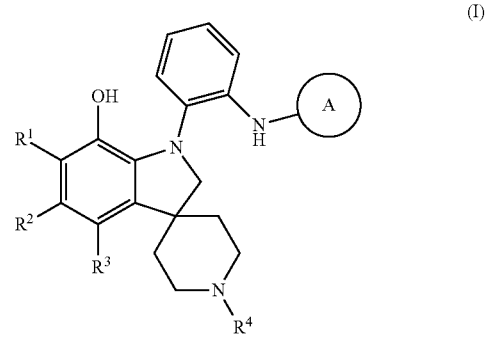

6 Claims, No Drawings

(56) References Cited

OTHER PUBLICATIONS

Gennaro, A.R., ed., Remington's Pharmaceutical Sciences, 18th Edition, pp. xv-xvi, Mack Publishing Company, publ. (1990).
Greene, T.W. et al., Protective Groups in Organic Synthesis, Second Edition, pp. ix-x, John Wiley & Sons, Inc., publ. (1991).
Greene, T.W. et al., Protective Groups in Organic Synthesis, Third Edition, pp. xi-xii, John Wiley & Sons, Inc., publ. (1999).
Hassan, J. et al., "Aryl-Aryl Bond Formation One Century after the Discovery of the Ullmann Reaction", Chemical Reviews, vol. 102, No. 5, pp. 1359-1469 (2002).
Hechler, B. et al., "MRS2500 [2-Iodo-$N^6$-methyl-($N$)-methanocarba-2'-deoxyadenosine-3',5'-bisphosphate], a Potent, Selective, and Stable Antagonist of the Platelet $P2Y_1$ Receptor with Strong Antithrombotic Activity in Mice", The Journal of Pharmacology and Experimental Therapeutics, vol. 316, No. 2, pp. 556-563 (2006).
Hechler, B. et al., "The $P2Y_1$ receptor, necessary but not sufficient to support full ADP-induced platelet aggregation, is not the target of the drug clopidogrel", British Journal of Haematology, vol. 103, pp. 858-866 (1998).
Himaya, T., Chapter 10: Organosilicon Compounds in Cross-coupling Reactions, Metal-catalyzed Cross-coupling Reactions, p. 421, Diederich, F. et al., eds., Wiley-VCH Verlag GmbH, publ. (1998).
Hu, C.H. et al., "Discovery of small molecule $P2Y_1$ antagonists: Amino-heterocycles as urea mimetics in the spiropiperidine indolinyl series", Abstracts of Papers, 244th ACS National Meeting & Exposition, Philadelphia, PA, Aug. 19-23, 2012, No. MEDI-127 (2012).
Ishiyama, K. et al., "Convenient synthesis of 7-hydroxyindole", Tetrahedron Letters, vol. 46, pp. 1021-1022 (2005).
Janssens, R. et al., "Cloning and Tissue Distribution of the Human $P2Y_1$ Receptor", Biochemical and Biophysical Research Communications, vol. 221, No. 3, pp. 588-593 (1996).
Jeon, Y.T. et al., "Identification of BMS-816106, potent $P2Y_1$ antagonist as a novel antiplatelet agent", Abstracts of Papers, 244th ACS National Meeting & Exposition, Philadelphia, PA, Aug. 19-23, 2012, No. MEDI-128 (2012).
Jin, J. et al., "Coactivation of two different G protein-coupled receptors is essential for ADP-induced platelet aggregation", Proc. Natl. Acad. Sci. USA, vol. 95, pp. 8070-8074 (1998).
Jin, J. et al., "Molecular Basis for ADP-induced Platelet Activation: II. The P2Y1 Receptor Mediates ADP-Induced Intracellular Calcium Mobilization and Shape Change in Platelets", The Journal of Biological Chemistry, vol. 273, No. 4, pp. 2030-2034 (1998).
Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).
Kihara, Y. et al., "Oxidative Heterocyclization Using Diethyl Azodicarboxylate", Synthesis, pp. 1020-1023 (1990).
Lenain, N. et al., "Inhibition of localized thrombosis in $P2Y_1$-deficient mice and rodents treated with MRS2179, a $P2Y_1$ receptor antagonist", Journal of Thrombosis and Haemostasis, vol. 1, pp. 1144-1149 (2003).
Léon, C. et al., "Key Role of the $P2Y_1$ Receptor in Tissue Factor-Induced Thrombin-Dependent Acute Thromboembolism: Studies in $P2Y_1$-Knockout Mice and Mice Treated with a $P2Y_1$ Antagonist", Circulation, vol. 103, pp. 718-723 (2001).
Ley, S.V. et al., "Modern Synthetic Methods for Copper-Mediated C(aryl)-O, C(aryl)-N, and C(aryl)-S Bond Formation", Angew. Chem. Int. Ed., vol. 42, pp. 5400-5449 (2003).
Liu, P. et al., "Synthesis of heterocycles via ligand-free palladium catalyzed reductive Heck cyclization", Tetrahedron Letters, vol. 48, pp. 2307-2310 (2007).
Miyaura, N. et al., "Palladium-Catalyzed Cross-Coupling Reactions of Organoboron Compounds", Chemistry Reviews, vol. 95, No. 7, pp. 2457-2483 (1995).
NCBI PubChem, CID 60150614—Compound Summary (Sep. 10, 2012).
Negishi, E., "Palladium- or Nickel-Catalyzed Cross Coupling. A New Selective Method for Carbon-Carbon Bond Formation", Acc. Chem. Res., vol. 15, pp. 340-348 (1982).
Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).
Nörenberg, W. et al., "Characterization and possible function of adenosine 5'-triphosphate receptors in activated rat microglia", Br. J. Pharmacol., vol. 111, pp. 942-950 (1994).
Qiao, J.X. et al., "Copper-Promoted Carbon-Heteroatom Bond Cross-Coupling with Boronic Acids and Derivatives", Synthesis, No. 6, pp. 829-856 (2011).
Qiao, J.X. et al., "Transformation of Anionically Activated Trifluoromethyl Groups to Heterocycles under Mild Aqueous Conditions", Organic Letters, vol. 13, No. 7, pp. 1804-1807 (2011).
Salter, M.W. et al., "ATP Causes Release of Intracellular $Ca^{2+}$ via the Phospholipase Cβ/$IP_3$ Pathway in Astrocytes from the Dorsal Spinal Cord", The Journal of Neuroscience, vol. 15, No. 4, pp. 2961-2971 (1995).
Savi, P. et al., "Role of P2Y1 purinoceptor in ADP-induced platelet activation", FEBS Letters, vol. 422, pp. 291-295 (1998).
Schumacher, W.A. et al., "Biomarker Optimization to Track the Antithrombotic and Hemostatic Effects of Clopidogrel in Rats", The Journal of Pharmacology and Experimental Therapeutics, vol. 322, No. 1, pp. 369-377 (2007).
Schwarz, O. et al., "Synthesis and biological evaluation of new antimalarial isonitriles related to marine diterpenoids", Tetrahedron Letters, vol. 43, pp. 1009-1013 (2002).
Semmelhack, M.F., ed., Comprehensive Organic Synthesis: Selectivity, Strategy & Efficiency in Modern Organic Chemistry, vol. 4: "Additions to and Substitutions at C—C π-Bonds", pp. v-vi, Pergamon Press, Inc., publ (1991).
Suzuki, A., "Synthetic studies via the cross-coupling reaction of organoboron derivatives with organic halides", Pure & App. Chem., vol. 63, No. 3, pp. 419-422 (1991).
Testa, B. et al., Hydrolysis in Drug and Prodrug Metabolism: Chemistry, Biochemistry, and Enzymology, pp. xi-xx, Wiley-VCH GmbH & Co., publ. (2003).
White, M.M. et al., Platelet Protocols: Research and Clinical Laboratory Procedures, pp. v-vii, Academic Press, publ. (1999).
Widder, K.J. et al., eds., Section III: "Prodrugs", Methods in Enzymology, vol. 112, pp. 309-396, Academic Press, Inc., publ. (1985).
Wong, P.C. et al., "Nonpeptide Factor Xa Inhibitors: I. Studies with SF303 and SK549, a New Class of Potent Antithrombotics", The Journal of Pharmacology and Experimental Therapeutics, vol. 292, No. 1, pp. 351-357 (2000).
Wong, P.C. et al., "Nonpeptide Factor Xa Inhibitors: II. Antithrombotic Evaluation in a Rabbit Model of Electrically Induced Carotid Artery Thrombosis", The Journal of Pharmacology and Experimental Therapeutics, vol. 295, No. 1, pp. 212-218 (2000).
Wong, P.C. et al., "Nonpeptide Factor Xa Inhibitors: III: Effects of DPC423, an Orally-Active Pyrazole Antithrombotic Agent, on Arterial Thrombosis in Rabbits", The Journal of Pharmacology and Experimental Therapeutics, vol. 303, No. 3, pp. 993-1000 (2002).
Yamada, Y. et al., "Preparation of 7-Halo-indoles by Thallation of $N$-Formylindoline and Their Attempted Use for Synthesis of the Right-Hand Segment of Chloropeptin", Chem. Pharm. Bull., vol. 54, No. 6, pp. 788-794 (2006).

AMINO-HETEROARYL 7-HYDROXY-SPIROPIPERIDINE INDOLINYL ANTAGONISTS OF P2Y1 RECEPTOR

The present application is a 371 application of International Application No. PCT/US2013/052446 filed on Jul. 29, 2013, which claims priority benefit of U.S. provisional application Ser. No. 61/678,190, filed Aug. 1, 2012; each of which is fully incorporated by reference herein.

FIELD OF THE INVENTION

The present invention provides novel aminoheteroaryl 7-hydroxy-spiropiperidine indolinyl compounds, and analogues thereof, which are selective inhibitors of the human P2Y$_1$ receptor. The invention also provides for various pharmaceutical compositions of the same and methods for treating diseases responsive to modulation of P2Y$_1$ receptor activity.

BACKGROUND OF THE INVENTION

Purinoreceptors bind to and are activated by a variety of both ribosylated (nucleotide) and non-ribosylated (nucleoside) purines. This distinction has been used to classify these receptors into two broad groups: the P1 receptors (A1, A2a, A2b, and A3), which bind to and are activated by the nucleoside adenosine, and the P2 receptors, which comprise a second, more diverse class of receptors which are activated by a wide variety of nucleotides including ATP, ADP, UTP, and UDP. The P2 receptors can be further subdivided into two distinct types of receptors; the ionotropic P2X receptors that mediate cation flux across cellular membranes in response to ATP and the metabotropic P2Y family of receptors which are G-protein coupled receptors. In humans, the P2Y family of receptors is generally considered to consist of seven distantly related members; P2Y$_1$, P2Y$_2$, P2Y$_4$, P2Y$_6$, P2Y$_{11}$, P2Y$_{12}$, and P2Y$_{13}$ (Boeynaems, J. M. et al., *Drug Development Research*, 52:187-189 (2001)). In addition, an eighth receptor, P2Y$_{14}$, has been considered by some to be a member of this class although it does not respond to ribosylated nucleotides and is activated by UDP-glucose (Abbracchio, M. P. et al., *Trends Pharmacol. Sci.*, 24:52-55 (2003)).

Several studies have suggested that modulators of specific members of the P2Y family of receptors could have therapeutic potential for the treatment of a variety of disorders (for review see Burnstock, G. et al., *J. Pharm. Exp. Ther.*, 295:862-869 (2000)), including diabetes, cancer, CF, and treatment of ischemia-reperfusion injury (Abbracchio M. P. et al., *Pharmacol. Ther.*, 64:445-475 (1994)). P2Y1 receptors, almost ubiquitous among human organs (Jassens, R. et al., *Biochem. Biophys. Res. Comm.*, 221:588-593 (1996)) have been identified on microglia (Norenberg, W. et al., *Br. J. Pharmacol.*, 111:942-950 (1994)) and on astrocytes (Salter, M. W. et al., *J. Neurosc.*, 15:2961-2971 (1995)). Extracellular ATP activates microglial and/or astrocytes via P2Y receptors and leads directly to the release of inflammatory mediators. Microglia and astrocytes are believed to play a role in the progression of Alzheimer's disease and other CNS inflammatory disorders such as stroke and multiple sclerosis.

Two members of the P2Y family, P2Y$_1$ and P2Y$_{12}$, are of particular interest as they have now both been shown to act as important receptors for ADP in platelets (Jin, J. et al., *Proc. Natl. Acad. Sci.*, 95:8070-8074 (1998)). ADP is a key activator of platelets and platelet activation is known to play a pivotal role in thrombus formation under conditions of high shear stress such as those found in the arterial circulation. In addition, more recent data has suggested that platelet activation may also play a role in mediating thrombus formation under lower shear stress such as that found in the venous circulation. ADP activates platelets by simultaneously interacting with both P2Y$_1$ and P2Y$_{12}$ to produce two separate intracellular signals which synergize together to produce complete platelet activation (Jin, J. et al., *J. Biol. Chem.*, 273:2030-2034 (1998)). The first signal arises from ADP driven activation of the P2Y$_1$ receptor and can most easily be tracked by measuring the transitory increase in intracellular free Ca$^{+2}$. This signal appears to mediate the initial shape change reaction and to initiate the process of platelet activation. The second signal appears to be derived from ADP activation of the P2Y$_{12}$ receptor and serves to consolidate the process and produce an irreversible platelet aggregate. Using three structurally related but distinct inhibitors of P2Y$_1$ (A3P5P, A3P5PS, and A2P5P), Daniel, J. L. et al. (*J. Biol. Chem.*, 273:2024-2029 (1998)), Savi, P. et al. (*FEBS Letters*, 422:291-295 (1998)), and Hechler, B. et al. (*Br. J. Haematol.*, 103:858-866 (1998)) were the first to publish the observation that the inhibition of P2Y$_1$ activity alone could block ADP-driven aggregation independently of the P2Y$_{12}$ receptor. Although inhibition of platelet reactivity is often thought of as firm evidence of an anti-thrombotic activity, these antagonists lacked the necessary pharmacological properties for in vivo study. The first direct demonstration that inhibition of P2Y$_1$ activity could lead to an anti-thrombotic effect in vivo was reported by Leon, C. et al., *Circulation*, 103:718-723 (2001), in a model of thromboplastin induced thromboembolism using both a P2Y$_1$ knock-out mouse and the P2Y$_1$ antagonist MRS-2179 (Baurand, A. et al., *Cardiovascular Drug Reviews*, 21:67-76 (2003)). These results were subsequently extended to include the inhibition of both venous and arterial thrombosis in the rat (Lenain, N. et al., *J. Thromb. Haemost.*, 1:1144-1149 (2003)) and the confirmation of the phenotype of the P2Y$_1$ knock-out mouse in a second laboratory using an independently derived animal (Fabre, J-E. et al., *Nature Medicine*, 5:1199-1202 (1999)). These studies highlighted the need for more potent and selective P2Y$_1$ antagonists and recently, using the P2Y$_1$ antagonist MRS-2500 (Hechler, B. et al., *J. Pharmacol Exp. Ther.*, 316:556-563 (2006)) succeeded in demonstrating strong antithrombotic activity for a selective P2Y$_1$ antagonist in the mouse. Taken together, these data suggest that the discovery of novel P2Y$_1$ antagonists with improved pharmaceutical characteristics could have significant utility in the treatment of a variety of thrombotic or thromboembolic disorders (see Gachet, C. et al., *Blood Cell, Molecules and Disease*, 36:223-227 (2006) for a recent review).

U.S. Patent Publication No. 2006/0293281 A1 published Dec. 28, 2006 discloses a series of P2Y$_1$ antagonists including spiropiperidine indolinyl of the following formula:

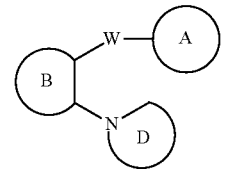

wherein ring A is C$_{6-10}$ aryl substituted with 0-5 R$^1$, or a 5- to 10-membered heterocycle comprising: carbon atoms and 1-4 heteroatoms selected from N, NR$^{11}$, O, and S(O)$_p$, wherein said heterocycle is substituted with 0-5 R$^1$;

ring B is phenyl or naphthyl substituted with 0-4 $R^7$, or a 5- to 10-membered heteroaryl comprising: carbon atoms and 1-4 ring heteroatoms selected from N, $NR^{11}$, $S(O)_p$, and O, wherein said heteroaryl is substituted with 0-4 $R^7$;

one of the ring D groups is

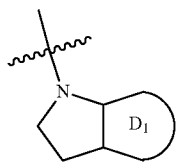

substituted with 0-5 $R^{6a}$; wherein $D_1$ is a 5- to 7-membered carbocycle or a 5-6-membered heterocycle comprising: carbon atoms and 0-3 ring heteroatoms selected from N, $NR^{11}$, O, and $S(O)_p$, and 0-2 carbonyl groups, and 0-3 double bonds;

one of the W groups is $NR^{18}$;

$R^{6a}$ is a variable defined therein;

alternatively, when two $R^{6a}$ groups are attached to the same carbon atom, together with the carbon atom to which they are attached, they form a 3- to 7-membered carbocyclic or heterocyclic ring comprising: carbon atoms and 0-3 heteroatoms selected from N, $NR^{11}$, O, Si, and $S(O)_p$, 0-1 carbonyl and 0-3 ring double bonds, wherein said carbocyclic or heterocyclic ring is substituted with 0-3 $R^b$; and other variables are defined therein.

It is desirable to find new compounds with improved pharmacological characteristics compared with known $P2Y_1$ antagonists. For example, it is desirable to find new compounds with improved antiplatelet activity in the platelet aggregation functional assay and good binding affinity in the $P2Y_1$ binding assay

SUMMARY OF THE INVENTION

The present disclosure provides novel aminoheteroaryl 7-hydroxy-spiropiperidine indolinyl compounds and their analogues, including stereoisomers, tautomers, pharmaceutically acceptable salts, or solvates thereof, which are useful as selective inhibitors of the $P2Y_1$ receptor.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in therapy.

The compounds of the invention may be used for the manufacture of a medicament for the treatment and/or prophylaxis of thromboembolic disorders.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

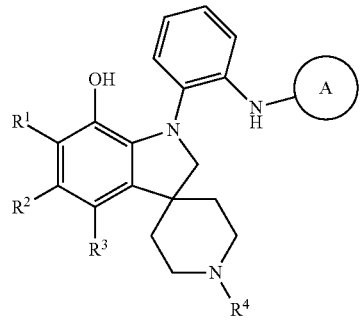

or a stereoisomer, a tautomer, a pharmaceutically acceptable salt, a solvate, or a prodrug thereof, wherein:

ring A is independently selected from

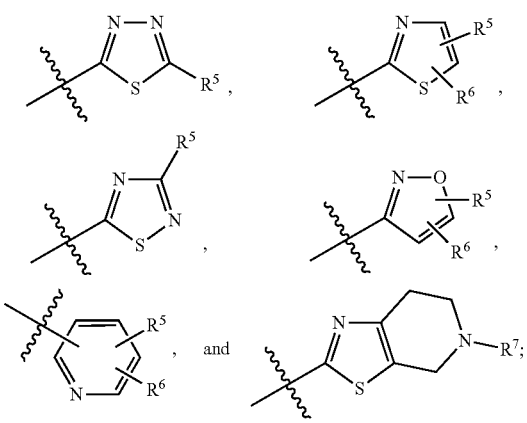

and $R^1$ is independently selected from H, halogen and OH;

$R^2$ is independently H or halogen;

$R^3$ is independently selected from H, halogen, $C_{1-6}$ haloalkyl, CN and $CO_2(C_{1-4}$ alkyl);

$R^4$ is independently $C_{2-6}$ alkyl substituted with 0-3 F atoms;

$R^5$ is, independently at each occurrence, selected from $C_{1-6}$ alkyl, $C_{1-6}$ alkenyl, $CO_2(C_{1-4}$ alkyl), phenyl, pyridyl, benzyl, pyrazolyl, N—($C_{1-4}$ alkyl)-pyrazolyl, pyrazinyl, quinoxalinyl, and

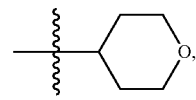

wherein each ring moiety is substituted with zero to three substituents independently selected from the group consisting of: halogen, $C_{1-6}$ alkyl, $C_{1-6}$ haloalkyl, $C_{1-6}$ haloalkoxy, and $N(C_{1-4}$ alkyl)$_2$;

$R^6$ is, independently at each occurrence, selected from H, $C_{1-6}$ alkyl, $C_{1-6}$ haloalkyl, CN and $CO_2(C_{1-4}$ alkyl); and $R^7$ is independently $C_{1-6}$ alkyl.

In a second aspect, the present invention includes a compound of Formula (II):

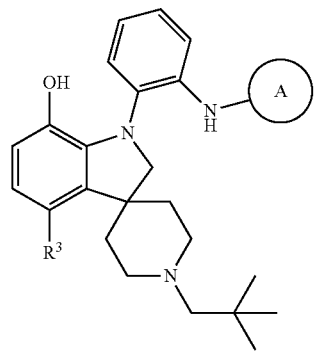

(II)

or a stereoisomer, a tautomer, a pharmaceutically acceptable salt, or a solvate thereof, within the scope of the first aspect.

In a third aspect, the present invention includes a compound of Formula (I) or (II), or a stereoisomer, a tautomer, a pharmaceutically acceptable salt, or a solvate thereof, within the scope of the first or second aspect, wherein:

ring A is independently selected from

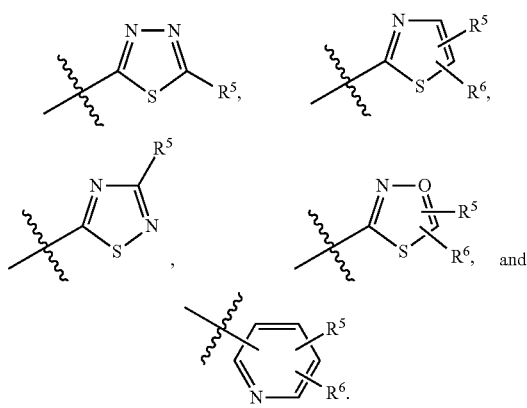

and

In a fourth aspect, the present invention includes a compound of Formula (I) or (II), or a stereoisomer, a tautomer, a pharmaceutically acceptable salt, or a solvate thereof, within the scope of any of the above aspect, wherein:

ring A is independently selected from

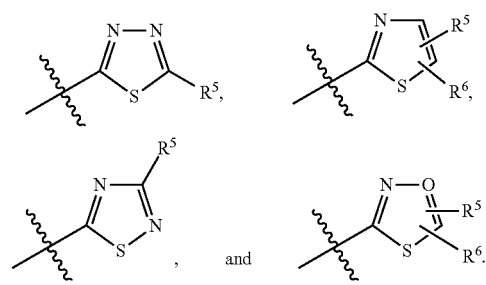

and

In a fifth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the fifth aspect.

In another embodiment, ring A is

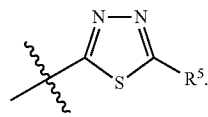

In another embodiment, ring A is

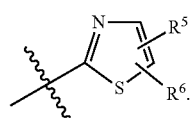

In another embodiment, ring A is

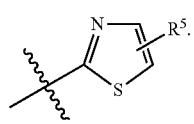

In another embodiment, ring A is

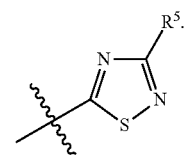

In another embodiment, ring A is

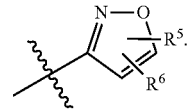

In another embodiment, ring A is

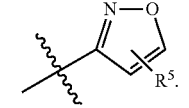

In another embodiment, ring A is

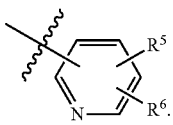

In another embodiment, ring A is

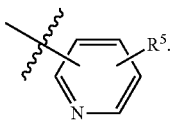

In another embodiment, ring A is

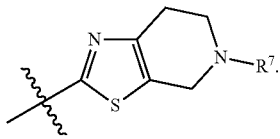

In another embodiment, the compounds of the present invention have in vitro human antiplatelet activity in the platelet aggregation assay: PA $IC_{50}$ values ≤40 µM with 10 µM ADP.

In another embodiment, the compounds of the present invention have in vitro human antiplatelet activity in the platelet aggregation assay: PA $IC_{50}$ values ≤5 µM with 10 µM ADP.

In another embodiment, the compounds of the present invention have in vitro human antiplatelet activity in the platelet aggregation assay: PA $IC_{50}$ values ≤1 µM with 10 µM ADP.

In another embodiment, the compounds of the present invention have in vitro human antiplatelet activity in the platelet aggregation assay: PA $IC_{50}$ values ≤2 µM with 10 µM ADP.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the modulation of platelet reactivity comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In one embodiment, the present invention provides a method for the treatment and/or prophylaxis of thromboembolic disorders, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, and thromboembolic disorders in the chambers of the heart.

In another embodiment, the thromboembolic disorder is selected from the group consisting of unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a compound of the present invention for use in therapy.

In another embodiment, the present invention provides a compound of the present invention for use in therapy for the treatment and/or prophylaxis of thromboembolic disorders.

In another embodiment, the present invention also provides the use of a compound of the present invention for the manufacture of a medicament for the treatment and/or prophylaxis of thromboembolic disorders.

In another embodiment, the present invention provides a method for the treatment and/or prophylaxis of thromboembolic disorders, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of thromboembolic disorders.

The compounds of the present invention may be employed in combination with additional therapeutic agent(s) selected from one or more, preferably one to three, of the following therapeutic agents: potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning.

In another embodiment, additional therapeutic agent(s) used in combined pharmaceutical compositions or combined methods or combined uses, are selected from one or more, preferably one to three, of the following therapeutic agents in treating a thromboembolic disorder: an anti-arrhythmic agent, an anti-hypertensive agent, an anticoagulant agent, an anti-platelet agent, a thrombin inhibiting agent, a thrombolytic agent, a fibrinolytic agent, a calcium channel blocker, a cholesterol/lipid lowering agent.

In another embodiment, additional therapeutic agent(s) used in combined pharmaceutical compositions or combined methods or combined uses, are selected from one or more, preferably one to three, of the following therapeutic agents in treating a thromboembolic disorder: warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, apixaban, rivaroxaban, edoxaban, dabigatran, disulfatohirudin, tissue plasminogen activator, modified tissue plasminogen activator, anistreplase, urokinase, and streptokinase.

In another embodiment, additional therapeutic agent(s) used in combined pharmaceutical compositions or combined methods or combined uses, are selected from one or more, preferably one to three, of the following therapeutic agents in treating a thromboembolic disorder: an antihypertensive agent selected from ACE inhibitors, AT-1 receptor antagonists, ET receptor antagonists, dual ET/AII receptor antagonists, and vasopepsidase inhibitors, or an antithrombotic agent selected from an antiplatelet agent selected from GPIIb/IIIa blockers, $P2Y_{12}$ antagonists, thromboxane receptor antagonists, and aspirin.

In another embodiment, the additional therapeutic agent(s) are an anti-platelet agent or a combination thereof.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" (or alkylene), is intended to include $C_1$, $C_2$, $C_3$, $C_4$, $C_5$, and $C_6$ alkyl groups. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "counter ion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of Formula (I), Formula (II), or Formula (III) may have prodrug forms. Any compound that will be converted in vivo to provide the bioactive agent (i.e., a compound of Formula (I), Formula (II) or Formula (III)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield compounds of the present invention per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyloxymethyl or ethoxycarbonyloxymethyl, glycyloxymethyl, phenylglycyloxymethyl, (5-methyl-2-oxo-1,3-dioxolen-4- yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

2MeS-ADP 2 methylthio adenosine diphosphate
AcOH or HOAc acetic acid
AIBN azobisisobutyronitrile
$AlCl_3$ aluminum chloride
$BBr_3$ boron tribromide
$BCl_3$ boron trichloride
$BH_3$ borane
BINAP 2,2'-bis(diphenylphosphino)-1,1'-binaphthyl
Bn benzyl
Boc tert-butyloxycarbonyl
Bu butyl
cDNA complimentary DNA
$CH_2Cl_2$ dichloromethane
$CH_3CN$ or ACN acetonitrile
conc. concentrated
$Cs_2CO_3$ cesium carbonate
$Cu(OAc)_2$ copper (II) acetate
DCM dichloromethane
DCM dichloromethane
DIEA or DIPEA diethylpropyl amine
DMEM Dulbecco's modified Eagle media
DMF dimethyl formamide
DMSO dimethyl sulfoxide
D-PBS Dulbecco's Phosphate Buffered Saline
EDTA ethylenediaminetetraacetic acid
Et ethyl
$Et_2O$ diethyl ether
EtOAc ethyl acetate
EtOH ethanol
FBS Fetal Bovine Serum
FG functional group
$H_2SO_4$ sulfuric acid
HCl hydrochloric acid 4-(2-hydroxyethyl)piperaxine-1-ethanesulfonic
HEPES acid
Hex hexane
Hunig's base N, N-diisopropylethyl amine
i-Bu isobutyl
i-Pr isopropyl
i-PrOH or IPA isopropanol
$K_2CO_3$ potassium carbonate
$K_3PO_4$ potassium phosphate
KOAc potassium acetate
K-O-t-Bu/t-BuOK potassium tert-butoxide
LAH/$LiAlH_4$ lithium aluminum hydride
$LiBH_4$ lithium borohydride
mCPBA or m-CPBA meta-chloroperbenzoic acid
Me methyl
MeOH methanol
$MgSO_4$ magnesium sulfate
MsOH or MSA methylsulfonic acid
$Na_2S_2O_4$ sodium dithionite
$Na_2SO_4$ sodium sulfate
$NaBH_4$ sodium borohydride
NaCl sodium chloride
$NaHCO_3$ sodium bicarbonate
NaOH sodium hydroxide
NaO-t-Bu/t-BuONa sodium tert-butoxide
NBS N-bromosuccinimide
NCS N-chlorosuccinimide
$NH_4Cl$ ammonium chloride OTs tosylate, para-toluenesulfonate
P(t-Bu)$_3$ tri-tert-butylphosphine
PCy$_3$ tricyclohexylphosphine
Pd(OAc)$_2$ palladium acetate
Pd/C palladium on carbon
Pd$_2$(dba)$_3$ tris(dibenzylideneacetone)dipalladium(0)
PG protecting group
Ph phenyl
Pr propyl
RED-AL® sodium bis(2-methoxyethoxy)aluminum hydride
Sat'd Saturated
SiO$_2$ silica oxide
SnCl$_2$ tin(II) chloride
TBAI tetra-n-butylammonium iodide
t-Bu tert-butyl
TEA triethylamine
TFA trifluoro acetic acid
THF tetrahydrofuran
TMSCN trimethylsilyl cyanide
TRIS tris (hydroxymethyl) aminomethane 4,5-bis(diphenylphosphino)-9,9-
Xantphos dimethylxanthene
Zn zinc
ZnCl$_2$ zinc chloride
ZnI$_2$ zinc iodide
Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Wiley-Interscience, 3rd Edition (1999)).

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups In Organic Synthesis*, Wiley and Sons (1991)).

Schemes 1-12 describe synthetic routes of making compounds of the invention. Schemes 1 and 2 describe several preparations of the amine intermediate 1 and Schemes 3-6 illustrate the possible preparations of the substituted indoline derivative 3 via a variety of methods from commercially available starting materials or can readily be prepared from commercially available materials by methods known to one skilled in the art of organic synthesis. Scheme 7 exemplifies the preparations of the amine intermediates 37 in the present invention wherein, R$^3$ is a halogen group, such as Cl, or trifluoromethyl group. Schemes 8-11 illustrate the preparations of compounds in the present invention wherein A ring is a substituted five- or six-membered heteroaryl. Scheme 12 elaborates further functionalization of R$^3$ of the molecule when R$^3$ is a trifluoromethyl group to synthesize compounds of the present invention wherein R$^3$ is a nitrile or an ester group.

Scheme 1 outlines one possible preparation of aniline intermediates 1, which proceeds by aromatic nucleophilic substitution followed by reduction. Nitro phenyl derivatives or nitro pyridinyl derivatives 2, substituted in the ortho position with a halogen (such as chlorine or fluorine), are commercially available or can readily be prepared by one skilled in the art of organic synthesis. They can be reacted with NH-containing cyclics 3 as nucleophiles to provide the corresponding compounds 4. Typical reaction conditions involve the reaction of a nucleophile and a halonitro aryl/heteroaryl derivative either in an organic solvent such as THF, DMF, toluene, dioxane or n-butanol, or under neat condition, in the presence of a base such as potassium carbonate, cesium carbonate, triethylamine, sodium/potassium tert-butoxide, or DIEA. The reaction temperature is usually between room temperature and reflux condition. Reaction conditions can be chosen based on the nucleophilicity of 3 and/or halogen difference. Microwave irradiation and/or heating at higher temperature can also be used to accelerate the rate of reaction. Following aromatic nucleophilic substitution, the resulting nitro derivatives 4 can be reduced to the corresponding anilines. Typical conditions include hydrogenation in the presence of a metal catalyst such as palladium or platinum. Other conditions include treatment with reducing agents such as SnCl$_2$ or Zinc or iron powder with ammonium chloride.

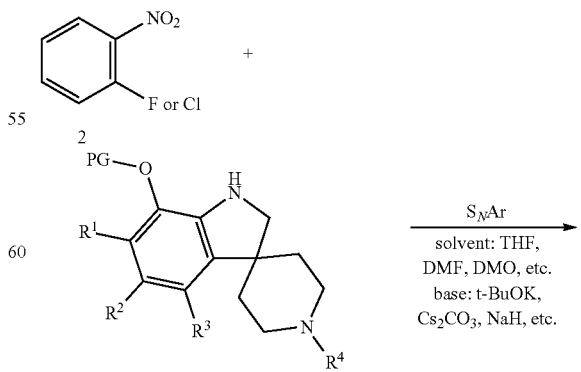

Scheme 1

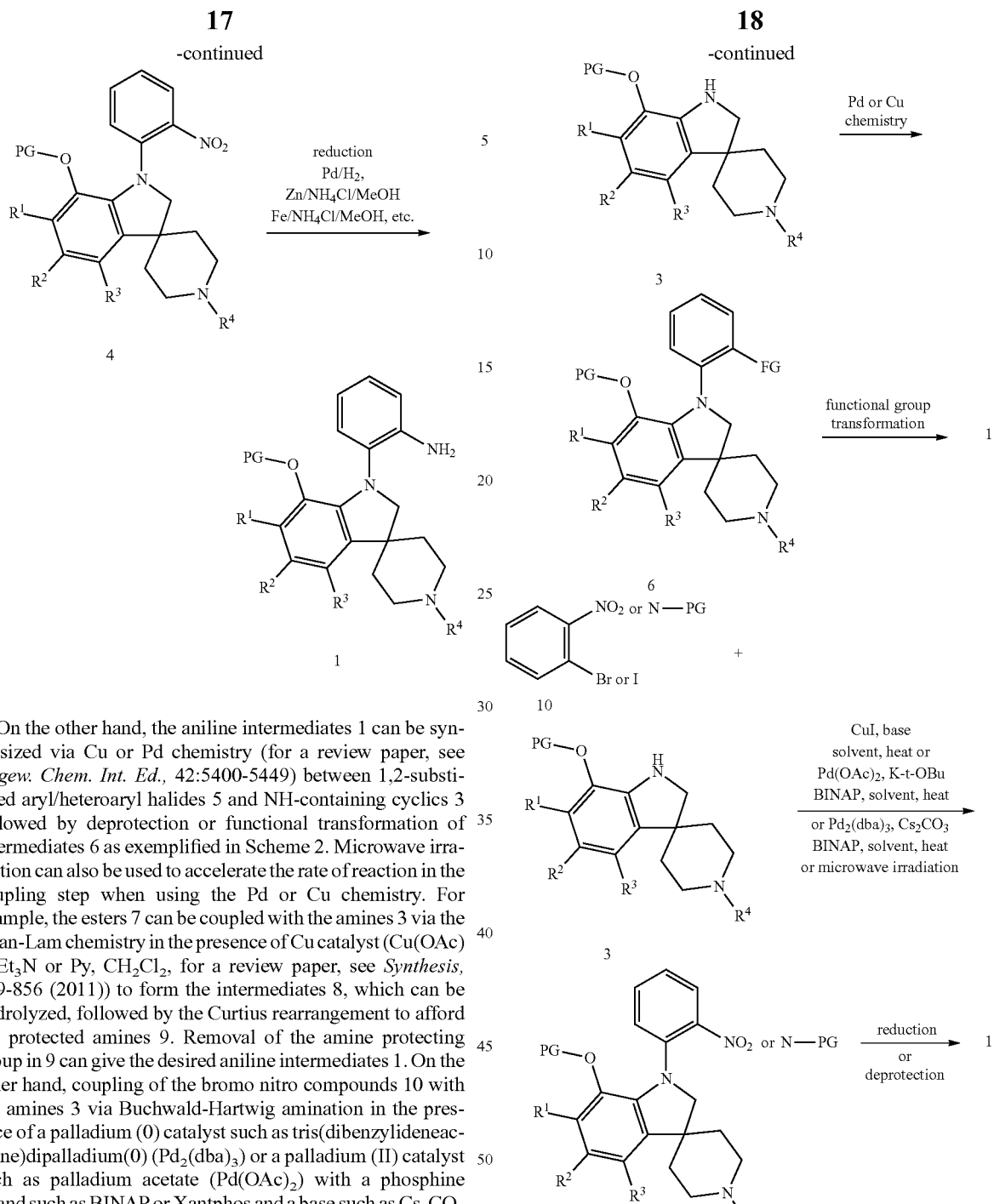

On the other hand, the aniline intermediates 1 can be synthesized via Cu or Pd chemistry (for a review paper, see *Angew. Chem. Int. Ed.*, 42:5400-5449) between 1,2-substituted aryl/heteroaryl halides 5 and NH-containing cyclics 3 followed by deprotection or functional transformation of intermediates 6 as exemplified in Scheme 2. Microwave irradiation can also be used to accelerate the rate of reaction in the coupling step when using the Pd or Cu chemistry. For example, the esters 7 can be coupled with the amines 3 via the Chan-Lam chemistry in the presence of Cu catalyst (Cu(OAc)$_2$, Et$_3$N or Py, CH$_2$Cl$_2$, for a review paper, see *Synthesis*, 829-856 (2011)) to form the intermediates 8, which can be hydrolyzed, followed by the Curtius rearrangement to afford the protected amines 9. Removal of the amine protecting group in 9 can give the desired aniline intermediates 1. On the other hand, coupling of the bromo nitro compounds 10 with the amines 3 via Buchwald-Hartwig amination in the presence of a palladium (0) catalyst such as tris(dibenzylideneacetone)dipalladium(0) (Pd$_2$(dba)$_3$) or a palladium (II) catalyst such as palladium acetate (Pd(OAc)$_2$) with a phosphine ligand such as BINAP or Xantphos and a base such as Cs$_2$CO$_3$ or t-BuONa, can afford the nitro intermediates 11. Reduction of the nitro group in 11 with a variety of reducing reagents such as Zn, Fe, Pd/C—H$_2$, SnCl$_2$, Na$_2$S$_2$O$_4$, can afford the desired aniline intermediates 1.

Scheme 2

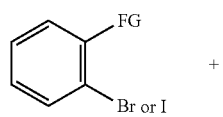

Compounds of the present invention wherein the amine intermediates 3 are substituted indoline derivatives, can be prepared by using the methods shown in Schemes 3-8 and by using methods known to those skilled in the art of organic synthesis.

Scheme 3 illustrates the preparation of the indoline derivatives 3 via Fischer indole synthesis followed by reduction of the indolenine intermediates. Substituted phenyl hydrazines 12 are commercially available or can readily be prepared from commercially available materials by methods known to one skilled in the art of organic synthesis. Thus, Fischer indole reaction of the substituted phenyl hydrazines 12 and the aldehydes 13 under acidic conditions (e.g., H$_2$SO$_4$, HCl, HOAc, TFA, MsOH, ZnCl$_2$) at reaction temperature from 0° C. to refluxing temperature in solvent such as CH$_2$Cl$_2$, toluene, EtOH, HOAc, 1,4-dioxane, can yield the indolenine intermediates 15, followed by reduction of 15 with reducing agents such as NaBH$_4$, NaCNBH$_3$, or LiBH$_4$ in MeOH at −78° C. to room temperature or at reflux can afford the desired indolines 3.

Scheme 3

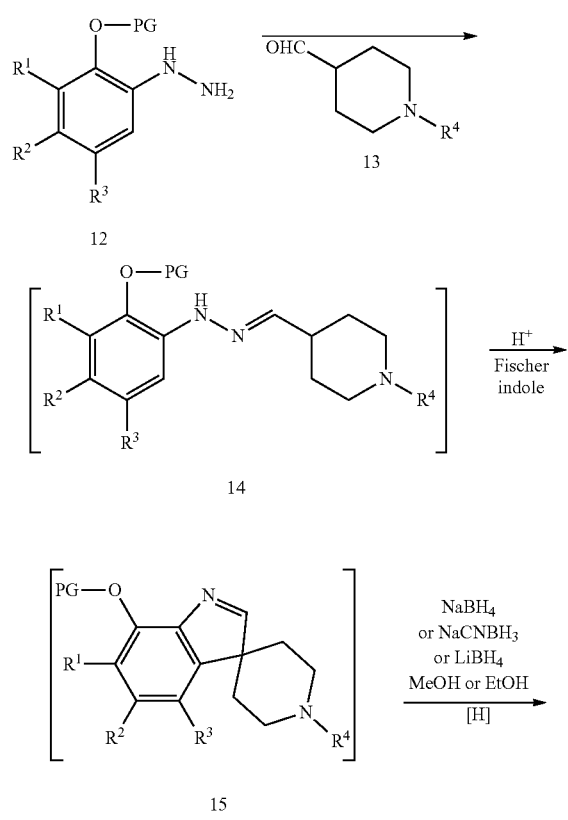

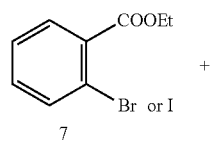

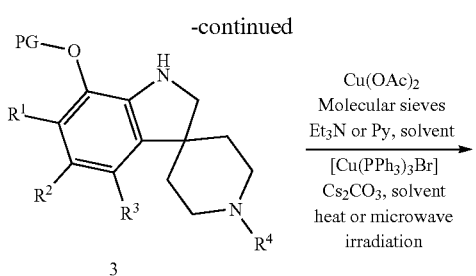

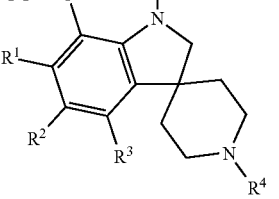

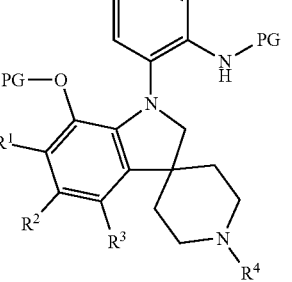

Alternatively, the indolinyl derivatives 3 in the present invention can be synthesized via the reduction of indol-2-ones 18 using reducing agents such as LiAlH$_4$, BH$_3$ (Scheme 4). The indol-2-one intermediates 18 are either commercially available or can be prepared using methods known to those skilled in the art of organic synthesis. For example, sequential alkylation of intermediates 16 followed by reduction of the nitro group in 17 and subsequent intermolecular cyclization can afford the desired indol-2-ones 18.

Scheme 4

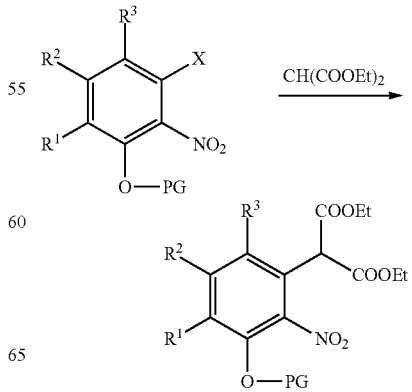

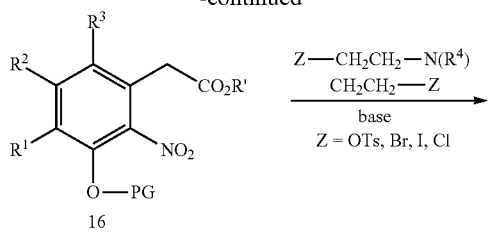

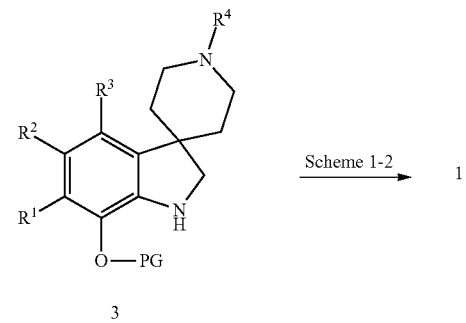

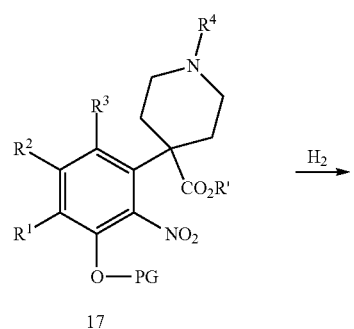

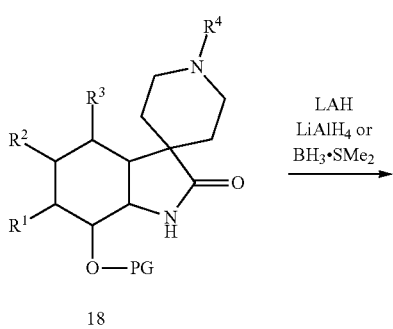

Alternatively, in Scheme 5, the indol-2-one intermediates 18 can be prepared from the reduction of the indol-2,3-diones 19 followed by sequential alkylation. On the other hand, the indol-2-ones 18 can be prepared from the Cl, Br, or I intermediates 20 via either intramolecular Heck reaction in the presence of a palladium catalyst (such as $Pd_2(dba)_3$, Pd$(OAc)_2$), a phosphine ligand (such as BINAP, $PCy_3$, P(t-Bu)$_3$), a base (such as NaO-t-Bu), in solvent (such as 1,4-dioxane, toluene) or radical cyclization with $Bu_3SnH$, AIBN in DMF or toluene under normal heating or microwave irradiation.

Scheme 6 indicates that the indoline intermediates 3 can also be prepared via alkylation of the nitrile intermediates 21 followed by reductive cyclization of the resulting piperidinyl derivatives 22. The nitrile intermediates 21 can be prepared from displacement either the bromides, or tosylates 23 with nitrile anion. Intermediates 3 can also be obtained from tertiary alcohols 24 reacting with TMSCN in the presence of a Lewis acid (such as $ZnI_2$) (Schmalz, Tetrahedron Letters, 1009 (2002)). The alcohols 24 can be prepared via ortho lithiation of the fluorides 25, then trapping with the ketones 26.

Scheme 5

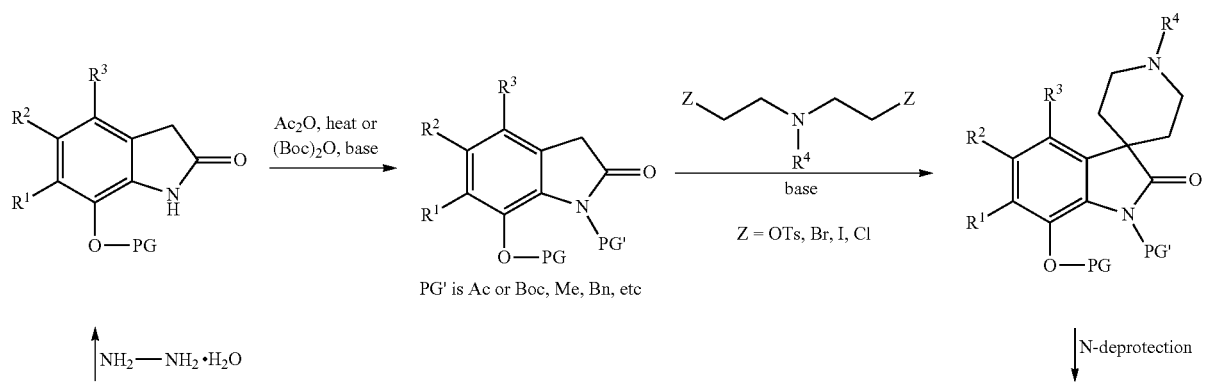

-continued
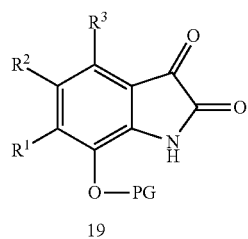
19
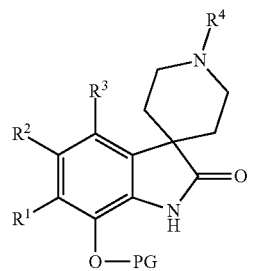
18
Intramolecular Heck
Pd-Cat (such as Pd$_2$(dba)$_3$,
Pd(OAc)$_2$, Ligand (such as
BINAP, PCy$_3$, P-t-tBu$_3$), base
(such as NaOt-Bu solvent (such
as 1,4-dioxane)
Intramolecular radical cyclization
Bu$_3$SnH, AIBN, DMF or toluene,
microwave irradiation or heat
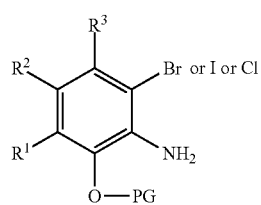 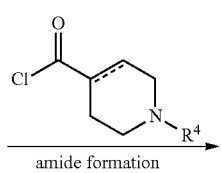 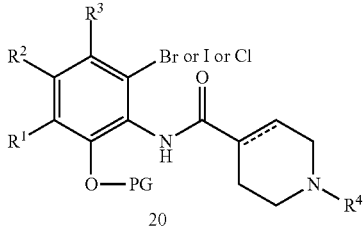
amide formation
20

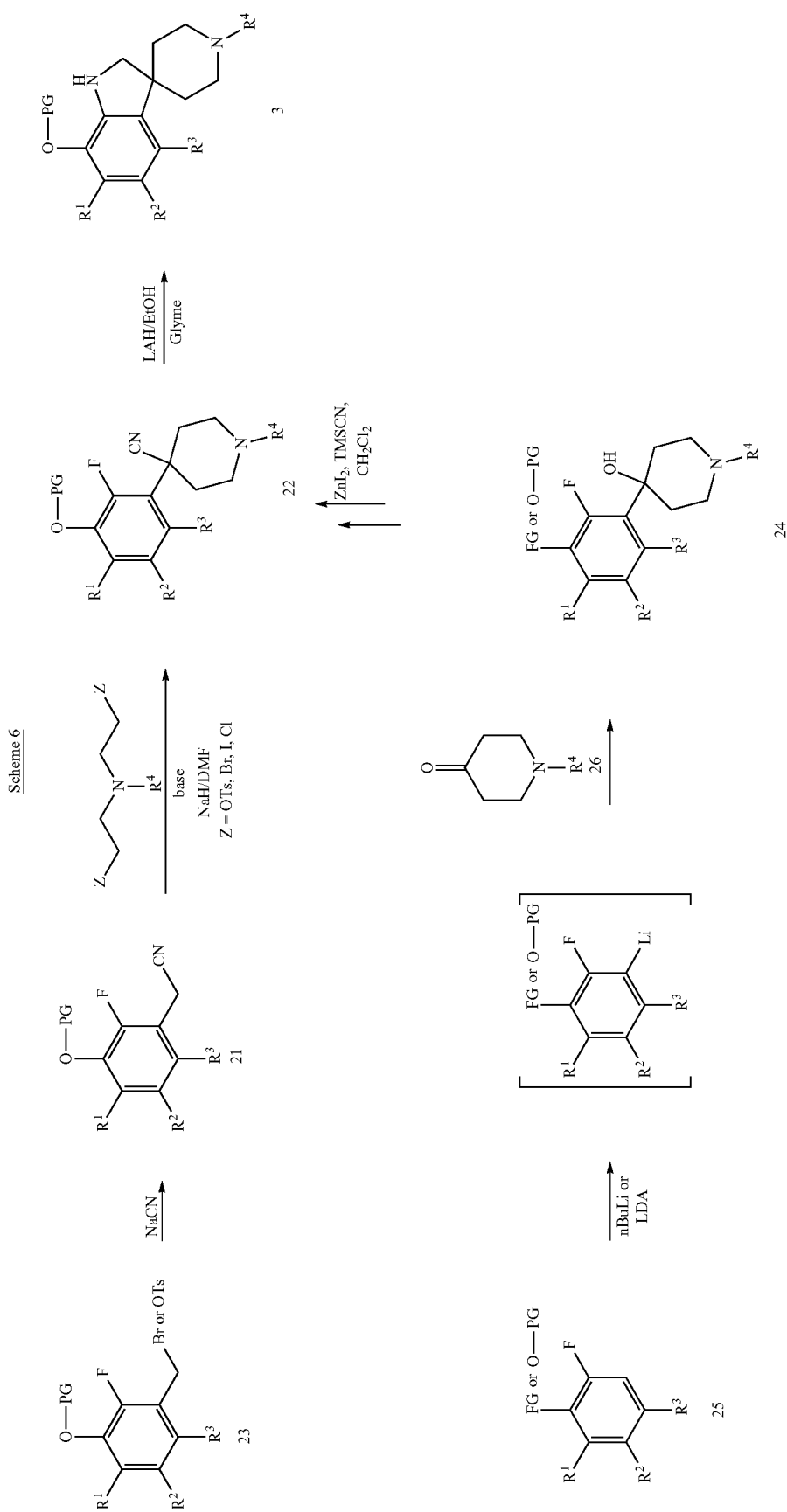

Scheme 7 illustrates the synthesis of the amine intermediates 37 in the present invention wherein, $R^3$ is a halogen group, such as Cl, or a trifluoromethyl group. Nitration of the methoxy intermediates 27 followed by reduction of the nitro group in 28 afforded the anilines 29. Diazotization of 29 followed by reduction formed the hydrazines 30. Hydrazone formation of 30 with the aldehydes 31, followed by cyclic imine formation under Fischer indole condition and subsequently reducing the imines, afforded the pivaloyl protected spiropiperidinyl indoline intermediates 32. Pd-catalyzed cross-coupling of 32 with 33 under Buchwald-Hartwig condition or $S_NAr$ displacement of 34 with 32 yielded the N-aryl derivatives 35. Reduction of the $NO_2$ group of 35 followed by reduction of the pivaloyl group in 36 to the neopentyl group led to the aniline intermediates 37.

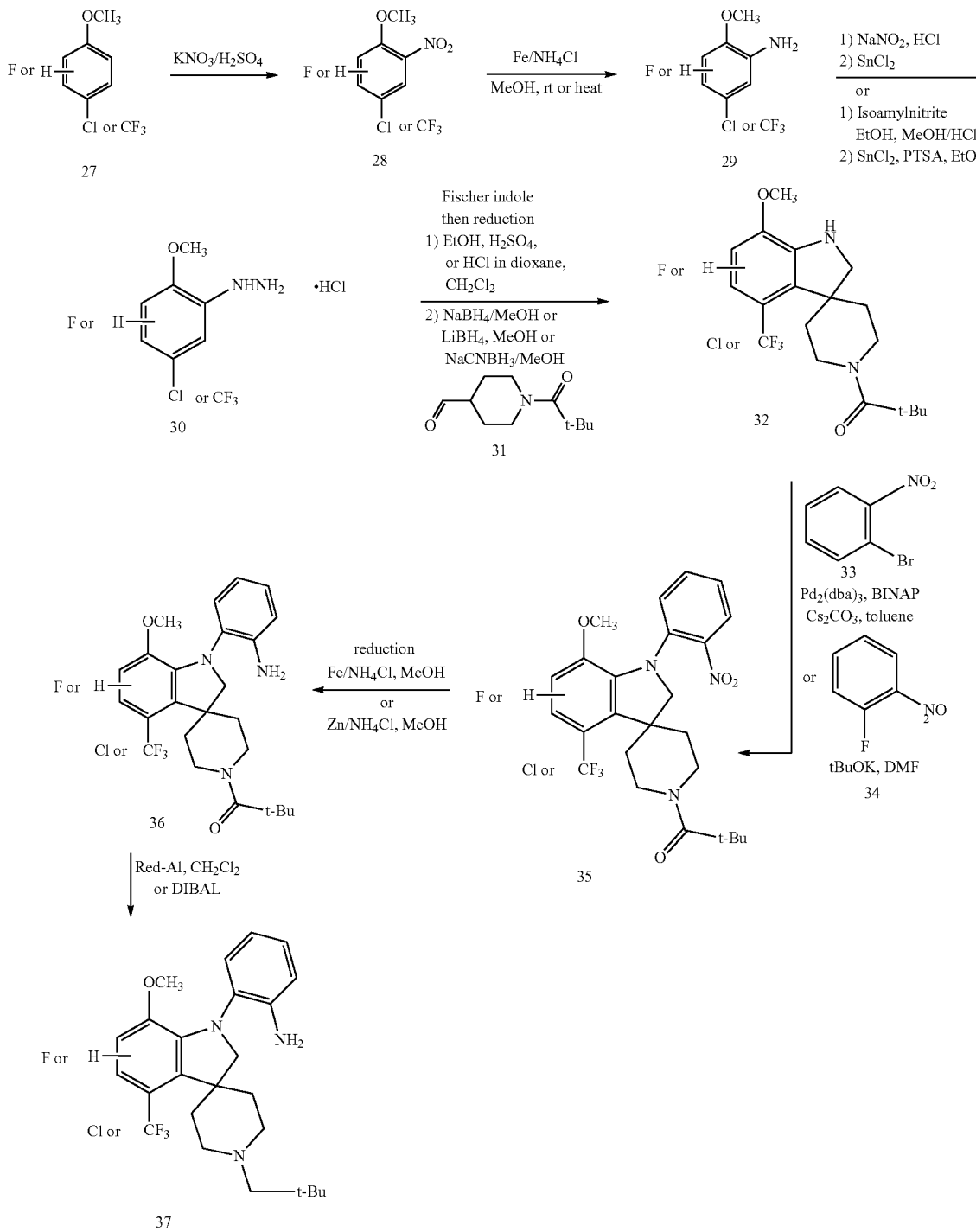

Scheme 7

Scheme 8 illustrates an efficient transformation of spiropiperidinyl indolines 3 to various aminoheterocycle urea mimics 41. Indolines 3 couple with 1,2-disubstituted benzenes 38 (where Y and Y' can be halogen) by Buchwald-Hartwig reaction in the presence of $Pd_2(dba)_3$, rac-BINAP, and $Cs_2CO_3$ in toluene or under other standard C—N cross coupling conditions, such as Ullmann-Goldberg or Chan-Lam reactions, to afford the key bromo intermediates 39. The second Buchwald-Hartwig reaction or C—N cross coupling reaction of 39 with various heteroaryl anilines gives the corresponding aminoheterocycles 40. The protective group then can be removed to give the compounds of the present invention 41. When the protecting group on the phenol is methyl, demethylation can occur with $BBr_3$, $BCl_3$, $BBr_3.SMe$, $BCl_3.SMe AlCl_3$, or $BCl_3$/ TBAI (tetra-n-butylammonium iodide) at temperatures between −78° C. and refluxing temperature in a solvent such as $CH_2Cl_2$. When heating is needed, the reaction can also occur under microwave irradiation to shorten the reaction time. When the protecting group on the phenol is a benzyl group, debenzylation can occur by using hydrogenation (such as Pd/C, $H_2$) or by using $AlCl_3$ in $CH_2Cl_2$ in a variety of solvents such as methanol, EtOAc.

Scheme 8

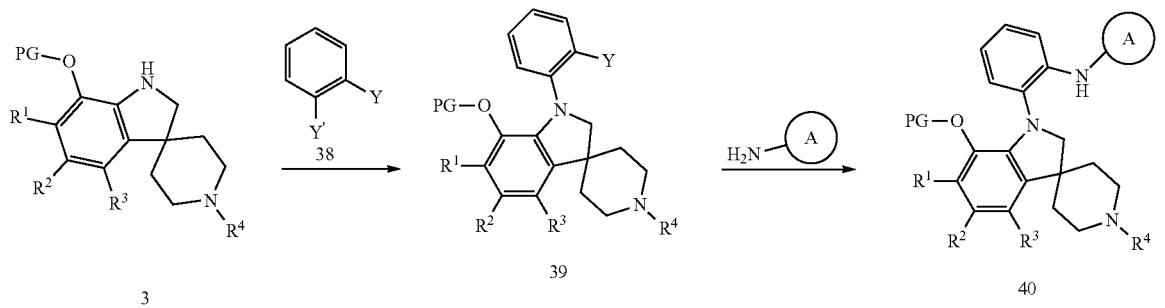

deprotection for example:
when PG = Me,
demethylatation with
$BBr_3$, $BCl_3$, $AlCl_3$, etc when PG = benzyl,
using hydrogenation
with Pd/C, $H_2$ or $AlCl_3$/DCM

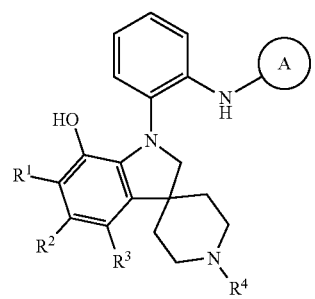

41

Scheme 9 describes the preparation of compounds of the present invention from functional intermediates 42. Anilines 1 can be treated with a thiophosgene equivalent in an organic solvent such as dichloromethane, dichloroethane or toluene to produce the corresponding isothiocyanates 42. Thiophosgene equivalents include thiocarbonic O,O-dipyridin-2-yl ester 1,1'-thiocarbonyldi-2,2'-pyridone, carbon disulfide, thiocarbonyl-diimidazole, and thiophosgene. Treatment of thioisocyanate intermediates 42 with acrylhydrazides (when Z=N) or 2-amino-1-ethanones (when Z=CH or CR') in a solvent such as dichloromethane at temperatures between 0 to 50° C. provides intermediates 43. Treatment of intermediates 43 with an acid such as neat sulfuric acid, or an equivalent reagent, at temperatures between 0 to 20° C. provides compounds 44. The protective group then can be removed following the procedure described in Scheme 8 to give the compounds of the present invention 46. Acylhydrazides are commercially available or can be prepared from carboxylic acids, acyl chlorides or equivalent reagents by methods known to one skilled in the art of synthetic chemistry. Alternately compounds 43 can be prepared by treatment of intermediates 42 with t-butyl carbazate, or an equivalent reagent, in a solvent such as dichloromethane at temperature between 0 to 50° C. Subsequent removal of the t-butoxycarbonyl with an acid such as TFA in a solvent such as dichloromethane provides intermediates 45. Treatment of intermediates 45 with an acyl chloride, or similar suitably activated acylating reagent, in a solvent such as tetrahydrofuran at temperatures between 0 to 50° C. provides intermediates 43.

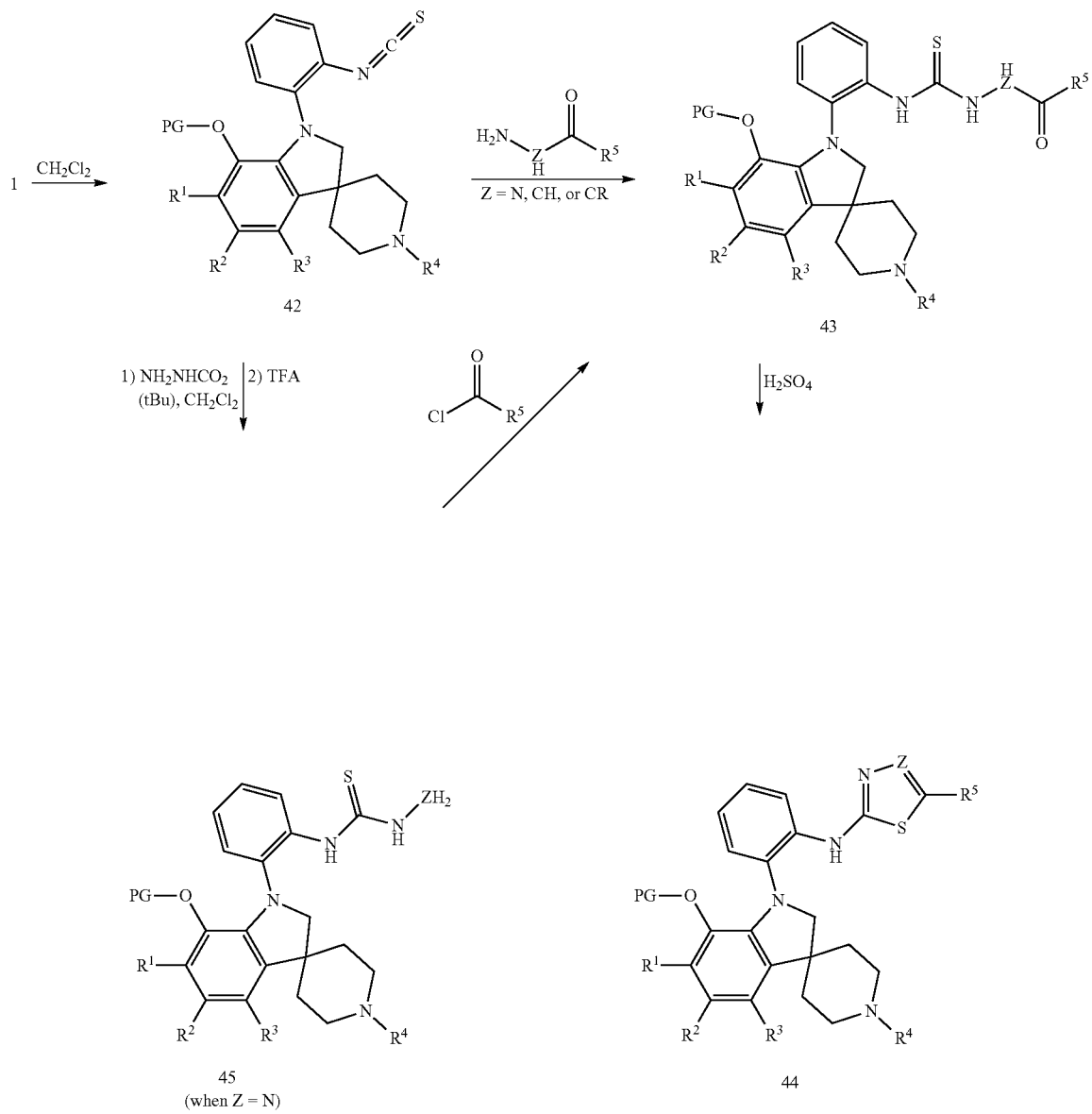

Scheme 9

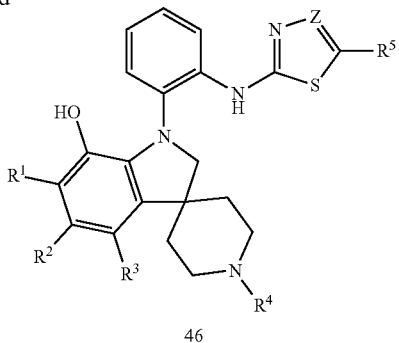

46

Scheme 10 describes the preparation of compounds of the present invention from functional intermediates 42. Treatment of intermediates 42 with amidines in a solvent such as dimethylformamide at temperatures between 70 to 120° C. provides intermediates 47. Treatment of intermediates 47 with DEAD (M. Furukawa et al., *Synthesis*, 1020-1023 (1990)), or an equivalent reagent, in a solvent such as ethanol or acetonitrile at temperatures between 0 to 70° C. provides intermediates 48. Amidines are commercially available or can be prepared by methods known to one skilled in the art of synthetic chemistry (such as described in Anbazhagam, M. et al., *Synthesis*, 2467-2469 (2003)). The protective group then can be removed following the procedure described in Scheme 8 to give the compounds of the invention 49.

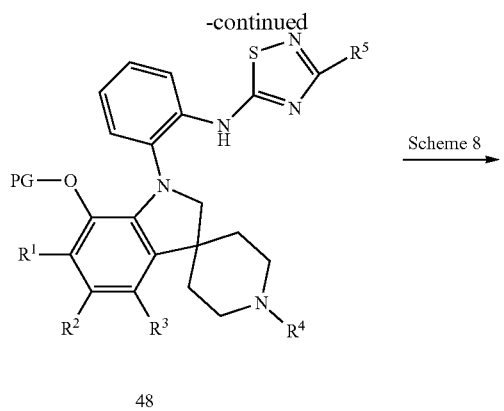

48

Scheme 10

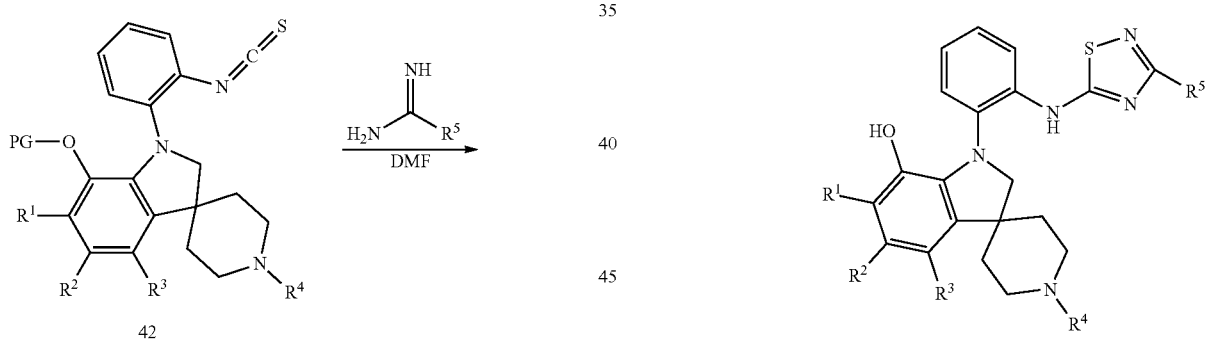

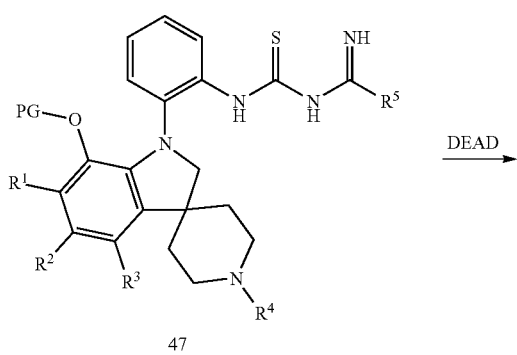

49

Scheme 11 describes the preparation of compounds of the present invention from functionalized intermediates 42. Treatment of ketones or aldehydes with a base such as sodium hydride in a solvent such as dimethylformamide at temperatures between −78 to 20° C. with subsequent addition of isothiocyanates 42 gives intermediates 50. Treatment of 50 with a base such as sodium hydride followed by treatment with an alkylating agent such as methyliodide in a solvent such as THF at temperatures between −78 to 70° C. affords intermediates 51. Treatment of intermediates of 51 with hydroxylamine in a solvent such as dimethylformamide at temperatures between −78 to 70° C. provides intermediates 53. The protective group then can be removed following the procedure described in Scheme 8 to give the compounds of the invention 54.

Scheme 11

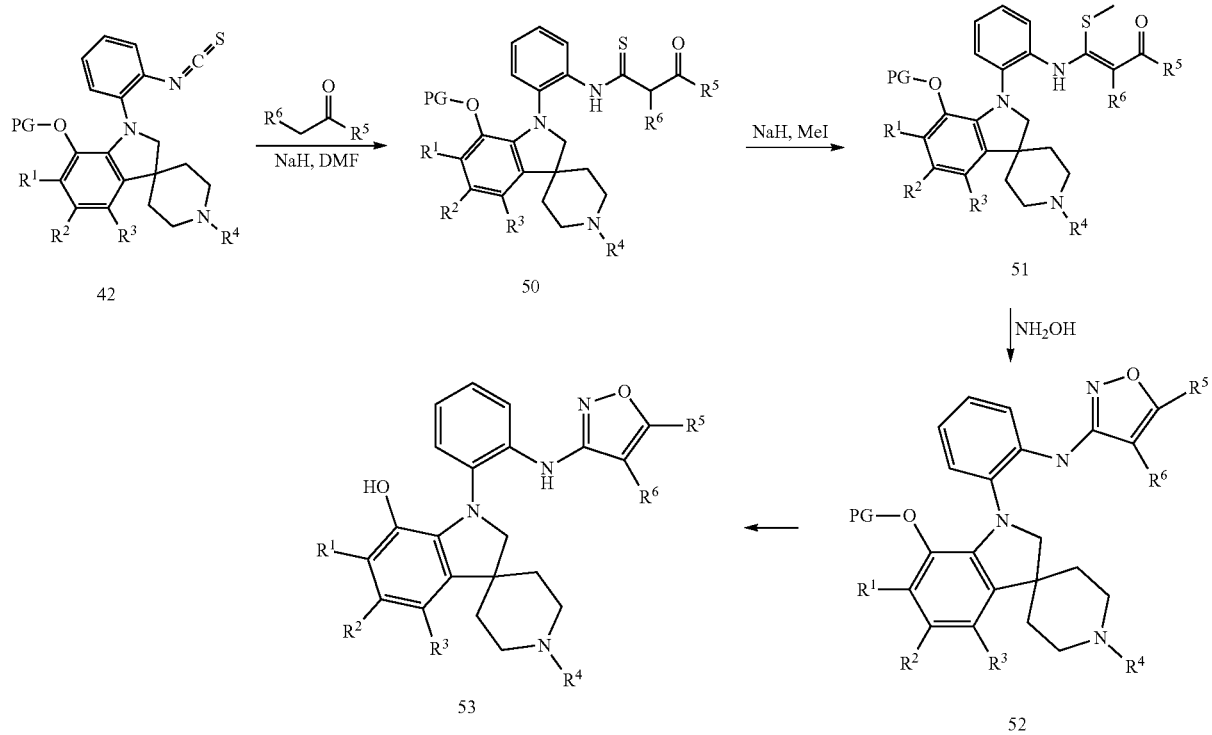

Subsequently, Scheme 12 illustrates that the trifluoromethyl group in 54 can be hydrolyzed in aqueous NaOH in the presence of variety of nucleophiles such as NH—R, SH—R, OH—R, to form esters 55, or nitriles 56 (for a general procedure, see *Organic Letters,* 13:1804-1807 (2011)).

Scheme 12

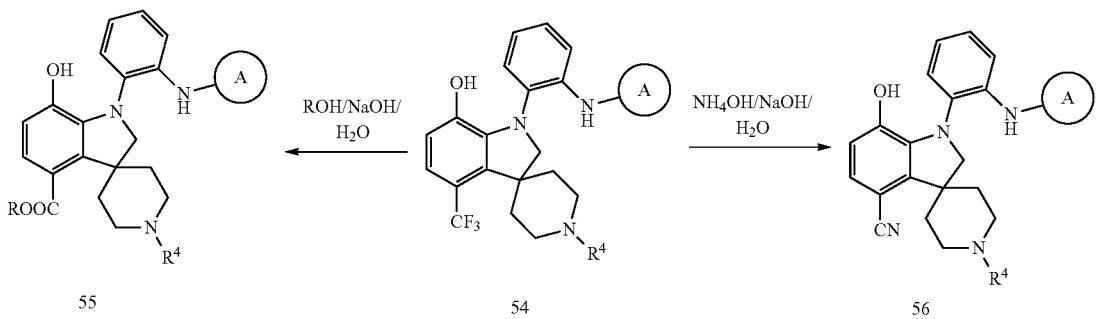

General Methods

The following methods were used in the exemplified Examples, except where noted otherwise.

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV 220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $NH_4OAc$; B: 10% water, 89.9% methanol, 0.1% $NH_4OAc$, UV 220 nm). Purification of intermediates and final products was carried out via either normal or reverse phase chromatography. Normal phase chromatography was carried out using prepacked $SiO_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Axia Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). Alternatively, reverse phase preparative HPLC was carried out using a VARIAN® ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm). LCMS chromatograms were obtained on a Shimadzu HPLC system running Discovery VP software, coupled with a Waters ZQ mass spectrometer running MassLynx version 3.5 software using:

Method A: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5u C18 (4.5×30 mm). Flow rate was 4 ml/min. and UV detection was set to 220 nm. The LC column was maintained at room temperature.

Method B: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (2.0×30 mm). Flow rate was 1 ml/min. and UV detection was set to 220 nm. The LC column was maintained at room temperature.

Method C: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 3u C18(2) (4.5×30 mm). Flow rate was 5 ml/min. and UV detection was set to 220 nm. The LC column was maintained at room temperature.

Method D: 30-95% Acetonitrile in H$_2$O with 0.1% TFA in 8 min run, Waters Xbridge 4.6×50 mm 5 um C18, flow rate 1.2 mL/min and UV detection was set to 220 nm. The LC column was maintained at room temperature.

Method E: 10-95% Methanol in water, 0.1% TFA in a 10 min run, PHENOMENEX® Onyx Monolithic 4.6×100 mm 5 um C18, flow rate 2.0 mL/mL and UV detection was set to 220 nm. The LC column was maintained at room temperature.

Method F: 5-95% Acetonitrile in water, 10 mM of modifier in 6 min run, Waters Xbridge 2.1×50 mm 5 um C18, flow rate 1.0 mL/min and UV detection was set to 220 nm. The LC column was maintained at room temperature.

In addition, the following orthogonal HPLC conditions were used to check the purity of the compounds:

Method A: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 um (4.6×150 mm). Flow rate was 2 ml/min. and UV detection was set to 220 nm. The LC column was maintained at room temperature.

Method B: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5 um (4.6×150 mm). Flow rate was 2 ml/min. and UV detection was set to 220 nm. The LC column was maintained at room temperature.

III. Biology

The compounds of the present invention are anti-platelet agents and thus are useful to maintain the fluidity of blood. Additionally, compounds of the present invention are useful for the treatment or prophylaxis of platelet-associated disorders. As used herein, the term "platelet-associated disorder" refers to any disorder which may be prevented, partially alleviated or cured by the administration of an anti-platelet agent. Thus, the compounds of the present invention are useful in the treatment or prevention of various platelet associated disorders including: Thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequences of surgery, interventional cardiology or immobility; thromboembolic consequences of medication (such as oral contraceptives, hormone replacement and heparin); thrombotic consequences of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastasis and tumor implantation; diabetic complications including retinopathy, nephropathy and neuropathy; inflammation; ischemia (such as that resulting from vascular occlusion, cerebral infarction, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously).

In addition to acting as anti-platelet agents, the compounds of the present invention may also find utility in a variety of other settings including as inhibitors of bone resorption such as encountered in various osteoporotic conditions, as inhibitors of insulin secretion in conditions of hyperinsulinemia, as vasoconstrictive agents such as those used in cases of septic or hypovolemic shock, as inhibitors of smooth muscle relaxation such for the treatment of incontinence or in other cases where inhibition of sympathetic never transmission would be of therapeutic benefit such as nociception or neuronal tissue regeneration. These and many other potential utilities for P2Y$_1$ antagonists have been recently reviewed (Burnstock, G. et al., *J. Pharm. Exp. Ther.*, 295:862-869 (2000)) and are suggested therein.

Compounds of the present invention may additionally be useful as diagnostic agents and adjuncts. For example, the present compounds may be useful in maintaining the reactivity of fractionated whole blood containing platelets such as required for analytical and biological testing or transfusions. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

It is also desirable and preferable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-platelet agent, e.g., a P2Y1 antagonist. Exemplary subjects include human beings of any age with risk factors for platelet associated disorders. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

P2Y$_1$ Assays

Binding Assay A

A membrane binding assay was used to identify inhibitors of [$^{33}$P] 2MeS-ADP binding to cloned human P2Y$_1$ receptors. The cDNA clone for human P2Y$_1$ was obtained from Incyte Pharmaceuticals and its sequence confirmed by established techniques (for a compendium of techniques used see Ausubel, F. et al. *Current Protocols in Molecular Biology*, John Wiley and Sons, NY, N.Y. (1995)). The essential coding sequences were subcloned into pCDNA 3.1 (Invitrogen) to produce a P2Y$_1$ expression construct. This construct was then transfected into the human embryonic kidney cell line HEK-293 and stable transfectants selected in GENETICIN® (G418 sulfate; Life Technologies). Several lines were screened for binding activity and one (HEK293 #49) selected for further characterization. Membranes were prepared by growing HEK293 #49 in 150 mm dishes in DMEM/10% FBS in the presence of 1 mg/ml G418 until cells were 80-90% confluent. Plates were then washed with cold (4° C.) D-PBS twice and cells harvested by scraping into 10 mL D-PBS. Cells were pelleted by centrifugation (1,000 g, 10 min, 4° C.) and the resulting pellet resuspended in Lysis Buffer (10 mM Tris (7.4), 5 mM MgCl$_2$ containing Complete protease inhibitor cocktail (Roche Cat #1873580) as recommended by the manufacturer). The suspension was then homogenized in a Dounce homogenizer (10-15 strokes; B pestle, on ice) and the homogenate spun at 1,000 g, 4° C., 5 min to pellet large debris. The supernatant was centrifuged at 150,000 g, 4° C., for 1 hour and the resulting membrane pellet resuspended in 0.5-1 mL of Buffer B (15 mM HEPES (7.4), 145 mM NaCl, 0.1 mM MgCl$_2$, 5 mM EDTA, 5 mM KCl) and stored at -70° C. until used.

Binding reactions were performed in WGA FlashPlates (PerkinElmer Life Sciences, Cat # SMP105A) in a volume of 200 µL containing ~45 fmol of P2Y$_1$ receptor (5 µg of total protein), 0.5 nM [$^{33}$P] 2MeS-ADP (PerkinElmer; 2,000 Ci/mmol), and various concentrations of the test compound (usually between 50 µM and 10 pM) in Buffer B containing 1% DMSO. Reactions were allowed to proceed to completion at room temperature for 1 hour and then the aqueous solution aspirated. Plates were sealed and the residual [$^{33}$P] bound to the plate determined by scintillation counting. Dose-response curves (IC$_{50}$) were fit by non-linear regression (XLFit, ID Business Solutions Ltd.) and binding constants ($K_i$) calculated using the Cheng-Prusoff relationship ($K_i$=IC$_{50}$/(1+L/$K_d$) in which a $K_d$ for 2MeS-ADP to the P2Y$_1$ receptor was determined to be 1.4 nM.

Binding Assay B—Scintillation Proximity Assay (SPA) for P2Y$_1$ Binding

A SPA membrane binding assay was used to identify inhibitors of [$^{33}$P] 2MeS-ADP binding to cloned human P2Y$_1$ receptors (The P2Y$_1$ receptor membranes were provided by Biology and the cloning of the receptor and P2Y$_1$ receptor membrane preparation is same as described by Biology). Binding reactions were performed in 384-well OptiPlates (PerkinElmer Life Sciences, Cat #6007299) in a volume of 50 µL containing ~15 fmol of P2Y$_1$ receptor (1.7 µg of total protein), 0.3 nM [$^{33}$P] 2MeS-ADP (PerkinElmer; 2,000 Ci/mmol), various concentrations of the test compound (usually between 10 µM and 160 pM) in Buffer B containing 1% DMSO in assay buffer (15 mM, HEPES, 145 mM potassium chloride, 5 mM sodium Chloride, 5 mM EDTA, 0.1 mM MgCl$_2$, pH 7.4) and 100 µg of SPA bead (WGA polystyrene Image beads, #RPNQ 0260V, Amersham). Reactions were allowed to proceed to completion at room temperature for 1 hour followed by centrifugation of the plate for 5 min. About 40 μL of the aqueous solution was aspirated. Plates were sealed and the [$^{33}$P] 2MeS-ADP bound to the P2Y$_1$ receptor membranes that were bound to the SPA bead were determined in a Gen 4 LEADSEEKER$^{SM}$ (Amersham) Image Reader. Dose-response curves (IC$_{50}$) were fit by non-linear regression (Toolset an in house data processing program) and binding constants (K$_i$) calculated using the Cheng-Prusoff relationship (K$_i$=IC$_{50}$/(1+L/K$_d$) in which a K$_d$ for 2MeS-ADP to the P2Y$_1$ receptor was determined to be 1.4 nM.

ADP Induced Platelet Aggregation Assay

The ability of P2Y$_1$ antagonists covered in the present invention to inhibit platelet aggregation induced by 10 μM ADP was tested using human platelet rich plasma (PRP) as described in *Platelet Protocols: Research and Clinical Laboratory Procedures* (White, M. M. et al., Academic Press (1999)). Human blood was collected in 30 μM (final concentration in blood) argatroban (GSK) as the anticoagulant at a ratio of 1 ml per 9 ml of blood. The PRP was isolated by centrifugation at 170 g for 12 minutes. The platelet poor plasma (PPP) was used as the blank for optical aggregometry. Compounds of the present invention in DMSO solution was preincubated with 250 μl PRP at 37° C. for 1 minute with stirring speed of 1000 rpm. Aggregation was initiated by addition of 2.5 μl of 1 mM ADP (Chrono-log, Havertown, Pa.) for a final ADP concentration of 10 uM. Platelet aggregation was monitored using Optical Aggregometer (Chrono-log, Havertown, Pa.) and the area under the curve (AUC) at 5 minute was measured. IC$_{50}$ was calculated using vehicle control as 0% inhibition.

The effectiveness of compounds of the present invention as antithrombotic agents and can be determined using relevant in vivo thrombosis models, including in vivo rat FeCl$_2$-induced carotid artery thrombosis, in vivo rabbit electrically-induced carotid artery thrombosis, and in vivo rabbit arteriovenous shunt thrombosis models. The potential of compounds of the present invention to have an undesirable bleeding liability can be determined using relevant in vivo rat models of cuticle and mesenteric bleeding time or in vivo rabbit cuticle bleeding model. An ideal compound from the present invention will demonstrate strong antithrombotic activity at doses that minimize the bleeding liability.

In Vivo FeCl$_2$-Induced Carotid Artery Thrombosis (FeAT) Model

The FeAT model described by Schumacher et al. (*J. Pharmacol. Exp. Ther.*, 322:1-9 (2007)) can be used in this study. SPRAGUE DAWLEY® rats (350 to 450 g) are anesthetized with Na-pentobarbital (50 mg/kg i.p.) and the trachea is intubated with polyethylene-205 tubing to ensure airway patency. Temperature is maintained with a warming table and heat lamp. A polyethylene-50 catheter is inserted into the left carotid artery to obtain blood samples for measuring ex vivo platelet aggregation responses to ADP and measuring drug concentration. The right carotid artery is exposed and fitted with transit time doppler probe attached to a T206 flowmeter (Transonic Systems Inc., Ithaca, N.Y.). A piece of parafilm "M" (American National Can, Greenwich, Conn.) is inserted under the vessel and, following baseline flow measurements, a 2 mm by 5 mm strip of filter paper saturated with a 50% solution of FeCl$_2$ is placed on top of the artery for 10 min. The carotid artery is dissected free 60 min after filter paper application and opened lengthwise to expose the thrombus, which is removed, blotted dry and weighed on an AE50 balance (Mettler, Toledo, Ind.). Carotid blood flow is monitored continuously on a TA4000 physiologic recorder (Gould, Cleveland, Ohio). Integrated blood flow is determined as an area under the curve and normalized as percent of baseline (0 min) flow over 60 min to provide a measure of average blood flow over the duration of thrombus formation.

In Vivo Rabbit Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i. v., i. p., s. c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The ED$_{50}$ (dose that increased average carotid blood flow over 90 min to 50% of the control) of compounds are estimated by a nonlinear least square regression program using the Hill sigmoid E equation (DeltaGraph; SPSS Inc., Chicago, Ill.).

In Vivo Rabbit Arterio-Venous (AV) Shunt Thrombosis Model

The rabbit AV shunt model, described by Wong et al. (Wong, P. C. et al., *J. Pharmacol. Exp. Ther.*, 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i. v., i. p., s. c., or orally) prior to the opening of the AV shunt. The percentage inhibition of thrombus formation is determined for each treatment group. The ID$_{50}$ values (dose which produces 50% inhibition of thrombus formation) are estimated by a nonlinear least square regression program using the Hill sigmoid E equation (DeltaGraph; SPSS Inc., Chicago, Ill.).

In Vivo Rat Cuticle Bleeding Time (CBT) and Mesenteric Bleeding Time (MBT) Model The CBT and MBT models described by Schumacher et al. (*J. Pharmacol. Exp. Ther.*, 322:1-9 (2007)) can be used in this study. SPRAGUE DAWLEY® rats (350 to 450 g) are anesthetized with Na-pentobarbital (50 mg/kg i.p.) and the trachea is intubated with polyethylene-205 tubing to ensure airway patency. Temperature is maintained with a warming table and heat lamp. A polyethylene-50 catheter is inserted into the left carotid artery to obtain blood samples for measuring ex vivo platelet aggregation responses to ADP.

For the MBT the abdomen is opened via a midline incision and the small intestine is exteriorized. The jejunum is exposed, held in place with clamps and superfused with Ringer's solution maintained at 37° C. Small arteries that branch perpendicular to the mesenteric artery and course over the surface of the jejunum are observed through an SZH10 stereomicroscope (Olympus Corp., Lake Success, N.Y.). These vessels are punctured with a 30-gauge hypodermic needle, and the time in sec from puncturing until bleeding stopped and remained stopped for 30 sec is recorded. The maximum bleeding time recorded is 10 min and 3 to 5 replicate bleed times are determined.

For the CBT toenails are cut with a single edged razor blade at the location where the quick meets the nail. The cuticle is immediately superfused with Ringer's solution maintained at 37° C., and the time until bleeding stopped and remained stopped for 30 sec is recorded. The maximum bleeding time recorded is 15 min. Three replicate bleeding times are determined on the hind paw.

In Vivo Rabbit Cuticle Bleeding Time Model

The rabbit cuticle bleeding time model, described by Wong et al. (Wong, P. C. et al., *J. Pharmacol. Exp. Ther.*, 303:993-1000 (2000)), can be used in this study. Male rabbits were anesthetized with ketamine (50 mg/kg+50 mg/kg/h IM) and xylazine (10 mg/kg+10 mg/kg/h IM). These anesthetics are supplemented as needed, and their hind paws were shaved. A standard cut was made at the apex of the cuticle with a razor blade. Blood was allowed to flow freely by keeping the bleeding site in contact with 37° C. warm Lactated Ringer's solution. Bleeding time was defined as the time after transection when bleeding was ceased. It was measured by averaging the bleeding time of three nail cuticles in the control period and at 60 min of the treatment period. Compound or vehicle was infused i.v. 1 h before the cuticle bleeding and continuously during the bleeding time measurement period.

Comparator Compounds

The following comparator compounds and their preparations are disclosed in U.S. Patent Publication No. 2006/0293281 A1:

| Comparator No. (Example No. in US 2006/ 0293281 A1) | Structure |
|---|---|
| Comparator 1 (Example 19 in US 2006/ 0293281 A1) | 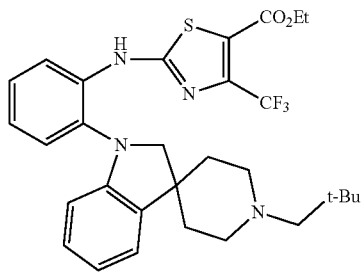 [SMILES: CCOC(=O)c1sc(Nc2ccccc2N2CC3(CCN(CC(C)(C)C)CC3)c3ccccc32)nc1C(F)(F)F] |
| Comparator 3 (Example 20 in US 2006/ 0293281 A1) | 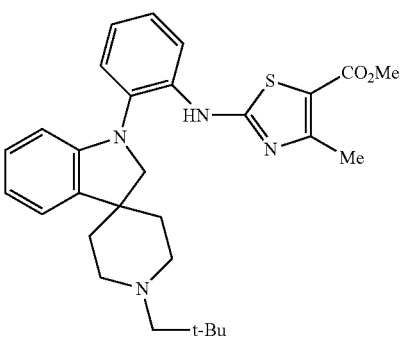 [SMILES: COC(=O)c1sc(Nc2ccccc2N2CC3(CCN(CC(C)(C)C)CC3)c3ccccc32)nc1C] |
| Comparator 3 (Example 22 in US 2006/ 0293281 A1) | 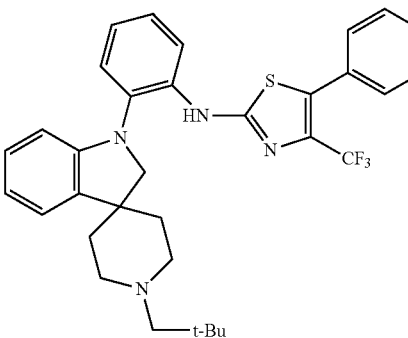 |
| Comparator 4 (Example 23 in US 2006/ 0293281 A1) | 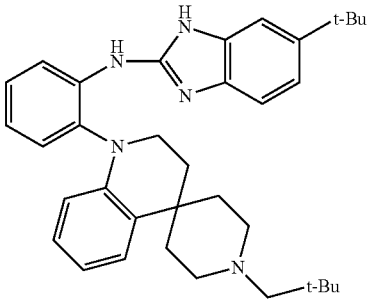 |

The following representative in vitro biological data was measured in a binding assay for the Comparator Compound and the exemplified examples herein:

TABLE 1

| Example No. | P2Y$_1$ K$_i$ (nM) using binding assay B | PA IC$_{50}$ (µM) @ 10 µM ADP |
|---|---|---|
| Comparator 1 | 258.8* | >40 |
| Comparator 2 | 6.3* | >40 |
| Comparator 3 | 18* | >40 |
| Comparator 4 | 7.9* | >>40 |
| 1 | 10 | 1.0 |
| 2 | 26 | 0.9 |
| 3 | 16 | 0.5 |
| 4 | 15 | 2.2 |
| 5 | 12 | 1.6 |
| 6 | 11 | 2.3 |
| 7 | 3.3* | 2.7 |
| 8 | 7 | 1.5 |
| 9 | 24.3* | 8.5 |
| 10 | 40.2 | 11.4 |
| 11 | 16 | 3.7 |
| 12 | 6.5* | 0.9 |

TABLE 1-continued

| Example No. | P2Y$_1$ K$_i$ (nM) using binding assay B | PA IC$_{50}$ (µM) @ 10 µM ADP |
|---|---|---|
| 13 | 6.6* | 0.9 |
| 14 | 155.4* | 23.0 |
| 15 | 5.7* | 1.6 |
| 16 | 66 | 17.7 |
| 17 | 48 | 7.2 |
| 18 | 33 | 1.8 |
| 19 | 28 | 10.7 |
| 20 | 16 | 2.6 |
| 21 | 13 | 1.3 |
| 22 | 22 | 4.0 |
| 23 | 19 | 3.4 |
| 24 | 28 | 4.5 |
| 25 | 19 | 3.7 |
| 26 | 13 | 0.9 |
| 27 | 24 | 3.2 |
| 28 | 6.8 | 5.8 |
| 29 | 23 | 2.4 |
| 30 | 5 | 2.0 |
| 31 | 6 | 4.2 |
| 32 | 69 | 15.6 |
| 33 | 23 | 9.2 |
| 34 | 37 | 9.9 |
| 35 | 6 | 5.4 |
| 36 | 8 | 2.1 |
| 37 | 60 | 9.9 |
| 38 | 66 | 9.0 |
| 39 | 9 | 4.9 |
| 40 | 19 | 1.0 |
| 41 | 21 | 20.3 |
| 42 | 22 | 22.8 |
| 43 | 8 | 3.1 |
| 44 | 8 | 0.8 |
| 45 | 3 | 3.5 |
| 46 | 10 | 1.1 |

*Using binding assay A.

The platelet aggregation assay measures the in vitro antiplatelet activity of a compound in platelet rich plasma. The assay is sensitive to plasma protein binding, and is believed to be a better predictor of actual in vivo activity. Surprisingly, it was discovered that the compounds of the present invention are unexpectedly significantly more active in the platelet aggregation assay than those exemplified in U.S. Patent Publication No. 2006/0293281 A1.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing.

For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., other anti-platelet agents or other pharmaceutically active material. Additionally, the present compounds may be used in combination with one or more of various other therapeutic agents, including:

anti-arrhythmic agents; anti-hypertensive agents; anti-thrombotic and/or anti-thrombolytic agents; calcium channel blockers (L-type and T-type); cardiac glycosides; diuretics, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); antiosteoporosis agents; hormone replacement therapies; oral contraceptives; anticoagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving $P2Y_1$ or anti-platelet activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Intermediate 1

1-Pivaloylpiperidine-4-carbaldehyde

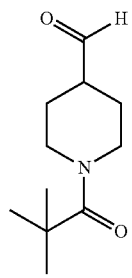

Intermediate 1A 1-(4-(Hydroxymethyl)piperidin-1-yl)-2,2-dimethyl-propan-1-one

In a 500-mL round bottomed flask, to piperidin-4-yl methanol (20.0 g, 174 mmol) in 180 mL of dichloroethane was added triethylamine (24.2 mL, 174 mmol) followed by pivaloyl chloride (21.4 mL, 174 mmol). The mixture was stirred at 23° C. for 4 hours, then filtered and the filtrate was concentrated in vacuo. The residue was dissolved in EtOAc, washed with sat'd NH₄Cl (2×), water, brine, dried over Na₂SO₄, filtered and concentrated in vacuo giving 28 g of Intermediate 1A. ¹H-NMR (DMSO-d₆) δ ppm 4.47 (t, J=5.31 Hz, 1H), 4.25 (d, J=12.88 Hz, 2H), 3.23 (t, J=5.68 Hz, 2H), 2.71 (t, J=12.38 Hz, 2H), 1.56-1.68 (m, 3H), 1.16 (s, 9H), 0.96 (ddd, J=24.00, 12.25, 3.92 Hz, 2H); LCMS (ESI) m/z 200 (M+H)⁺, RT=0.48 min (Method B).

Intermediate 1

1-Pivaloylpiperidine-4-carbaldehyde

A 1000-mL oven-dried flask capped with a rubber septum was evacuated and backfilled with argon. The flask was charged with oxalyl chloride (17.4 mL, 203 mmol) in 320 mL of DCM. At −78° C., a solution of DMSO (28.9 mL, 406 mmol) in 50 mL DCM was added dropwise. After 30 min, Intermediate 1A (27.0 g, 135 mmol) in 100 mL of DCM was added dropwise. After 30 min, triethylamine (75.5 mL, 542 mmol) was added, stirred for 30 min at −78° C. The reaction was poured into water, extracted with DCM (3×). Combined organic layers were washed with water (3×300 mL), dried over Na₂SO₄, filtered and concentrated in vacuo providing 24.2 g (yield: 91%) of Intermediate 1. ¹H-NMR (DMSO-d₆) δ ppm 9.58 (s, 1H), 4.25 (d, J=10.36 Hz, 1H), 4.06 (ddd, J=13.52, 3.66, 3.54 Hz, 2H), 2.93-3.04 (m, 1H), 2.65-2.76 (m, 1H), 1.78-1.86 (m, 1H), 1.65 (d, J=12.38 Hz, 1H), 1.30-1.41 (m, 2H), 1.16 (s, 9H); LCMS (ESI) m/z 198 (M+H)⁺, RT=0.518 min (Method B).

Alternatively, Intermediate 1 was prepared in a large-scale synthesis as following:

Intermediate 1B

Ethyl 1-pivaloylpiperidine-4-carboxylate

A solution of ethyl isonipecolate (375 g, 2.39 mol) in dry THF stirred at 0° C. under nitrogen atmosphere was added triethylamine (396 mL, 2.87 mol) dropwise followed by the addition of pivaloyl chloride (312 mL, 2.51 mol). The mixture was allowed to attain rt under stirring overnight. On completion of the reaction, the solid mass obtained was filtered and the filtrate was concentrated. The residue was dissolved in ethyl acetate and washed with water, brine, dried over anhydrous sodium sulfate and concentrated under reduced pressure to give the crude Intermediate 1B (550 g). GC: 95.9% purity, RT=18.25 min (Column DB-624, 30×0.53 mm×3 um, Constant flow, flow rate=8.0 mL/min, Inlet temp.=150° C., Detector temp=250° C. Split ratio: 10:1, Oven temp.: Initial=50° C. for 2 min, Ramp: 15° C./min, Final=220° C. for 10 min). GCMS 241 (M⁺); ¹H NMR (400 MHz, CDCl₃) δ 1.21-1.26 (t, 3H, CH₃ of the ester group), 1.28 (s, 9H, 3×CH₃ of pivaloyl), 1.65-1.68 (m, 2H), 1.90 (m, 2H), 2.45-2.65 (m, 1H), 2.97 (m, 2H), 4.16-4.19 (q, 2H, OCH₂), 4.27-4.31 (d, 2H).

Intermediate 1A

Intermediate 1B (1153 g, 4.790 mol) was taken in a mixture of ethanol and dry THF (12 L, 1:1) and cooled to 0° C. Sodium borohydride (542.5 g, 14.35 mol) was added portion wise at 0° C. and then the reaction mixture was allowed to attain rt by stirring overnight. After the completion of reaction, water was added and ethanol and THF were concentrated under reduced pressure. The concentrated mass was dissolved in ethyl acetate and washed with water, brine, dried over anhydrous sodium sulfate and concentrated under reduced pressure to give Intermediate 1A (890 g, yield: 93.4%). GCMS: 199 (Mt); ¹H NMR (300 MHz, CDCl₃) δ 1.28 (s, 9H, 3×CH₃ of pivaloyl), 1.76 (m, 4H), 1.80 (m, 1H), 2.05 (s, 1H, OH), 2.74-2.82 (t, 2H), 3.50 (d, 2H), 4.43-4.47 (d, 2H, CH₂OH).

Intermediate 1

The crude Intermediate 1A (890 g, 4.47 mol) was dissolved in dichloromethane (9 L), and stirred at 0° C. under nitrogen atmosphere. Dess-Martin periodinane (1.80 Kg, 4.47 mol) was added slowly and the reaction mixture was allowed to attain rt by stirring overnight. After completion of the reaction, the reaction mixture was basified to pH 11 with sodium carbonate. Water was added and the reaction mixture was filtered through CELITE®. The filtrate was concentrated and the residue was dissolved in ethyl acetate, washed with sodium carbonate solution, brine, dried over anhydrous sodium sulfate and concentrated to give the crude Intermediate 1 (700 g).

Intermediate 2

2-(4-Chloro-7-methoxy-1'-neopentylspiro[indoline-3,4'-piperidine]-1-yl)aniline

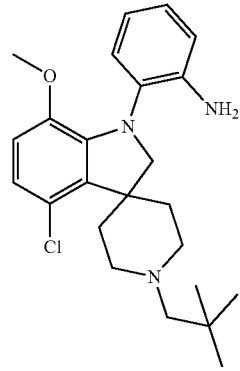 [SMILES: COc1ccc(Cl)c2c1N(c1ccccc1N)CC21CCN(CC(C)(C)C)CC1]

Intermediate 2A (5-Chloro-2-methoxyphenyl)hydrazine, HCl

To a solution of 5-chloro-2-methoxyaniline (11.0 g, 69.8 mmol) in 100 ml of 3 N HCl was added sodium nitrite (5.3 g, 77 mmol) in 25 ml of H₂O dropwise (1 mL/min) at an ice-salt bath temperature. The resulting mixture was stirred for 1 h after the addition was complete. To this solution was added tin(II) chloride dihydrate (14.5 mL, 174 mmol) in 40 mL of conc. HCl dropwise. After addition, the resulting mixture was stirred for 1 h at ice-salt bath temperature. The white solid from the mixture was filtered, and washed with cold brine (20 mL) and 2 N HCl (20 mL). The filtrate was dried under reduced pressure to yield Intermediate 2A (18.4 g, 88.0 mmol, 126% yield), which contains SnCl₂ as well as more than 1.0 equiv. HCl as a co-salt.

Intermediate 2B 1-(4-Chloro-7-methoxyspiro[indoline-3,4'-piperidine]-1'-yl)-2,2-dimethylpropan-1-one A solution of Intermediate 2A (4.0 g, 19 mmol) and 1-pivaloylpiperidine-4-carbaldehyde (3.2 g, 16 mmol) in CH₂Cl₂

(30 mL) and dioxane (15.0 mL) of 4 N HCl was stirred for 1 h at 0° C. The solution was evaporated to provide a yellow solid, which was re-dissolved in MeOH (30.0 mL). The methanolic solution of the imine was cooled down to 0° C. and sodium cyanoborohydride (2.04 g, 32.4 mmol) was added by portions over 30 min. The resulting solution was stirred for 1 h at 0° C. Reaction was quenched by adding 10 mL of 1 N HCl dropwise and the resulting solution was stirred at ambient temperature. Reaction mixture was then concentrated to provide a yellow solid, which was partitioned at 20 mL of 1 N NaOH and dichloromethane (100 mL). Aqueous layer was further extracted with EtOAc (50 mL). The combined organic layers were dried over $Na_2SO_4$ and concentrated, yielding oily residue, which was purified by flash chromatography (silica gel, eluting with EtOAc/Hexanes) to yield Intermediate 2B (1.7 g, 5.1 mmol, 31% yield) as a colorless oily solid upon concentration. LCMS (ESI) m/z 337.3 $(M+H)^+$, RT=1.52 min (Method D).

Intermediate 2C 1-(4-Chloro-7-methoxy-1-(2-nitrophenyl)spiro[indoline-3,4'-piperidine]-1'-yl)-2,2-dimethylpropan-1-one To a solution of Intermediate 2B (1.70 g, 5.05 mmol) in a degassed toluene (40 mL) was added 2-bromo-nitrobenzene (1.9 g, 9.5 mmol), $Cs_2CO_3$ (3.95 g, 12.1 mmol), BINAP (0.377 g, 0.606 mmol) and $Pd_2dba_3$ (0.185 g, 0.202 mmol), and the resulting solution was stirred for 10 min at 25° C. with Argon bubbling. The reaction mixture was sealed in microwave tube and stirred at 115° C. for 16 h. Reaction mixture was filtered and concentrated, yielding a dark oily residue, which was purified by flash chromatography (silica gel, eluting with EtOAc/Hexanes) to yield Intermediate 2C (1.8 g, 3.9 mmol, 78% yield) as a brown solid. LCMS (ESI) m/z 458.4 $(M+H)^+$, RT=2.05 min (Method D).

Intermediate 2D 1-(1-(2-Aminophenyl)-4-chloro-7-methoxyspiro [indoline-3,4'-piperidine]-1'-yl)-2,2-dimethylpropan-1-one To a solution of Intermediate 2C (1.8 g, 3.9 mmol) in ethanol (40 mL) was added zinc (0.360 mL, 39.3 mmol) and ammonium chloride (1.38 mL, 39.3 mmol) and the resulting solution was stirred for 12 h at 25° C. The reaction mixture was filtered and organic solution was concentrated to give a light brown oily residue. The crude was partitioned in EtOAc (50 mL) and brine (20 mL). Aqueous layer was extracted with EtOAc (30 mL). The combined organic solution was dried over $Na_2SO_4$ and concentrated to provide Intermediate 2D (1.6 g, 3.7 mmol, 95% yield) as light brown oil, which was subjected to the following reaction without further purification. LCMS (ESI) m/z 428.2 $(M+H)^+$, RT=1.71 min (Method D).

Intermediate 2

2-(4-Chloro-7-methoxy-1'-neopentylspiro[indoline-3,4'-piperidine]-1-yl)aniline

To a solution of Intermediate 2D (1.6 g, 3.7 mmol) in DCM (50 mL) was added RED-AL® (6.08 mL, 18.7 mmol) dropwise for 20 min and the resulting solution was stirred for 5 h at 25° C. Reaction was quenched by adding drops of aqueous $NaHCO_3$ into the reaction mixture. It was then diluted with DCM (50 mL) and washed with aqueous $NaHCO_3$ (30 mL). Organic layer was dried over $Na_2SO_4$ and concentrated in vacuo, yielding Intermediate 2 (1.2 g, 2.9 mmol, 78% yield) as oil, which was subjected to the following reaction without further purification. LCMS (ESI) m/z 414.3 $(M+H)^+$, RT=1.30 min (Method D).

Alternatively, Intermediate 2 was prepared in a large-scale synthesis as following:

Intermediate 2A

To a solution of 2-methoxy-5-chloroaniline (100 g, 0.636 mol) in 6N HCl (600 mL) was added slowly an aqueous solution of sodium nitrite (52.7 g, 0.764 mol) maintaining the temperature between −5 to 0° C. The reaction mixture was then stirred for about 1 h maintaining the temperature below 0° C. A solution of stannous chloride (362 g, 1.90 mol) in conc. HCl was added slowly at −5 to 0° C. and stirring was continued for another 1.5 h after which the reaction mixture was brought to room temperature slowly. The white solid was then filtered, washed with 2 N HCl to remove the stannous chloride, and then washed with diethyl ether and air dried to give Intermediate 2A (120 g, yield: 90.0%). $^1$H NMR (400 MHz, DMSO-$d_6$) δ 3.82 (s, 3H, $OCH_3$), 6.95-7.00 (m, 2H), 7.135-7.139 (d, 1H), 10.28 (bs, 3H, NH and $NH_2$). $^{13}$C NMR (100 MHz, DMSO-$d_6$) δ 56.48, 112.61, 114.37, 121.59, 124.75, 135.95, 146.82.

Intermediate 2B-a 1-(4-Chloro-7-methoxyspiro[indole-3,4'-piperidine]-1'-yl)-2,2-dimethylpropan-1-one To a solution of Intermediate 2A (130 g, 0.628 mol) in methanol (1.3 L) was added intermediate 1 (124 g, 0.628 mol) under nitrogen. The mixture was stirred at rt for 2.5 h. The reaction mixture was cooled to 0° C., conc. sulfuric acid (51.3 mL, 0.941 mol) was added slowly and the contents were stirred at rt overnight. The mixture was heated at 50° C. for 3 h. Methanol was evaporated under reduced pressure and the residue was dissolved in ethyl acetate. The organics were washed with diluted NaOH, followed by washing with water and then by brine. The organic layer was dried over anhydrous sodium sulfate and concentrated under reduced pressure. The crude was purified by flash chromatography using hexanes/ethyl acetate=20/80 to give the pure Intermediate 2B-a (85 g, yield: 41%). MS (ESI) m/z 335.1 $(M+H)^+$. $^1$H NMR (300 MHz, $CDCl_3$) δ 1.35 (s, 9H, 3×$CH_3$ of pivaloyl), 1.45 (d, 2H), 2.75-2.83 (m, 2H), 3.19-3.22 (t, 2H), 4.68-4.71 (d, 2H), 6.87-6.89 (d, 1H), 7.18-7.20 (d, 1H), 8.68 (s, 1H).

Intermediate 2B

To a solution of Intermediate 2B-a (33 g, 99 mmol) in dry MeOH (330 mL) at 0° C. was added sodium borohydride portion wise (3.75 g, 98.6 mmol) under nitrogen atmosphere. The reaction mixture was stirred at rt overnight under nitrogen atmosphere. After completion of the reaction, the reaction was quenched with water at rt and then concentrated under reduced pressure to remove MeOH completely. The residue was dissolved ethyl acetate, washed with water and brine. The organic layer was separated, dried over anhydrous sodium sulfate and concentrated under reduced pressure to give the crude product. The pure Intermediate 2B was obtained by crystallization from ethyl acetate (28 g, yield: 85%). MS (ESI) m/z 337.1 $(M+H)^+$. $^1$H NMR (300 MHz, DMSO-$d_6$) δ 1.21 (s, 9H, 3×$CH_3$ of pivaloyl), 1.53-1.56 (d, 2H), 2.21-2.28 (m, 2H), 2.86 (t, 2H), 3.49-3.49 (d, 2H), 3.72 (s, 3H, OCH$_3$), 4.26-4.30 (d, 2H), 5.51 (bs, 1H, NH of indoline), 6.48-6.48 (d, 1H), 6.67-6.69 (d, 1H). $^{13}$C NMR (100 MHz, DMSO-d$_6$) δ 28.53, 33.47, 38.57, 42.11, 47.52, 55.80, 56.22, 111.96, 118.39, 121.47, 130.44, 143.01, 144.02, 175.19.

Intermediate 2C

A suspension of Intermediate 2B (24 g, 71 mmol), 2-bromo nitrobenzene (21.6 g, 107 mmol), BINAP (8.88 g, 14.2 mmol), palladium acetate (1.6 g, 7.1 mmol), cesium carbonate (34.8 g, 107 mmol) in dry xylene (240 mL) was stirred under nitrogen atmosphere in a sealed tube at 130° C. for 16 h. The reaction mixture was filtered through CELITE®, washed thoroughly with MeOH and ethyl acetate, and the filtrate was concentrated under reduced pressure. The crude was purified by flash chromatography using hexanes/ethyl acetate=60:40 to give Intermediate 2C (23 g, yield: 72%). MS (ESI) m/z 458.2 (M+H)$^+$. $^1$H NMR (400 MHz, DMSO-d$_6$) δ 1.21 (s, 9H, 3×CH$_3$ of pivaloyl), 1.65-1.72 (t, 2H), 2.08-2.14 (m, 1H), 2.57-2.64 (dt, 1H), 2.81-2.87 (t, 1H), 2.94-2.30 (t, 1H), 3.40 (s, 3H, OCH$_3$), 4.15-4.18 (d, 1H), 4.24-4.35 (m, 3 H), 6.8 (s, 2H), 7.18-7.22 (m, 1H), 7.43-7.46 (dd, 1H,), 7.60-7.64 (m, 1H), 7.99-8.02 (dd, 1H).

Intermediate 2D

To a solution of Intermediate 2C (30 g, 66 mmol) in a 1:1 mixture of methanol and ethanol (600 mL), was added Raney-nickel (6 g). The resulting mixture was stirred under hydrogen for 16 h. The reaction mixture was filtered through CELITE® and washed with methanol. The filtrate was concentrated under reduced pressure to give the crude product which was purified by flash chromatography using hexanes/ethyl acetate=60:40 as the eluent to give Intermediate 2D (24 g, yield: 86%). MS (ESI) m/z 428.2 (M+H)$^+$. $^1$H NMR (400 MHz, DMSO-d$_6$) δ 1.19 (s, 9H, 3×CH$_3$ of pivaloyl), 1.53-1.57 (d, 1H), 1.71-1.75 (d, 1H), 2.25-2.33 (m, 2H), 2.72-2.86 (m, 2H), 3.19-3.27 (m, 2H), 3.41 (s, 3H, OCH$_3$), 4.21-4.33 (m, 2H), 4.90 (s, 2H, NH$_2$), 6.40-6.45 (t, 1H), 6.65-6.68 (m, 2H), 6.70-6.86 (m, 4H).

Intermediate 2

To a solution of Intermediate 2D (160 g, 0.374 mol) in dichloromethane (3.2 L) was added RED-AL® (570 ml, 65.0%, 1.87 mol) dropwise with stirring under nitrogen atmosphere over a period of 1 h. The temperature was maintained below 40° C. during the addition. The reaction mixture was then stirred at rt for 4 h. It was quenched with saturated sodium bicarbonate solution and extracted with dichloromethane. The organic layer was washed with water, brine, dried over anhydrous sodium sulfate and concentrated under reduced pressure to give the crude product. It was purified by flash chromatography using hexanes/ethyl acetate=90/10 as the eluent to give the pure Intermediate 2 (121 g, yield: 78.0%). MS (ESI) m/z 414.2 (M+H)$^+$; Orthogonal HPLC purity: 96.4% (Method A), 96.1% (Method B); $^1$H NMR (400 MHz, DMSO-d$_6$) δ 0.84 (s, 9H), 1.38-1.41 (d, 1H), 1.56-1.59 (d, 1H), 2.01 (s, 2H), 2.12-2.16 (t, 1H), 2.27-2.29 (t, 1H), 2.52-2.53 (d, 1H), 2.56-2.66 (m, 2H), 2.714-2.73 (d, 1H), 3.08-3.10 (d, 1H), 3.42 (s, 3H), 4.03-4.06 (d, 1H), 4.84 (s, 2H, NH$_2$), 6.39-6.43 (t, 1H), 6.60-6.62 (d, 1H), 6.66-6.68 (d, 1H), 6.71-6.78 (m, 2H), 6.80-6.85 (t, 1H). $^{13}$C NMR (100 MHz, DMSO-d$_6$) δ 27.57, 32.80, 34.61, 45.50, 52.43, 55.67, 63.99, 69.37, 113.65, 114.72, 115.72, 121.29, 122.67, 125.18, 133.34, 134.65, 139.99, 143.21, 145.35.

Intermediate 3

2-(7-Methoxy-1'-neopentyl-4-(trifluoromethyl)spiro[indoline-3,4'-piperidine]-1-yl)aniline

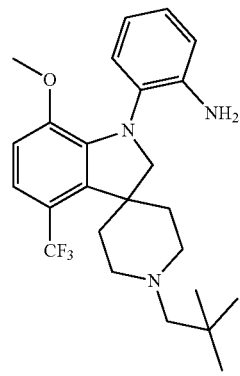 [SMILES: COc1ccc(C(F)(F)F)c2c1N(c1ccccc1N)CC21CCN(CC(C)(C)C)CC1]

Intermediate 3 was prepared following similar procedures described in Intermediate 2. LCMS (ESI) m/z 448.5 (M+H)$^+$, RT=2.43 min (Method C).

Intermediate 4

1-(1-(2-Aminophenyl)-7-(benzyloxy)-4,5-difluorospiro[indoline-3,4'-piperidine]-1'-yl)-2,2-dimethylpropan-1-one

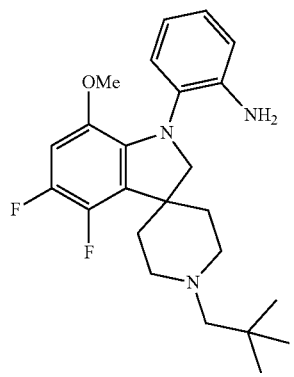 [SMILES: COc1cc(F)c(F)c2c1N(c1ccccc1N)CC21CCN(CC(C)(C)C)CC1]

Intermediate 4 was prepared following the similar procedure described in Intermediate 2. LC-MS (ESI) m/z 416.2 (M+H)+, RT=1.26 min (Method D).

Intermediate 5

2-(4,6-Difluoro-7-methoxy-1'-neopentylspiro[indoline-3,4'-piperidine]-1-yl)aniline

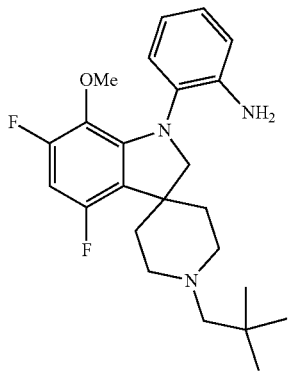 [SMILES: COc1c(F)cc(F)c2c1N(c1ccccc1N)CC21CCN(CC(C)(C)C)CC1]

Intermediate 5 was prepared following similar procedures described in Intermediate 2. LC-MS (ESI) m/z 416.2 (M+H)+, RT=1.30 min (Method D).

Intermediate 6

2-(4-Chloro-5-fluoro-7-methoxy-1'-neopentylspiro[indoline-3,4'-piperidine]-1-yl)aniline

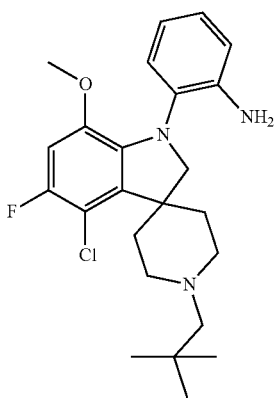 [SMILES: COc1cc(F)c(Cl)c2c1N(c1ccccc1N)CC21CCN(CC(C)(C)C)CC1]

Intermediate 6 was prepared following similar procedures described in Intermediate 2. LCMS (ESI) m/z 432.2 (M+H)+, RT=1.35 min (Method D).

Intermediate 7

2-(4-Chloro-6-fluoro-7-methoxy-1'-neopentylspiro[indoline-3,4'-piperidine]-1-yl)aniline

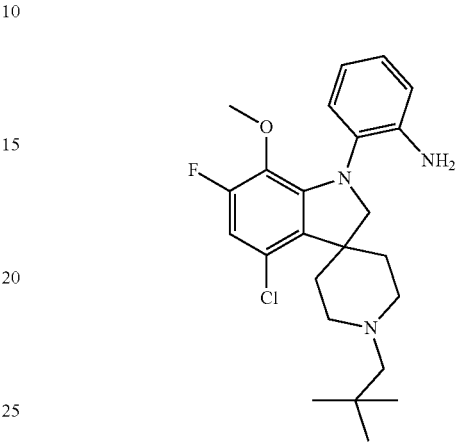

Intermediate 7 was prepared following similar procedures described in Intermediate 2. LCMS (ESI) m/z 432.2/434.2 (M+H)+, RT=1.43 min (Method D).

Example 1

1'-Neopentyl-1-(2-(5-phenyl-1,3,4-thiadiazol-2-ylamino)phenyl)-4-(trifluoromethyl)spiro[indoline-3,4'-piperidin]-7-ol

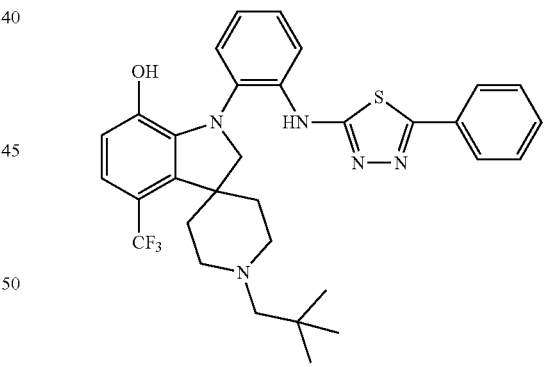

Example 1A 1-(2-Isothiocyanatophenyl)-7-methoxy-1'-neopentyl-4-(trifluoromethyl)spiro[indoline-3,4'-piperidine]

To a solution of Intermediate 3 (1.29 g, 2.88 mmol) in dichloromethane (10 mL) was added 1,1'-thiocarbonyldipyridin-2(1H)-one (0.669 g, 2.88 mmol) in dichloromethane (15 mL) dropwise over 20 min. The reaction temperature was stirred at 23° C. for 5 h. The reaction was concentrated and purified by flash chromatography (silica gel, eluting with EtOAc/Hexanes) to give Example 1A as a white solid (1.36 g, 2.78 mmol, 96.0% yield). LC-MS ESI 490.5 (M+H) (Method A, RT=3.26 min). $^1$H NMR (400 MHz, chloroform-d) δ ppm 7.23 (1H, d, J=7.20 Hz), 7.20 (1H, dd, J=7.83, 1.52 Hz), 7.12 (1H, t, J=7.20 Hz), 7.03 (1H, t, J=7.33 Hz), 6.88 (1H, d, J=7.83 Hz), 6.76 (1H, d, J=8.59 Hz), 4.08 (1H, d, J=10.11 Hz), 3.69 (1H, d, J=10.11 Hz), 3.62 (3H, s), 2.76 (1H, s), 2.68 (1H, s), 2.44 (1H, d, J=1.77 Hz), 2.41 (1H, s), 2.03 (2H, s), 1.68 (1H, s), 1.58 (1H, s), 1.41 (1H, d, J=9.09 Hz), 1.23-1.28 (1H, m), 0.86 (9H, s).

Example 1B

N-(2-(7-Methoxy-1'-neopentyl-4-(trifluoromethyl) spiro[indoline-3,4'-piperidine]-1-yl)phenyl)-5-phenyl-1,3,4-thiadiazol-2-amine A solution of Example 1A (104 mg, 0.212 mmol) and benzohydrazide (28.9 mg, 0.212 mmol) in dichloromethane (1 mL) were stirred at 23° C. for 18 h. Conc. sulfuric acid (0.226 mL, 4.25 mmol) was added dropwise. After 30 min, the reaction mixture was quenched with saturated NaHCO$_3$, extracted with dichloromethane (2 mL×3), concentrated, and purified by flash chromatography (silica gel, eluting with EtOAc/Hexanes) to give Example 1B as a white solid (70.0 mg, 0.115 mmol, 54.2% yield). LC-MS ESI 608.6 (M+H) (Method A, RT=3.29 min). $^1$H NMR (400 MHz, chloroform-d) δ ppm 7.90 (1H, d, J=8.35 Hz), 7.84-7.87 (2H, m), 7.41-7.45 (3H, m), 7.21-7.26 (2H, m), 6.99 (2H, d, J=3.95 Hz), 6.72 (1H, d, J=8.79 Hz), 4.03 (1H, d, J=10.11 Hz), 3.51 (3H, s), 3.32 (1H, d, J=10.11 Hz), 2.77 (1H, s), 2.72 (1H, s), 2.60 (2H, t, J=12.96 Hz), 2.32 (2H, t, J=12.30 Hz), 2.07 (2H, s), 1.65 (1H, d, J=10.55 Hz), 1.58 (1H, d, J=13.18 Hz), 0.87 (9H, s).

Example 1

To Example 1B (70 mg, 0.115 mmol) and tetrabutylammonium iodide (255 mg, 0.691 mmol) in dry DCM (1 mL) under argon at −50° C., boron trichloride in 1 N dichloromethane solution (0.576 mL, 0.576 mmol) was added dropwise. The stirring mixture was stirred from −50 to −10° C. over 1 h, and then dry ice bath was removed. The mixture was stirred at 23° C. for 18 h. At 0° C., water (0.5 mL) was added dropwise. The reaction mixture was extracted with dichloromethane (2 mL×3). The organic layers was combined, concentrated, and purified by prep HPLC (9-54% acetonitrile in water over 20 min, 0.1% TFA as modifier) twice to give Example 1 as a white solid (9.30 mg, 0.016 mmol, 13.60% yield). LC-MS ESI 594.6 (M+H) (Method A, RT=2.91 min). $^1$H NMR (400 MHz, methanol-d$_3$) δ ppm 7.89 (1H, d, J=7.70 Hz), 7.80 (2H, dd, J=6.32, 3.02 Hz), 7.45-7.49 (3H, m), 7.22 (1H, t, J=6.87 Hz), 7.16 (1H, t, J=7.97 Hz), 7.03-7.12 (2H, m), 6.78 (1H, t, J=8.52 Hz), 4.14 (1H, d, J=10.44 Hz), 3.52-3.62 (2H, m), 3.25-3.36 (3H, m), 3.20 (1H, s), 3.07-3.17 (1H, m), 2.97 (1H, s), 2.75 (1H, td, J=14.02, 4.40 Hz), 2.58 (1H, td, J=14.15, 4.12 Hz), 1.87-1.96 (1H, m), 1.06-1.12 (9H, m). Orthogonal HPLC purity: RT=8.17 min, 100% (Method A); RT=6.79 min, 100% (Method B).

Examples 2-11 were prepared following the procedure described for Example 1 with corresponding hydrazides.

Example 2

1-(2-(5-(4-tert-Butylphenyl)-1,3,4-thiadiazol-2-ylamino)phenyl)-1'-neopentyl-4-(trifluoromethyl) spiro[indoline-3,4'-piperidin]-7-ol

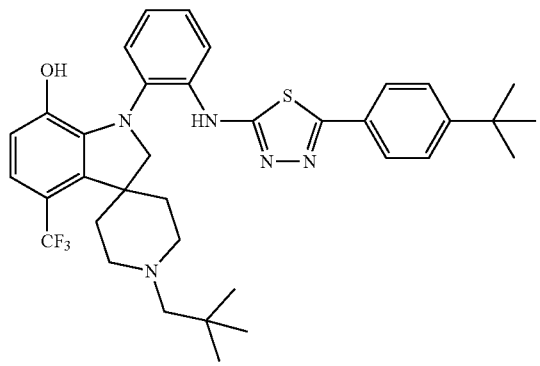 [SMILES: CC(C)(C)CN1CCC2(CC1)CN(c1ccccc1Nc1nnc(-c3ccc(C(C)(C)C)cc3)s1)c1c(O)ccc(C(F)(F)F)c12]

LC-MS ESI 650.4 (M+H) (Method A, RT=3.61 min). $^1$H NMR (400 MHz, chloroform-d) δ ppm 7.68 (2H, d, J=7.91 Hz), 7.52-7.59 (1H, m), 7.42 (2H, d, J=8.35 Hz), 7.15 (1H, s), 7.13 (1H, d, J=3.95 Hz), 7.04 (1H, s), 6.98 (1H, s), 6.85 (1H, s), 3.68 (1H, d, J=7.47 Hz), 3.21-3.53 (1H, m), 2.63 (2H, d, J=7.47 Hz), 2.27-2.39 (4H, m), 1.99-2.10 (2H, m), 1.43 (1H, d, J=12.74 Hz), 1.32 (10H, s), 0.85 (9H, s). Orthogonal HPLC purity: RT=9.17 min, 93% (Method A); RT=7.97 min, 93% (Method B).

Example 3

1'-Neopentyl-4-(trifluoromethyl)-1-(2-(5-(4-(trifluoromethyl)phenyl)-1,3,4-thiadiazol-2-ylamino)phenyl)spiro[indoline-3,4'-piperidin]-7-ol

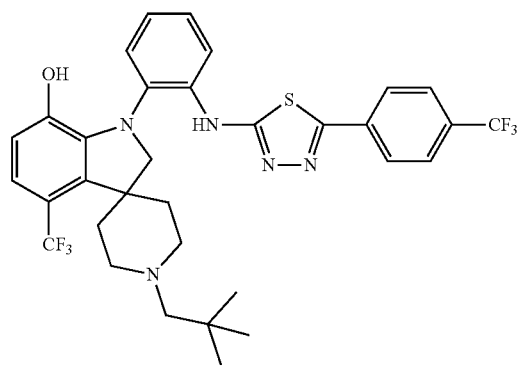

LC-MS ESI 662.3 (M+H) (Method A, RT=3.45 min). $^1$H NMR (400 MHz, chloroform-d) δ ppm 7.85 (2H, d, J=8.35 Hz), 7.66 (2H, d, J=7.91 Hz), 7.55 (1H, d, J=5.71 Hz), 7.14 (2H, d, J=7.03 Hz), 7.08 (1H, s), 6.99 (1H, s), 6.82 (1H, s), 3.63-3.73 (1H, m), 3.37-3.48 (1H, m), 2.55-2.64 (2H, m), 2.34 (2H, t, J=12.52 Hz), 2.08-2.20 (2H, m), 1.93 (2H, s), 1.38 (1H, d, J=12.30 Hz), 1.13-1.21 (1H, m), 0.80 (9H, s).

Orthogonal HPLC purity: RT=8.68 min, 94% (Method A); RT=7.55 min, 93% (Method B).

Example 4

1-(2-(5-(4-Fluorophenyl)-1,3,4-thiadiazol-2-ylamino)phenyl)-1'-neopentyl-4-(trifluoromethyl)spiro[indoline-3,4'-piperidin]-7-ol

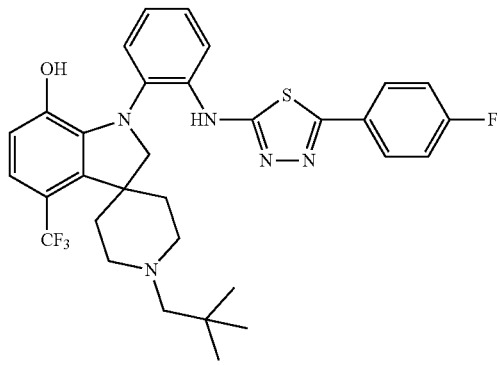 [SMILES: CC(C)(C)CN1CCC2(CC1)CN(c1ccccc1Nc1nnc(-c3ccc(F)cc3)s1)c1c(O)ccc(C(F)(F)F)c12]

LC-MS ESI 612.6 (M+H) (Method A, RT=3.06 min). $^1$H NMR (400 MHz, methanol-$d_3$) δ ppm 7.90 (1H, d, J=7.15 Hz), 7.80-7.87 (2H, m), 7.19-7.25 (3H, m), 7.12-7.19 (1H, m), 7.08-7.11 (1H, m), 7.03-7.08 (1H, m), 6.77 (1H, t, J=8.52 Hz), 4.08-4.17 (1H, m), 3.57 (2H, t, J=10.72 Hz), 3.26 (1H, s), 3.10-3.21 (2H, m), 2.98 (2H, s), 2.74 (1H, td, J=14.02, 3.85 Hz), 2.57 (1H, td, J=14.02, 4.40 Hz), 1.86-1.97 (2H, m), 1.09 (9H, s). Orthogonal HPLC purity: RT=8.17 min, 100% (Method A); RT=6.82 min, 99% (Method B).

Example 5

1-(2-(5-(3-Fluorophenyl)-1,3,4-thiadiazol-2-ylamino)phenyl)-1'-neopentyl-4-(trifluoromethyl)spiro[indoline-3,4'-piperidin]-7-ol

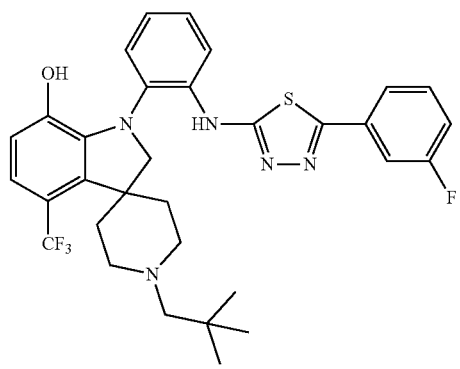 [SMILES: CC(C)(C)CN1CCC2(CC1)CN(c1ccccc1Nc1nnc(-c3cccc(F)c3)s1)c1c(O)ccc(C(F)(F)F)c12]

LC-MS ESI 612.6 (M+H) (Method A, RT=3.08 min). $^1$H NMR (400 MHz, methanol-$d_3$) δ ppm 7.89 (1H, d, J=7.70 Hz), 7.58 (2H, d, J=7.15 Hz), 7.45-7.53 (1H, m), 7.17-7.24 (2H, m), 7.15 (1H, d, J=8.25 Hz), 7.03-7.12 (2H, m), 6.78 (1H, t, J=8.52 Hz), 4.09-4.15 (1H, m), 3.58 (3H, t, J=10.99 Hz), 3.10-3.21 (2H, m), 2.98 (2H, s), 2.74 (1H, td, J=14.02, 3.85 Hz), 2.57 (1H, td, J=14.02, 4.40 Hz), 1.86-1.96 (2H, m), 1.09 (9H, s). Orthogonal HPLC purity: RT=8.22 min, 100% (Method A); RT=6.87 min, 100% (Method B).

Example 6

1'-Neopentyl-1-(2-(5-(pyridin-2-yl)-1,3,4-thiadiazol-2-ylamino)phenyl)-4-(trifluoromethyl)spiro[indoline-3,4'-piperidin]-7-ol

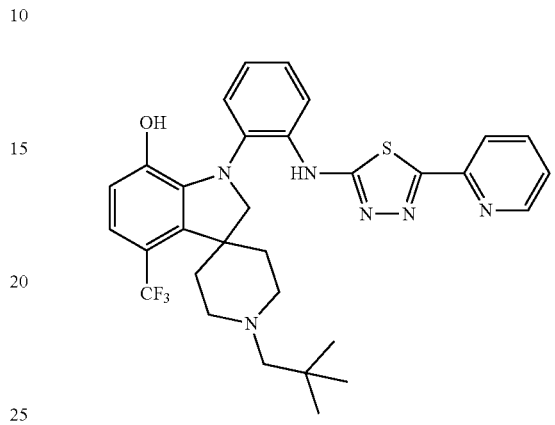

LC-MS ESI 595.6 (M+H) (Method A, RT=2.78 min). $^1$H NMR (400 MHz, methanol-$d_3$) δ ppm 8.56 (1H, d, J=4.40 Hz), 8.15 (1H, d, J=7.70 Hz), 7.88-7.94 (2H, m), 7.39-7.46 (1H, m), 7.23 (1H, t, J=6.87 Hz), 7.14-7.18 (1H, m), 7.04-7.12 (2H, m), 6.77 (1H, t, J=8.52 Hz), 4.09-4.16 (1H, m), 3.57 (2H, t, J=10.17 Hz), 3.19-3.27 (2H, m), 3.13 (1H, d, J=15.39 Hz), 2.97 (2H, s), 2.69-2.80 (1H, m), 2.57 (1H, td, J=14.02, 3.85 Hz), 1.89-2.00 (2H, m), 1.08 (9H, s). Orthogonal HPLC purity: RT=7.64 min, 99% (Method A); RT=6.29 min, 100% (Method B).

Example 7

4-Chloro-1'-neopentyl-1-(2-(5-(4-(trifluoromethyl)phenyl)-1,3,4-thiadiazol-2-ylamino)phenyl)spiro[indoline-3,4'-piperidin]-7-ol

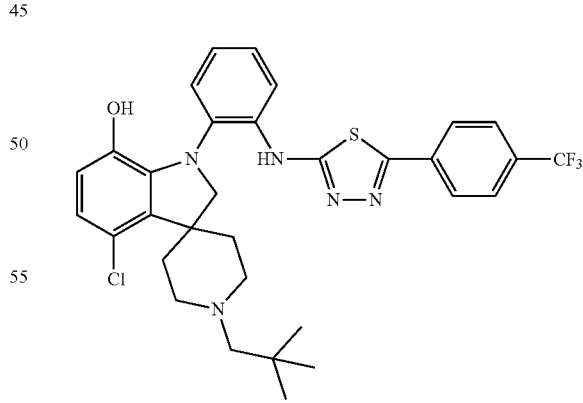

LC-MS ESI 628.6 (M+H) (Method A, RT=3.21 min). $^1$H NMR (400 MHz, methanol-$d_3$) δ ppm 8.01 (2H, d, J=8.25 Hz), 7.94 (1H, d, J=7.15 Hz), 7.79 (2H, d, J=8.24 Hz), 7.18-7.25 (1H, m), 7.03-7.13 (2H, m), 6.71-6.78 (1H, m), 6.65 (1H, t, J=8.52 Hz), 4.16 (1H, d, J=10.99 Hz), 3.51-3.63 (3H, m), 3.15-3.26 (2H, m), 3.06-3.14 (2H, m), 2.97-3.04 (2H, m), 1.82-1.93 (2H, m), 1.10 (9H, s). Orthogonal HPLC purity: RT=8.56 min, 89% (Method A); RT=7.23 min, 94% (Method B).

Example 8

4-Chloro-1'-neopentyl-1-(2-(5-(5-(trifluoromethyl)pyridin-2-yl)-1,3,4-thiadiazol-2-ylamino)phenyl)spiro[indoline-3,4'-piperidin]-7-ol

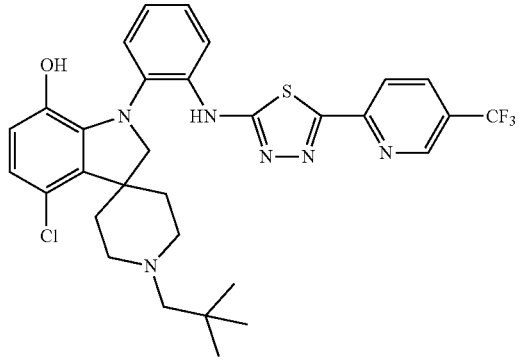 [SMILES: CC(C)(C)CN1CCC2(CC1)CN(c1ccccc1Nc1nnc(-c3ccc(C(F)(F)F)cc3)s1)c1c(O)ccc(Cl)c12]

LC-MS ESI 629.6 (M+H) (Method A, RT=3.20 min). $^1$H NMR (400 MHz, methanol-$d_3$) δ ppm 8.87 (1H, s), 8.33 (1H, d, J=8.34 Hz), 8.22 (1H, dd, J=8.34, 2.02 Hz), 7.95 (1H, d, J=7.07 Hz), 7.22 (1H, td, J=7.52, 1.89 Hz), 7.04-7.12 (2H, m), 6.70-6.77 (1H, m), 6.61-6.67 (1H, m), 4.16 (1H, d, J=10.61 Hz), 3.51-3.63 (3H, m), 3.12-3.22 (1H, m), 3.07-3.17 (2H, m), 3.03 (1H, dd, J=14.53, 3.41 Hz), 2.98 (2H, s), 1.92 (1H, d, J=14.65 Hz), 1.84 (1H, d, J=11.12 Hz), 1.10 (9H, s). Orthogonal HPLC purity: RT=8.42 min, 98% (Method A); RT=6.99 min, 100% (Method B).

Example 9

4-Chloro-1'-neopentyl-1-(2-((5-(pyridin-3-yl)-1,3,4-thiadiazol-2-yl)amino)phenyl)spiro[indoline-3,4'-piperidin]-7-ol

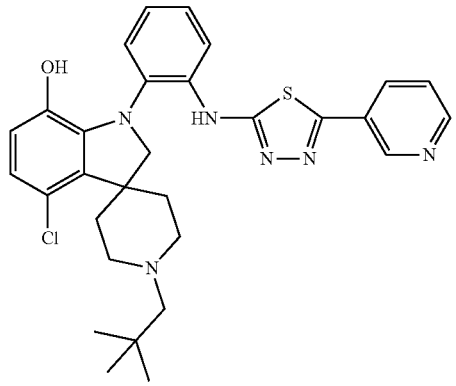 [SMILES: CC(C)(C)CN1CCC2(CC1)CN(c1ccccc1Nc1nnc(-c3cccnc3)s1)c1c(O)ccc(Cl)c12]

LC-MS ESI 561.3 (M+H) (Method A, RT=2.36 min). $^1$H NMR (400 MHz, methanol-$d_3$) δ ppm 9.11 (1H, d, J=1.76 Hz), 8.73 (1H, dd, J=5.05, 1.10 Hz), 8.52 (1H, ddd, J=8.02, 1.98, 1.87 Hz), 7.89-8.02 (1H, m), 7.79 (1H, dd, J=8.13, 5.49 Hz), 7.22 (1H, td, J=7.47, 1.76 Hz), 7.01-7.15 (2H, m), 6.70- 6.81 (1H, m), 6.58-6.70 (1H, m), 4.17 (1H, d, J=10.55 Hz), 3.98 (2H, s), 3.57-3.69 (1H, m), 3.54 (1H, d, J=10.55 Hz), 3.15-3.25 (1H, m), 3.06-3.12 (2H, m), 3.01 (2H, s), 1.76-1.98 (2H, m), 1.12 (9H, s). Orthogonal HPLC purity: RT=6.30 min, 98.5% (Method A); RT=6.30 min, 98.6% (Method B).

Example 10

4-Chloro-1'-neopentyl-1-(2-((5-(pyridin-4-yl)-1,3,4-thiadiazol-2-yl)amino)phenyl)spiro[indoline-3,4'-piperidin]-7-ol

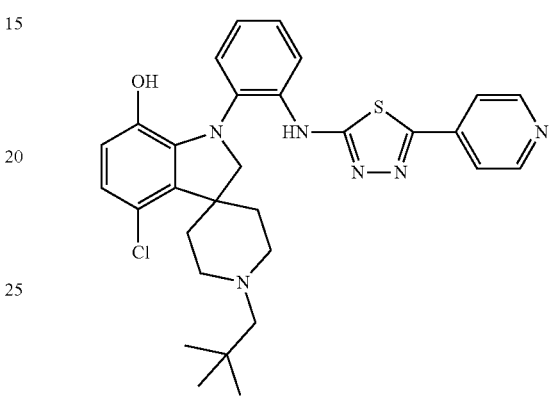

LC-MS ESI 560.9 (M+H) (Method B, RT=1.52 min). $^1$H NMR (400 MHz, methanol-$d_3$) d ppm 8.69 (2H, d, J=6.05 Hz), 7.84-8.01 (3H, m), 7.19-7.29 (1H, m), 7.03-7.15 (2H, m), 6.71-6.81 (1H, m), 6.61-6.70 (1H, m), 4.16 (1H, d, J=10.44 Hz), 3.55 (2H, d, J=10.99 Hz), 3.16-3.25 (1H, m), 3.03-3.16 (2H, m), 3.01 (2H, s), 1.80-1.97 (2H, m), 1.12 (9H, s). Orthogonal HPLC purity: RT=4.71 min, 100% (Method A); RT=5.82 min, 100% (Method B).

Example 11

4-Chloro-1'-neopentyl-1-(2-(5-phenylthiazol-2-ylamino)phenyl)spiro[indoline-3,4'-piperidin]-7-ol

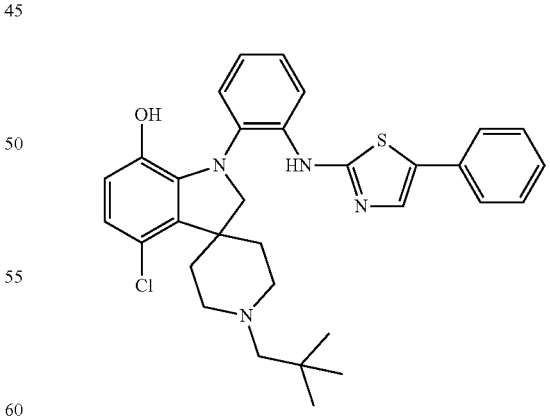

Example 11 was prepared following the procedure described for Example 1 with 2-amino-1-phenylethanone as starting material. LC-MS ESI 559.4 (M+H) (Method B, RT=1.59 min). $^1$H NMR (400 MHz, methanol-$d_3$) δ ppm 7.65 (1H, t, J=7.70 Hz), 7.56-7.60 (1H, m), 7.49 (2H, d, J=7.15 Hz), 7.39 (2H, t, J=7.70 Hz), 7.31 (1H, t, J=7.42 Hz), 7.19-

7.27 (2H, m), 7.13 (1H, d, J=7.70 Hz), 6.70-6.78 (1H, m), 6.61-6.68 (1H, m), 4.11 (1H, d, J=10.44 Hz), 3.66 (1H, d, J=10.44 Hz), 3.59 (2H, d, J=9.89 Hz), 3.28 (1H, s), 3.16 (1H, s), 3.06-3.14 (2H, m), 2.95-3.00 (2H, m), 1.79-1.90 (2H, m), 1.10 (9H, s). Orthogonal HPLC purity: RT=7.63 min, 99% (Method A); RT=6.22 min, 99% (Method B).

Example 12

4-Chloro-1'-neopentyl-1-(2-((5-(pyrazin-2-yl)-1,3,4-thiadiazol-2-yl)amino)phenyl)spiro[indoline-3,4'-piperidin]-7-ol

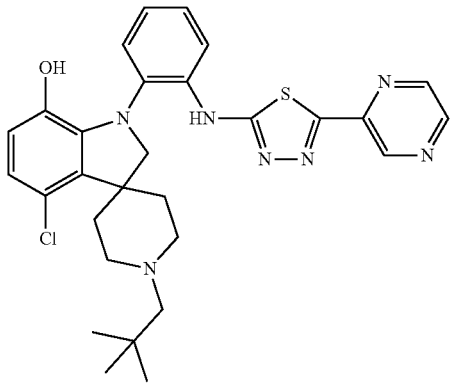

Example 12A

N-(2-(4-Chloro-7-methoxy-1'-neopentylspiro[indoline-3,4'-piperidine]-1-yl)phenyl)hydrazinecarbothioamide A solution of Example 1A (1.1 g, 2.4 mmol) and tert-butyl hydrazinecarboxylate (0.32 g, 2.4 mmol) in dichloromethane (5 mL) was stirred at 23° C. for 18 h. Trifluoroacetic acid (4.65 mL, 60.3 mmol) was added dropwise. After 2 h, the reaction mixture was then neutralized with saturated NaHCO₃. The reaction mixture was concentrated, re-dissolved in EtOAc (10 mL), washed with saturated NaHCO₃ (30 mL), dried over MgSO₄, and concentrated to give crude Example 12A as a white solid (1.24 g, 2.54 mmol, quant.). LC-MS ESI 488.9 (M+H) (Method A, RT=2.58 min).

Example 12

In a 1 mL vial, Example 12A (50 mg, 0.10 mmol) and pyrazine-2-carbonyl chloride (14.6 mg, 0.102 mmol) were stirred in DCM (1 mL). The reaction was stirred at rt for 2 h then heated at 40° C. for 2 h before added sulfuric acid (0.109 mL, 2.049 mmol) and stirred at rt for 18 h. At 0° C., the reaction was basified by 15% NaOH to pH ~9-10, and extracted with dichloromethane (2 mL×3). The organic layers were combined, dried over MgSO₄, and concentrated to give crude N-(2-(4-chloro-7-methoxy-1'-neopentylspiro[indoline-3,4'-piperidine]-1-yl)phenyl)-5-(pyrazin-2-yl)-1,3,4-thiadiazol-2-amine (58.8 mg) which was used directly in the next step. The crude (58.8 mg, 0.102 mmol) and boron trichloride (1.02 mL, 1.02 mmol) were stirred at 66° C. for 18 h. At 0° C., MeOH (0.5 mL) was added dropwise and stirred for 10 min and purified by prep HPLC (10-70% acetonitrile over 15 min, 0.1% TFA as modifier) to give Example 12, TFA (3 mg, 4% yield). LC-MS ESI 561.9 (M+H) (Method B, RT=1.70 min). ¹H NMR (400 MHz, methanol-d₃) δ ppm 9.35 (1H, br. s.), 8.58-8.68 (2H, m), 7.87-8.01 (1H, m), 7.16-7.35 (1H, m), 7.01-7.16 (2H, m), 6.62-6.79 (2H, m), 4.05-4.26 (1H, m), 3.55 (2H, br. s.), 3.53 (1H, d, J=6.05 Hz), 3.18 (1H, br. s.), 3.11 (2H, d, J=3.85 Hz), 3.05 (1H, br. s.), 3.01 (2H, d, J=2.75 Hz), 1.95 (1H, br. s.), 1.87 (1H, br. s.), 1.12 (9H, d, J=3.85 Hz). Orthogonal HPLC purity: RT=6.16 min, 95.5% (Method A); RT=7.47 min, 96.6% (Method B).

Examples 13-15 were prepared following the procedure described for Example 12.

Example 13

4-Chloro-1-(2-((5-(1,3-dimethyl-1H-pyrazol-5-yl)-1,3,4-thiadiazol-2-yl)amino)phenyl)-1'-neopentylspiro[indoline-3,4'-piperidin]-7-ol

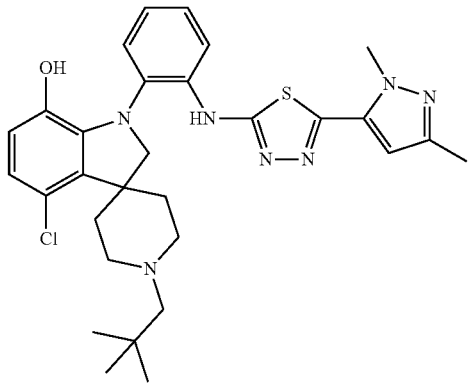 [SMILES: Cc1cc(-c2nnc(Nc3ccccc3N3CC4(CCN(CC(C)(C)C)CC4)c4c(Cl)ccc(O)c43)s2)n(C)n1]

LC-MS ESI 578.3 (M+H) (Method A, RT=2.72 min). ¹H NMR (400 MHz, methanol-d₃) δ ppm 7.84-7.97 (1H, m), 7.16-7.24 (1H, m), 7.02-7.14 (2H, m), 6.70-6.80 (1H, m), 6.59-6.69 (1H, m), 6.37-6.43 (1H, m), 4.13-4.22 (1H, m), 4.07-4.12 (3H, m), 3.98 (2H, s), 3.56-3.69 (1H, m), 3.53 (1H, d, J=10.55 Hz), 3.14-3.24 (1H, m), 3.02-3.13 (2H, m), 3.00 (2H, s), 2.24 (3H, s), 1.85-1.97 (1H, m), 1.84 (1H, d, J=9.67 Hz), 1.12 (9H, s). Orthogonal HPLC purity: RT=7.38 min, 93.5% (Method A); RT=7.38 min, 96.9% (Method B).

Example 14

4-Chloro-1'-neopentyl-1-(2-((5-(tetrahydro-2H-pyran-4-yl)-1,3,4-thiadiazol-2-yl)amino)phenyl)spiro[indoline-3,4'-piperidin]-7-ol

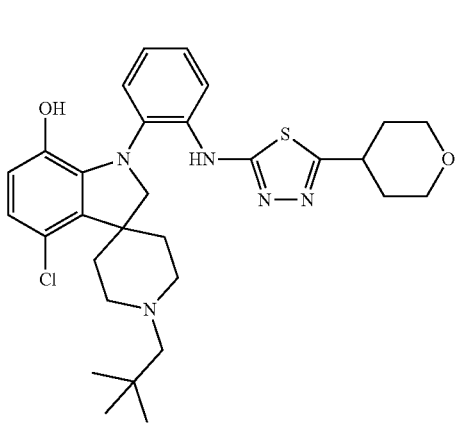 [SMILES: CC(C)(C)CN1CCC2(CC1)CN(c1ccccc1Nc1nnc(C3CCOCC3)s1)c1c(O)ccc(Cl)c12]

LC-MS ESI 568.3 (M+H) (Method A, RT=2.47 min). $^1$H NMR (500 MHz, methanol-$d_3$) d ppm 7.73-7.86 (1H, m), 7.14-7.23 (1H, m), 7.00-7.12 (2H, m), 6.69-6.79 (1H, m), 6.59-6.67 (1H, m), 4.14 (1H, d, J=10.45 Hz), 4.00 (1H, br. s.), 3.98 (2H, s), 3.64 (1H, d, J=13.20 Hz), 3.56-3.60 (1H, m), 3.49-3.56 (2H, m), 3.21-3.29 (2H, m), 3.07-3.14 (2H, m), 2.95-3.07 (3H, m), 1.97 (2H, d, J=13.20 Hz), 1.74-1.92 (4H, m), 1.14 (9H, s). Orthogonal HPLC purity: RT=5.82 min, 96.3% (Method A); RT=6.91 min, 97.7% (Method B).

Example 15

4-Chloro-1'-neopentyl-1-(2-((5-(6-(trifluoromethyl)pyridin-3-yl)-1,3,4-thiadiazol-2-yl)amino)phenyl)spiro[indoline-3,4'-piperidin]-7-ol

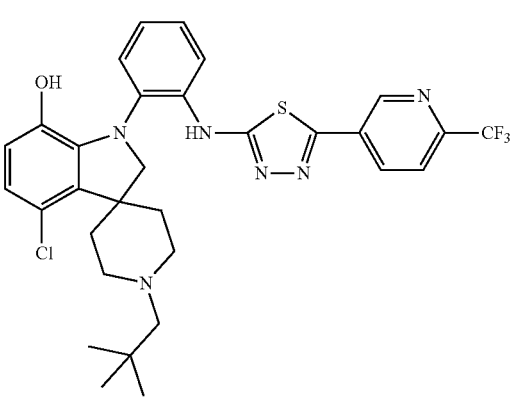 [SMILES: CC(C)(C)CN1CCC2(CC1)CN(c1ccccc1Nc1nnc(-c3ccc(C(F)(F)F)nc3)s1)c1c(O)ccc(Cl)c12]

LC-MS ESI 629.2 (M+H) (Method A, RT=2.96 min). $^1$H NMR (500 MHz, methanol-$d_3$) d ppm 9.13 (1H, s), 8.42 (1H, d, J=7.70 Hz), 7.84-8.00 (2H, m), 7.17-7.25 (1H, m), 7.03-7.15 (2H, m), 6.70-6.80 (1H, m), 6.60-6.70 (1H, m), 4.17 (1H, d, J=10.45 Hz), 3.50-3.69 (3H, m), 3.14-3.22 (1H, m), 3.12 (1H, d, J=4.95 Hz), 3.02-3.11 (2H, m), 3.00 (2H, s), 1.91 (1H, d, J=14.30 Hz), 1.85 (1H, d, J=10.45 Hz), 1.11 (9H, s). Orthogonal HPLC purity: RT=7.53 min, 95.3% (Method A); RT=8.53 min, 97.7% (Method B).

Examples 16-34 listed in Table 1 were prepared following the procedure described for Example 1 or 12.

TABLE 1

| Example | Structure | Name | [M + H]⁺ | RT (min) | LC/MS Method |
|---|---|---|---|---|---|
| 16 | 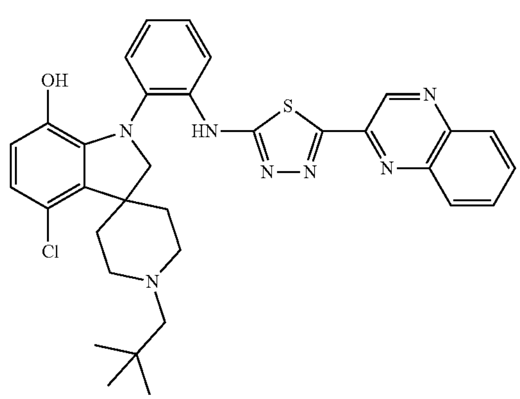 [SMILES: CC(C)(C)CN1CCC2(CC1)CN(c1ccccc1Nc1nnc(-c3cnc4ccccc4n3)s1)c1c(O)ccc(Cl)c12] | 4-chloro-1'-neopentyl-1-(2-((5-(quinoxalin-2-yl)-1,3,4-thiadiazol-2-yl)amino)phenyl)spiro[indoline-3,4'-piperidin]-7-ol | 612.3 | 4.81 | D |

TABLE 1-continued

| Example | Structure | Name | [M + H]+ | RT (min) | LC/MS Method |
|---|---|---|---|---|---|
| 17 | 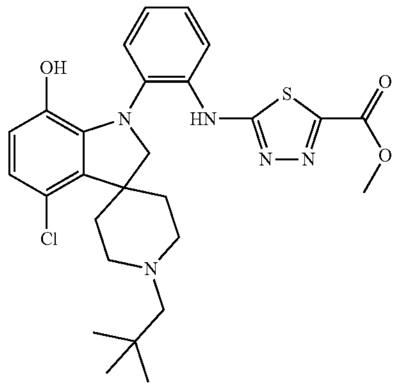 [SMILES: COC(=O)c1nnc(Nc2ccccc2N2CC3(CCN(CC(C)(C)C)CC3)c3c(Cl)ccc(O)c32)s1] | methyl 5-((2-(4-chloro-7-hydroxy-1'-neopentylspiro[indoline-3,4'-piperidin]-1-yl)phenyl)-amino)-1,3,4-thiadiazole-2-carboxylate | 542.2 | 3.66 | D |
| 18 | 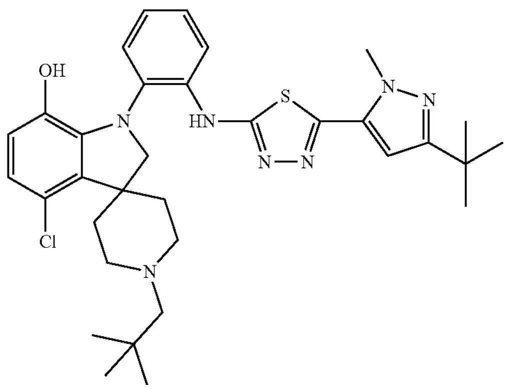 [SMILES: Cn1nc(C(C)(C)C)cc1-c1nnc(Nc2ccccc2N2CC3(CCN(CC(C)(C)C)CC3)c3c(Cl)ccc(O)c32)s1] | 1-(2-((5-(3-(tert-butyl)-1-methyl-1H-pyrazol-5-yl)-1,3,4-thiadiazol-2-yl)amino)phenyl)-4-chloro-1'-neopentylspiro[indoline-3,4'-piperidin]-7-ol | 620.4 | 5.03 | D |
| 19 | 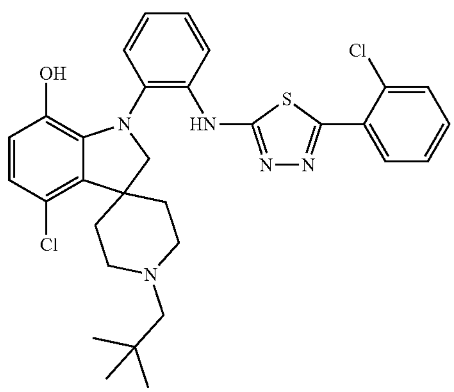 [SMILES: CC(C)(C)CN1CCC2(CC1)CN(c1ccccc1Nc1nnc(-c3ccccc3Cl)s1)c1c(O)ccc(Cl)c12] | 4-chloro-1-(2-((5-(2-chloro-phenyl)-1,3,4-thiadiazol-2-yl)amino)phenyl)-1'-neopentylspiro[indoline-3,4'-piperidin]-7-ol | 594.2 | 5.1 | E |
| 20 | 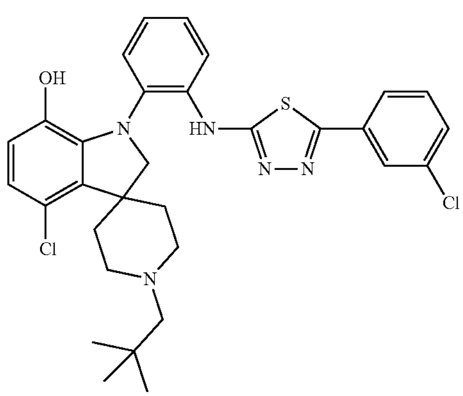 [SMILES: CC(C)(C)CN1CCC2(CC1)CN(c1ccccc1Nc1nnc(-c3cccc(Cl)c3)s1)c1c(O)ccc(Cl)c12] | 4-chloro-1-(2-((5-(3-chloro-phenyl)-1,3,4-thiadiazol-2-yl)amino)phenyl)-1'-neopentylspiro[indoline-3,4'-piperidin]-7-ol | 594.2 | 5.3 | E |

TABLE 1-continued

| Example | Structure | Name | [M + H]⁺ | RT (min) | LC/MS Method |
|---|---|---|---|---|---|
| 21 | 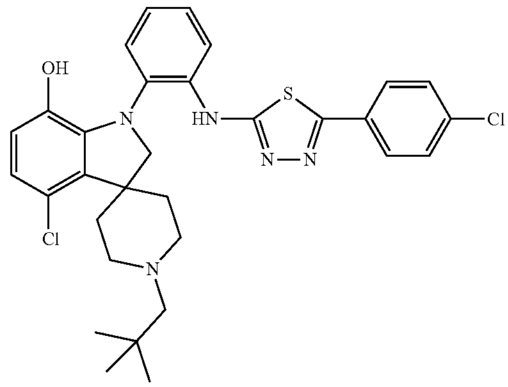 | 4-chloro-1-(2-((5-(4-chlorophenyl)-1,3,4-thiadiazol-2-yl)amino)phenyl)-1'-neopentylspiro[indoline-3,4'-piperidin]-7-ol | 594.2 | 5.28 | E |
| 22 | 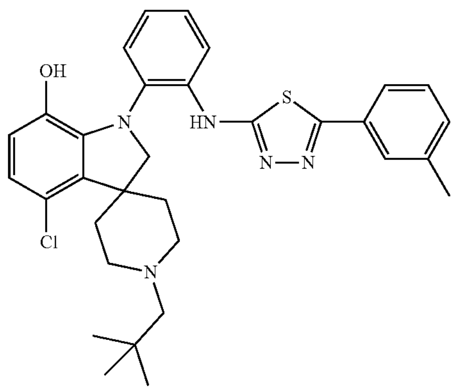 [SMILES: Cc1cccc(-c2nnc(Nc3ccccc3N3CC4(CCN(CC(C)(C)C)CC4)c4c(Cl)ccc(O)c43)s2)c1] | 4-chloro-1'-neopentyl-1-(2-((5-(m-tolyl)-1,3,4-thiadiazol-2-yl)amino)phenyl)spiro[indoline-3,4'-piperidin]-7-ol | 574.2 | 5.16 | E |
| 23 | 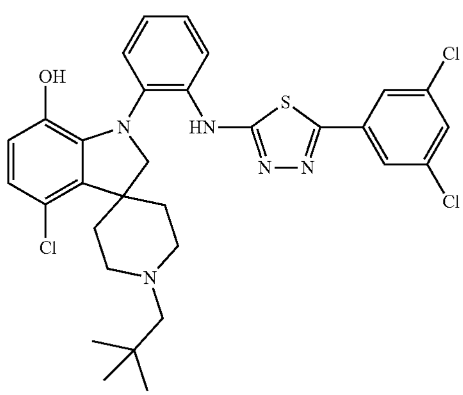 [SMILES: CC(C)(C)CN1CCC2(CC1)CN(c1ccccc1Nc1nnc(-c3cc(Cl)cc(Cl)c3)s1)c1c(O)ccc(Cl)c12] | 4-chloro-1-(2-((5-(3,5-dichlorophenyl)-1,3,4-thiadiazol-2-yl)amino)phenyl)-1'-neopentylspiro[indoline-3,4'-piperidin]-7-ol | 628.1 | 5.63 | E |
| 24 | 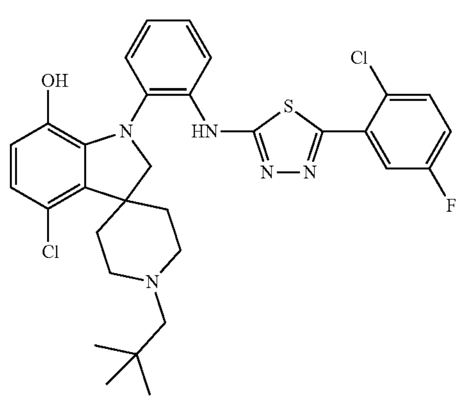 [SMILES: CC(C)(C)CN1CCC2(CC1)CN(c1ccccc1Nc1nnc(-c3cc(F)ccc3Cl)s1)c1c(O)ccc(Cl)c12] | 4-chloro-1-(2-((5-(2-chloro-5-fluorophenyl)-1,3,4-thiadiazol-2-yl)amino)phenyl)-1'-neopentylspiro[indoline-3,4'-piperidin]-7-ol | 612.2 | 5.2 | E |

TABLE 1-continued

| Example | Structure | Name | [M + H]+ | RT (min) | LC/MS Method |
|---|---|---|---|---|---|
| 25 | 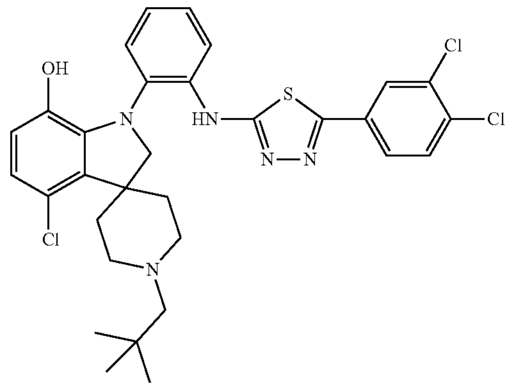 [SMILES: CC(C)(C)CN1CCC2(CC1)CN(c1ccccc1Nc1nnc(-c3ccc(Cl)c(Cl)c3)s1)c1c(O)ccc(Cl)c12] | 4-chloro-1-(2-((5-(3,4-dichlorophenyl)-1,3,4-thiadiazol-2-yl)amino)phenyl)-1'-neopentylspiro[indoline-3,4'-piperidin]-7-ol | 628.1 | 5.56 | E |
| 26 | 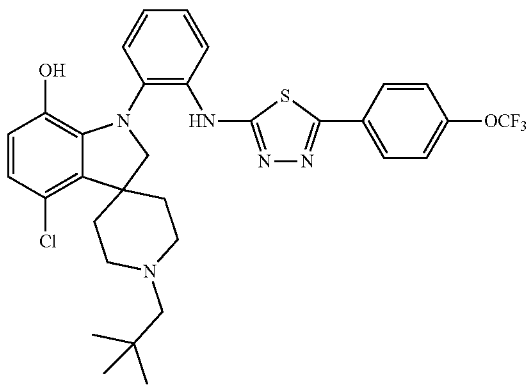 [SMILES: CC(C)(C)CN1CCC2(CC1)CN(c1ccccc1Nc1nnc(-c3ccc(OC(F)(F)F)cc3)s1)c1c(O)ccc(Cl)c12] | 4-chloro-1'-neopentyl-1-(2-((5-(4-(trifluoromethoxy)phenyl)-1,3,4-thiadiazol-2-yl)amino)phenyl)spiro[indoline-3,4'-piperidin]-7-ol | 644.2 | 5.43 | E |
| 27 | 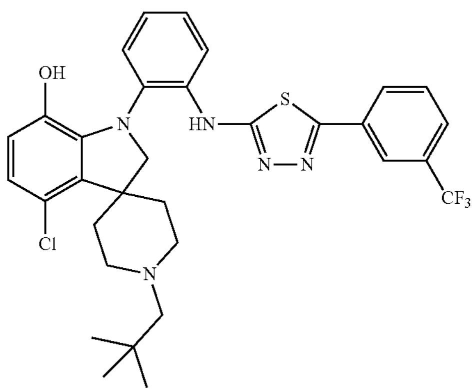 [SMILES: CC(C)(C)CN1CCC2(CC1)CN(c1ccccc1Nc1nnc(-c3cccc(C(F)(F)F)c3)s1)c1c(O)ccc(Cl)c12] | 4-chloro-1'-neopentyl-1-(2-((5-(3-(trifluoromethyl)phenyl)-1,3,4-thiadiazol-2-yl)amino)phenyl)spiro[indoline-3,4'-piperidin]-7-ol | 628.2 | 5.4 | E |
| 28 | 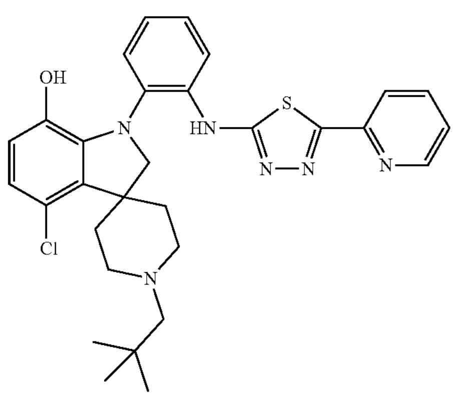 [SMILES: CC(C)(C)CN1CCC2(CC1)CN(c1ccccc1Nc1nnc(-c3ccccn3)s1)c1c(O)ccc(Cl)c12] | 4-chloro-1'-neopentyl-1-(2-((5-(pyridin-2-yl)-1,3,4-thiadiazol-2-yl)amino)phenyl)-spiro[indoline-3,4'-piperidin]-7-ol | 561.2 | 4.69 | E |

TABLE 1-continued

| Example | Structure | Name | [M + H]+ | RT (min) | LC/MS Method |
|---|---|---|---|---|---|
| 29 | 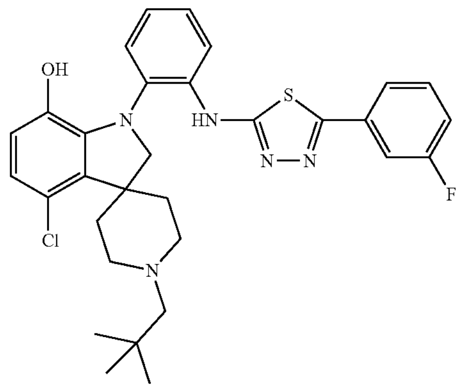 [SMILES: CC(C)(C)CN1CCC2(CC1)CN(c1ccccc1Nc1nnc(-c3cccc(F)c3)s1)c1c(O)ccc(Cl)c12] | 4-chloro-1-(2-((5-(3-fluoro-phenyl)-1,3,4-thiadiazol-2-yl)amino)phenyl)-1'-neopentylspiro[indoline-3,4'-piperidin]-7-ol | 578 | 3.87 | F |
| 30 | 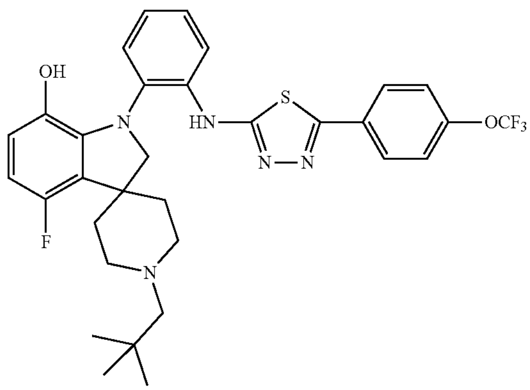 | 4-fluoro-1'-neopentyl-1-(2-((5-(4-(trifluoromethoxy)-phenyl)-1,3,4-thiadiazol-2-yl)amino)phenyl)spiro[indoline-3,4'-piperidin]-7-ol | 628.2 | 1.80 | C |
| 31 | 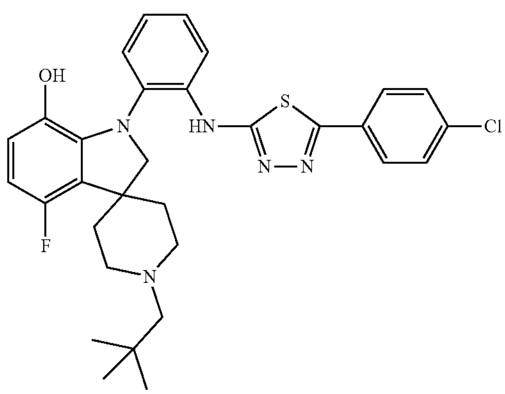 | 1-(2-((5-(4-chlorophenyl)-1,3,4-thiadiazol-2-yl)amino)phenyl)-4-fluoro-1'-neopentylspiro-[indoline-3,4'-piperidin]-7-ol | 578.2 | 1.68 | C |
| 32 | 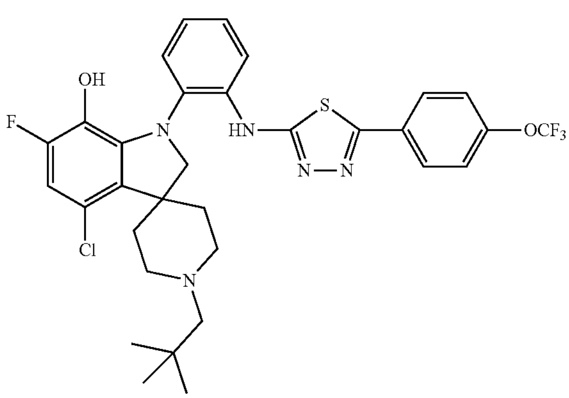 [SMILES: CC(C)(C)CN1CCC2(CC1)CN(c1ccccc1Nc1nnc(-c3ccc(OC(F)(F)F)cc3)s1)c1c(O)c(F)cc(Cl)c12] | 4-chloro-6-fluoro-1'-neopentyl-1-(2-((5-(4-(trifluoromethoxy)-phenyl)-1,3,4-thiadiazol-2-yl)amino)phenyl)spiro[indoline-3,4'-piperidin]-7-ol | 662.2 | 1.80 | C |

TABLE 1-continued

| Example | Structure | Name | [M + H]+ | RT (min) | LC/MS Method |
|---|---|---|---|---|---|
| 33 | 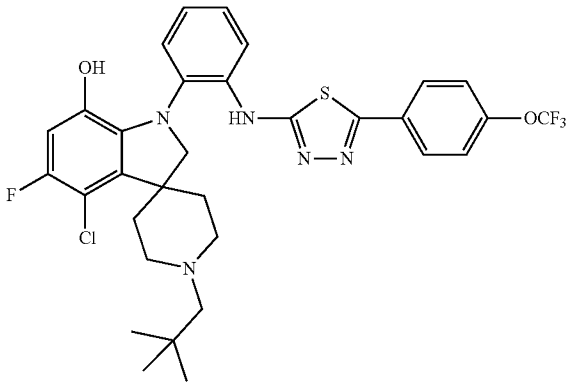 [SMILES: CC(C)(C)CN1CCC2(CC1)CN(c1ccccc1Nc1nnc(-c3ccc(OC(F)(F)F)cc3)s1)c1c(O)cc(F)c(Cl)c12] | 4-chloro-5-fluoro-1'-neopentyl-1-(2-((5-(4-(trifluoromethoxy)-phenyl)-1,3,4-thiadiazol-2-yl)amino)phenyl)spiro[indoline-3,4'-piperidin]-7-ol | 662.2 | 1.87 | C |
| 34 | 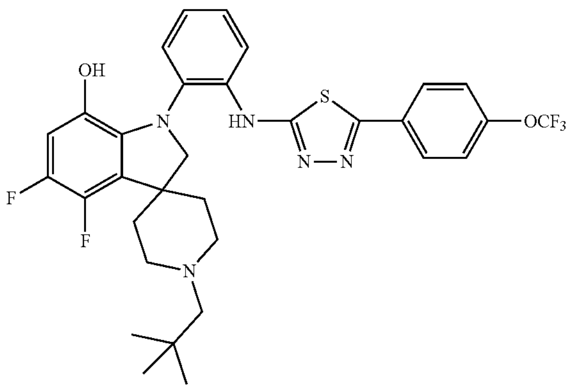 | 4,5-difluoro-1'-neopentyl-1-(2-((5-(4-(trifluoromethoxy)-phenyl)-1,3,4-thiadiazol-2-yl)amino)phenyl)spiro[indoline-3,4'-piperidin]-7-ol | 646.2 | 1.81 | C |

Example 35

4-Chloro-1'-neopentyl-1-(2-(3-phenyl-1,2,4-thiadiazol-5-ylamino)phenyl)spiro[indoline-3,4'-piperidin]-7-ol

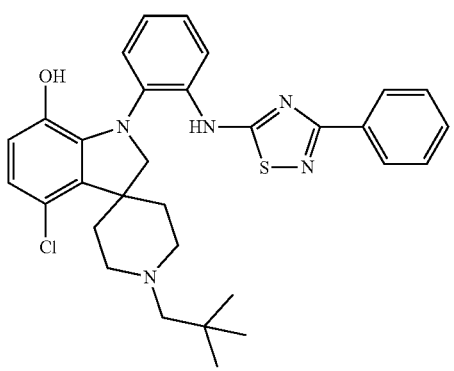

Example 35A

4-Chloro-1-(2-isothiocyanatophenyl)-7-methoxy-1'-neopentylspiro[indoline-3,4'-piperidine]

At 0° C., to a solution of Intermediate 2 (0.99 g, 2.4 mmol) in dichloromethane (10 mL) was added 1,1'-thiocarbonyl-dipyridin-2 (1H)-one (0.555 g, 2.39 mmol) in dichloromethane (15 mL) dropwise over 20 min. The reaction temperature was stirred at 23° C. for 18 h. The reaction was concentrated and purified by flash chromatography (silica gel, eluting with EtOAc/Hexanes) to give Example 35A as a white solid (0.993 g, 2.18 mmol, 91.0% yield). LC-MS ESI 456.5 (M+H), 458.5 (M+H+2) (Method A, RT=3.20 min). $^1$H NMR (400 MHz, chloroform-d) δ ppm 7.19 (1H, d, J=8.25 Hz), 7.12 (1H, d, J=7.15 Hz), 7.04 (1H, d, J=6.05 Hz), 6.91 (1H, d, J=6.60 Hz), 6.82 (1H, d, J=8.25 Hz), 6.66 (1H, d, J=8.79 Hz), 4.08-4.16 (1H, m), 3.56-3.63 (1H, m), 3.54 (3H, s), 2.75 (3H, d, J=14.29 Hz), 2.32 (1H, s), 2.22 (1H, s), 2.03 (2H, s), 1.39 (1H, s), 1.20-1.32 (2H, m), 0.87 (9H, s).

Example 35B

N-(2-(4-Chloro-7-methoxy-1'-neopentylspiro[indoline-3,4'-piperidine]-1-yl)phenyl)-3-phenyl-1,2,4-thiadiazol-5-amine A solution of Example 35A (104 mg, 0.228 mmol) and benzimidamide (27.4 mg, 0.228 mmol) in DMF (1 mL) were stirred for 18 h at 23° C. Diethyl azodicarboxylate (0.072 mL, 0.46 mmol) was added dropwise. After 30 min, the reaction mixture was quenched with saturated NaHCO$_3$, extracted with dichloromethane (2 mL×3), concentrated, and purified by flash chromatography (silica gel, eluting with EtOAc/Hexanes) to give Example 35B as a yellowish oil (52 mg, 0.091 mmol, 40% yield). LC-MS ESI 574.6 (M+H), 476.6 (M+H+2) (Method A, RT=3.42 min). $^1$H NMR (400 MHz, chloroform-d) δ ppm 8.75 (1H, s), 8.21-8.27 (2H, m), 7.62-7.66 (1H, m), 7.45 (1H, d, J=2.20 Hz), 7.43 (2H, d, J=2.20 Hz), 7.26-7.31 (1H, m), 7.05 (1H, s), 7.02-7.05 (1H, m), 6.83 (1H, d, J=8.25 Hz), 6.60 (1H, d, J=8.25 Hz), 4.02 (1H, d, J=10.44 Hz), 3.42 (3H, s), 3.31 (1H, d, J=9.89 Hz), 2.89 (1H, td, J=12.92, 4.40 Hz), 2.79 (1H, d, J=12.09 Hz), 2.64-2.75 (2H, m), 2.27 (1H, td, J=12.09, 2.20 Hz), 2.09-2.18 (1H, m), 2.00 (2H, s), 1.49-1.60 (2H, m), 0.87 (9H, s).

Example 35

To Example 35B (130 mg, 0.226 mmol) and tetrabutylammonium iodide (502 mg, 1.36 mmol) were stirred in dry dichloromethane (1 mL) under argon at −50° C., boron trichloride in 1 N dichloromethane solution (1.132 mL, 1.132 mmol) was added dropwise. The stirring mixture was stirred from −50 to −10° C. over 1 h, and then dry ice bath was removed. The mixture was stirred at 23° C. for 18 h. The mixture was cooled, while H$_2$O (0.5 mL) was added dropwise. PH was adjusted to 8-9 by adding aq. NaHCO$_3$ and 15% NaOH. The mixture was extracted with CH$_2$Cl$_2$ (2 mL×3). The organic layers were combined, concentrated and purified by flash chromatography (silica gel, eluting with EtOAc/Hexanes) then prep HPLC (18-90% MeOH in H$_2$O over 15 min, 0.1% TFA as modifier) to give Example 35 as a white solid (33 mg, 0.059 mmol, 26% yield). LC-MS ESI 560.5 (M+H), 562.5 (M+H+2) (Method A, RT=3.11 min). $^1$H NMR (400 MHz, methanol-d$_3$) δ ppm 8.09-8.21 (3H, m), 7.42-7.48 (3H, m), 7.22-7.29 (1H, m), 7.05-7.10 (2H, m), 6.74 (1H, d, J=8.79 Hz), 6.61-6.67 (1H, m), 4.17 (1H, d, J=10.99 Hz), 3.52-3.62 (2H, m), 3.41-3.50 (1H, m), 3.07-3.18 (2H, m), 2.96-3.07 (2H, m), 2.93 (2H, s), 1.96 (1H, d, J=12.64 Hz), 1.84 (1H, d, J=12.64 Hz), 1.08 (9H, s). Orthogonal HPLC purity: RT=8.53 min, 93% (Method A); RT=7.01 min, 94% (Method B).

Example 36

1-(2-(3-tert-Butyl-1,2,4-thiadiazol-5-ylamino)phenyl)-4-chloro-1'-neopentylspiro[indoline-3,4'-piperidin]-7-ol

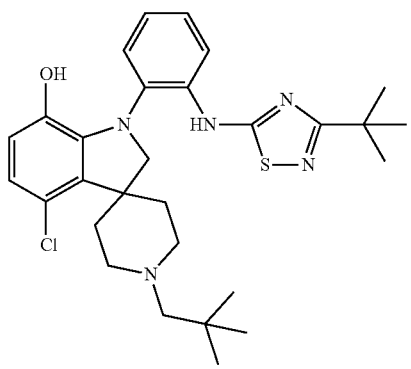 [SMILES: CC(C)(C)CN1CCC2(CC1)CN(c1ccccc1Nc1nc(C(C)(C)C)ns1)c1c(O)ccc(Cl)c12]

Example 36 was prepared following the procedure described for Example 35. LC-MS ESI 540.3 (M+H) (Method A, RT=3.01 min). $^1$H NMR (400 MHz, methanol-d$_3$) δ ppm 8.02-8.10 (1H, m), 7.19-7.24 (1H, m), 7.03 (2H, q, J=8.06 Hz), 6.71-6.77 (1H, m), 6.60-6.65 (1H, m), 4.17 (1H, d, J=10.44 Hz), 3.55-3.67 (2H, m), 3.42-3.47 (1H, m), 3.35 (1H, d, J=8.24 Hz), 3.24 (1H, d, J=6.05 Hz), 3.11-3.21 (2H, m), 2.95-3.05 (2H, m), 2.00 (1H, dd, J=14.29, 2.20 Hz), 1.86 (1H, d, J=12.64 Hz), 1.38 (9H, s), 1.12 (9H, s). Orthogonal HPLC purity: RT=9.32 min, 91% (Method A); RT=6.90 min, 91% (Method B).

Example 37

4-Chloro-1'-neopentyl-1-(2-(5-(4-(trifluoromethyl)phenyl)isoxazol-3-ylamino)phenyl)spiro[indoline-3,4'-piperidin]-7-ol

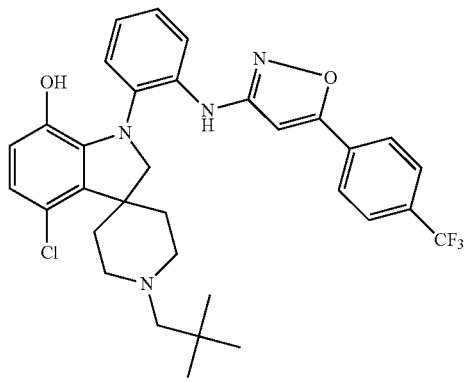 [SMILES: CC(C)(C)CN1CCC2(CC1)CN(c1ccccc1Nc1cc(-c3ccc(C(F)(F)F)cc3)on1)c1c(O)ccc(Cl)c12]

Example 37A (Z)-3-(2-(4-Chloro-7-methoxy-1'-neopentylspiro[indoline-3,4'-piperidine]-1-yl)phenylamino)-3-(methylthio)-1-(4-(trifluoromethyl)phenyl)prop-2-en-1-one To 1-(4-(trifluoromethyl)phenyl)ethanone (103 mg, 0.548 mmol) in DMF (1 mL) was added sodium hydride (21.9 mg, 0.548 mmol) at 0° C. After 30 min, Example 35A (250 mg, 0.548 mmol) was added. The reaction mixture was stirred at 23° C. overnight. Iodomethane (0.038 mL, 0.60 mmol) was added. The reaction mixture was stirred at 23° C. overnight. The reaction was quenched with water (10 mL) and extracted with EtOAc (5 mL×3). The mixture was concentrated and purified by flash chromatography (silica gel, eluting with EtOAc/Hexanes) to give Example 37A as yellowish oil (333 mg, 0.506 mmol, 92.0% yield). LC-MS ESI 658.3 (M+H) (Method A, RT=3.71 min). $^1$H NMR (400 MHz, DMSO-d$_6$) δ ppm 13.38 (1H, s), 8.09 (2H, d, J=8.24 Hz), 7.80 (2H, d, J=8.25 Hz), 7.43 (1H, d, J=6.05 Hz), 7.12-7.22 (2H, m), 6.96 (1H, d, J=7.70 Hz), 6.75-6.86 (2H, m), 6.06 (1H, s), 3.83 (1H, d, J=9.89 Hz), 3.54 (3H, s), 3.38 (1H, d, J=9.89 Hz), 2.61 (2H, d, J=9.89 Hz), 2.56 (3H, s), 2.31-2.41 (1H, m), 2.02-2.12 (2H, m), 1.98 (1H, s), 1.90 (2H, d, J=19.79 Hz), 1.47 (1H, d, J=12.64 Hz), 1.39 (1H, d, J=12.09 Hz), 0.76 (9H, s).

Example 37B

N-(2-(4-Chloro-7-methoxy-1'-neopentylspiro[indoline-3,4'-piperidine]-1-yl)phenyl)-5-(4-(trifluoromethyl)phenyl)isoxazol-3-amine To Example 37A (329 mg, 0.500 mmol) in ethanol (1 mL) was added hydroxylamine (0.123 mL, 2.00 mmol). The reaction mixture was stirred at 85° C. for 18 h. Quenched the reaction with water (10 mL) and extracted with EtOAc (5 mL×3). Concentrated and purified by flash chromatography (silica gel, eluting with EtOAc/Hexanes) to give Example 37B as yellowish oil (50 mg, 0.080 mmol, 16% yield). LC-MS ESI 625.2 (M+H) (Method A, RT=3.49 min). $^1$H NMR (400 MHz, chloroform-d) δ ppm 7.93 (2H, d, J=8.35 Hz), 7.71 (2H, d, J=7.91 Hz), 7.63 (1H, s), 7.46 (1H, dd, J=8.13, 1.10 Hz), 7.20-7.25 (1H, m), 7.00-7.04 (1H, m), 6.94-6.98 (1H, m), 6.83 (1H, d, J=8.79 Hz), 6.62 (1H, d, J=8.79 Hz), 5.97 (1H, s), 4.01 (1H, d, J=10.11 Hz), 3.45 (3H, s), 3.30 (1H, d, J=10.11 Hz), 2.92 (1H, t, J=12.30 Hz), 2.82 (1H, d, J=9.67 Hz), 2.67-2.77 (2H, m), 2.17 (1H, s), 2.04 (2H, s), 1.55 (2H, t, J=12.30 Hz), 1.26 (2H, s), 0.89 (9H, s).

Example 37

To Example 37B (50 mg, 0.080 mmol) and tetrabutylammonium iodide (177 mg, 0.480 mmol) in dry CH$_2$Cl$_2$ (1 mL) under argon at −50° C., boron trichloride in 1 N dichloromethane solution (0.400 mL, 0.400 mmol) was added dropwise. The stirring mixture was stirred from −50 to −10° C. over 1 h, and then dry ice bath was removed. The mixture was stirred at 23° C. for 18 h. Added boron trichloride in 1N dichloromethane solution (0.400 mL, 0.400 mmol). After 3 h, the reaction was quenched with methanol (2 mL) dropwise, concentrated and purified by Prep HPLC (18-90% MeOH over 30 min, 0.1% TFA as modifier then 18-90% acetonitrile over 10 min, 0.1% TFA as modifier) to give Example 37 as yellow solid (2.00 mg, 3.27 μmol, 4.09% yield). LC-MS ESI 611.2 (M+H) (Method A, RT=3.25 min). $^1$H NMR (400 MHz, methanol-d$_3$) δ ppm 7.93 (2H, d, J=8.25 Hz), 7.76 (2H, d, J=8.79 Hz), 7.48 (1H, d, J=8.24 Hz), 7.16-7.23 (1H, m), 7.01-7.06 (2H, m), 6.71-6.77 (1H, m), 6.66 (1H, t, J=8.52 Hz), 6.04-6.11 (1H, m), 4.16 (1H, d, J=10.44 Hz), 3.98 (1H, s), 3.54-3.65 (2H, m), 3.46 (1H, d, J=10.99 Hz), 3.14-3.19 (1H, m), 3.10 (2H, d, J=10.44 Hz), 2.99 (1H, d, J=2.20 Hz), 2.86 (1H, s), 1.82-1.93 (2H, m), 1.11 (9H, s). Orthogonal HPLC purity: RT=8.89 min, 99% (Method A); RT=7.51 min, 93% (Method B).

Example 38

4-Chloro-1'-neopentyl-1-(2-(5-phenylisoxazol-3-ylamino)phenyl)spiro[indoline-3,4'-piperidin]-7-ol

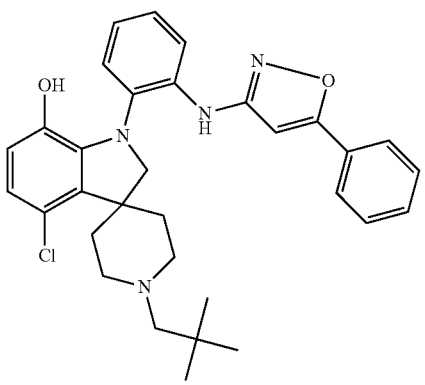 [SMILES: CC(C)(C)CN1CCC2(CC1)CN(c1ccccc1Nc1cc(-c3ccccc3)on1)c1c(O)ccc(Cl)c12]

Example 38 was prepared following the procedure described for Example 37. LC-MS ESI 543.2 (M+H) (Method A, RT=2.94 min). $^1$H NMR (400 MHz, methanol-d$_3$) δ ppm 7.69-7.75 (2H, m), 7.42-7.50 (4H, m), 7.15-7.21 (1H, m), 6.98-7.05 (2H, m), 6.70-6.76 (1H, m), 6.62-6.68 (1H, m), 5.95-6.03 (1H, m), 4.16 (1H, d, J=10.99 Hz), 3.53-3.64 (2H, m), 3.44 (1H, d, J=10.44 Hz), 3.13-3.24 (2H, m), 3.10 (1H, d, J=9.89 Hz), 3.00-3.06 (1H, m), 2.94-3.00 (2H, m), 1.81-1.92 (2H, m), 1.10 (9H, s). Orthogonal HPLC purity: RT=8.33 min, 98% (Method A); RT=6.81 min, 98% (Method B).

Example 39

4-tert-Butyl-2-(2-(4-chloro-7-hydroxy-1'-neopentyl-spiro[indoline-3,4'-piperidine]-1-yl)phenylamino)thiazole-5-carbonitrile

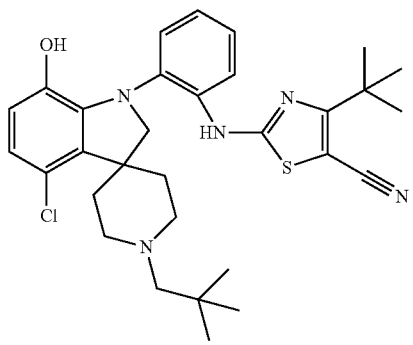 [SMILES: CC(C)(C)CN1CCC2(CC1)CN(c1ccccc1Nc1nc(C(C)(C)C)c(C#N)s1)c1c(O)ccc(Cl)c12]

Example 39A

4-Chloro-7-methoxy-1'-neopentylspiro[indoline-3,4'-piperidine]

At −78° C., to Example 2B (4.41 g, 13.1 mmol) in CH$_2$Cl$_2$ (150 mL) was added bis(2-methoxyethoxy)aluminum(III) sodium hydride (19.6 mL, 65.5 mmol) dropwise, and raised the temperature to rt and stirred for 16 h. The reaction was quenched with water at 0° C. The organic phase was washed with saturated NaHCO$_3$ (30 mL) and extracted with DCM (20 mL), dried over MgSO$_4$, concentrated and purified by flash chromatography with EtOAc/Hexanes to give Example 39A as a white solid (4.10 g, 12.7 mmol, 97.0% yield). LC-MS ESI 323.4 (M+H) (Method B, RT=1.02 min).

Example 39B 1-(2-Bromophenyl)-4-chloro-7-methoxy-1'-neopentylspiro[indoline-3,4'-piperidine]

1,2-Dibromobenzene (1.845 mL, 15.49 mmol), Example 39A (2.00 g, 6.19 mmol), Pd$_2$(dba)$_3$ (0.380 g, 0.415 mmol), rac-BINAP (0.771 g, 1.24 mmol), and Cs$_2$CO$_3$ (4.84 g, 14.87 mmol) were charged into a 20 mL microwave tube and capped with a rubber septa. Toluene (2 mL) was added via syringe. The mixture was degassed twice and recharged with argon. The mixture was stirred in a 110° C. oil bath under argon for 18 h. After cooling, the reaction was filtered and rinsed with EtOAc (2 mL×3) and the filtrate was concentrated. The red crude was purified by flash chromatography (silica gel, eluting with EtOAc/Hexanes) to give a white solid as Example 39B (1.88 g, 3.93 mmol, 63.5% yield). LC-MS ESI 477.1 (M+H), 479.1 (M+2+H) (Method A, RT=2.97 min). $^1$H NMR (400 MHz, chloroform-d) δ ppm 7.57 (1H, d, J=7.91 Hz), 7.17 (1H, t, J=7.03 Hz), 6.95-7.01 (2H, m), 6.78 (1H, d, J=8.35 Hz), 6.63 (1H, d, J=8.79 Hz), 4.20 (1H, d, J=10.55 Hz), 3.50 (3H, s), 3.47 (1H, d, J=10.11 Hz), 2.80 (2H, t, J=10.99 Hz), 2.64-2.74 (2H, m), 2.28-2.37 (1H, m), 2.23 (1H, t, J=11.21 Hz), 1.99-2.09 (2H, m), 1.59 (1H, d, J=11.86 Hz), 1.41 (1H, d, J=12.30 Hz), 0.89 (9H, s).

Example 39C 4-tert-Butyl-2-(2-(4-chloro-7-methoxy-1'-neopentyl-spiro[indoline-3,4'-piperidine]-1-yl)phenylamino)thiazole-5-carbonitrile A mixture of Example 39B (100 mg, 0.209 mmol), 2-amino-4-tert-butylthiazole-5-carbonitrile (76 mg, 0.419 mmol), $Pd_2(dba)_3$ (38.3 mg, 0.042 mmol), xanthphos (36.3 mg, 0.063 mmol), and sodium carbonate (31.1 mg, 0.293 mmol) in toluene (0.8 mL) was degassed twice under argon. The reaction mixture then was refluxed at 110° C. for 18 h, filtered and rinsed with dichloromethane (2 mL×2). The filtrate was concentrated and purified by flash chromatography (silica gel, eluting with EtOAc/Hexanes) to give Example 39C as yellow oil (53 mg, 0.092 mmol, 44% yield). LC-MS ESI 578.2 (M+H) (Method A, RT=3.49 min).

Example 39

To Example 39C (43 mg, 0.075 mmol) and tetrabutylammonium iodide (165 mg, 0.447 mmol) in dry $CH_2Cl_2$ (1 mL) under argon at −50° C., boron trichloride in 1 N dichloromethane solution (0.373 mL, 0.373 mmol) was added dropwise. The stirring mixture was stirred from −50 to −10° C. over 1 h, and then dry ice bath was removed. The mixture was stirred at 23° C. for 18 h. MeOH (5 mL) was added dropwise. The crude was concentrated and purified by Prep HPLC (9-90% MeOH over 30 min, 0.1% TFA as modifier then 9-81% acetonitrile over 15 min, 0.1% TFA as modifier) to give Example 39 as a white solid (3 mg, 5 μmol, 7% yield). LC-MS ESI 477.1 (M+H), 479.1 (M+2+H) (Method A, RT=2.97 min). $^1$H NMR (400 MHz, methanol-$d_3$) δ ppm 8.18 (1H, d, J=8.35 Hz), 7.17 (1H, ddd, J=8.24, 4.61, 4.28 Hz), 7.02 (2H, t, J=4.61 Hz), 6.72-6.78 (1H, m), 6.61-6.65 (1H, m), 4.16 (1H, d, J=10.99 Hz), 3.42-3.48 (1H, m), 3.21 (2H, t, J=12.52 Hz), 3.11 (2H, d, J=9.67 Hz), 3.01 (2H, d, J=3.95 Hz), 1.93-2.02 (1H, m), 1.84 (1H, s), 1.46 (9H, s), 1.12 (9H, s). Orthogonal HPLC purity: RT=8.74 min, 99% (Method A); RT=7.28 min, 99% (Method B).

Examples 40-42 were prepared following the procedure described for Example 39.

Example 40

Ethyl 2-(2-(4-chloro-7-hydroxy-1'-neopentylspiro[indoline-3,4'-piperidine]-1-yl)phenylamino)-4-(trifluoromethyl)thiazole-5-carboxylate

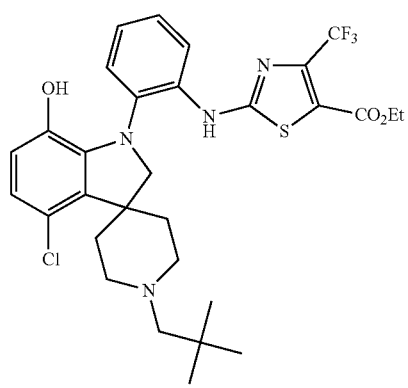 [SMILES: CCOC(=O)c1sc(Nc2ccccc2N2CC3(CCN(CC(C)(C)C)CC3)c3c(Cl)ccc(O)c32)nc1C(F)(F)F]

LC-MS ESI 623.4 (M+H) (Method A, RT=3.10 min). $^1$H NMR (400 MHz, methanol-$d_3$) δ ppm 7.92-8.03 (1H, m), 7.19 (1H, t, J=6.60 Hz), 7.01-7.11 (2H, m), 6.71-6.81 (1H, m), 6.60-6.68 (1H, m), 4.29 (2H, q, J=7.15 Hz), 4.13 (1H, d, J=10.99 Hz), 3.55-3.66 (2H, m), 3.44-3.52 (1H, m), 3.12-3.23 (2H, m), 2.99-3.11 (4H, m), 1.92-1.98 (1H, m), 1.80-1.89 (1H, m), 1.31 (3H, t, J=7.15 Hz), 1.12 (9H, s). Orthogonal HPLC purity: RT=8.61 min, 92% (Method A); RT=7.18 min, 94% (Method B).

Example 41

4-Chloro-1-(2-(5-isobutyl-4,5,6,7-tetrahydrothiazolo[5,4-c]pyridin-2-ylamino)phenyl)-1'-neopentylspiro[indoline-3,4'-piperidin]-7-ol

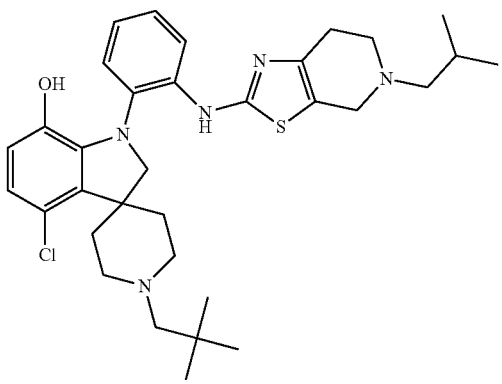 [SMILES: CC(C)CN1CCc2nc(Nc3ccccc3N3CC4(CCN(CC(C)(C)C)CC4)c4c(Cl)ccc(O)c43)sc2C1]

LC-MS ESI 594.2 (M+H) (Method A, RT=2.25 min). $^1$H NMR (400 MHz, methanol-$d_3$) δ ppm 7.78-7.88 (1H, m), 7.14-7.21 (1H, m), 6.98-7.08 (2H, m), 6.70-6.79 (1H, m), 6.59-6.66 (1H, m), 4.54 (2H, s), 4.25 (2H, s), 4.10 (1H, d, J=10.44 Hz), 3.80 (2H, s), 3.64 (2H, d), 3.58 (1H, d, J=10.44 Hz), 3.48 (2H, d, J=9.89 Hz), 3.15 (2H, d, J=7.15 Hz), 3.00-3.09 (2H, m), 2.16-2.27 (2H, m), 1.93 (1H, m), 1.85 (2H, d, J=13.74 Hz), 1.13 (9H, s), 1.07 (6H, d, J=6.60 Hz). Orthogonal HPLC purity: RT=6.13 min, 96% (Method A); RT=4.61 min, 95% (Method B).

Example 42

4-Chloro-1'-neopentyl-1-(2-(5-(trifluoromethyl)pyridin-2-ylamino)phenyl)spiro[indoline-3,4'-piperidin]-7-ol

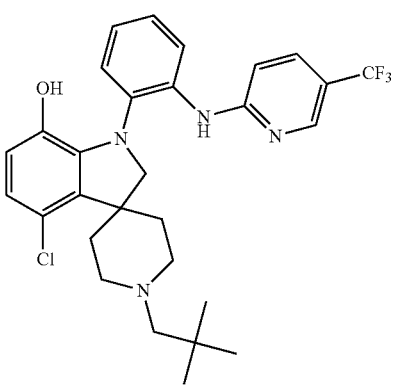 [SMILES: CC(C)(C)CN1CCC2(CC1)CN(c1ccccc1Nc1ccc(C(F)(F)F)cn1)c1c(O)ccc(Cl)c12]

LC-MS ESI 545.1 (M+H) (Method A, RT=2.75 min). $^1$H NMR (400 MHz, methanol-$d_3$) δ ppm 8.16 (1H, d, J=5.71 Hz), 7.46-7.52 (1H, m), 7.17-7.24 (3H, m), 6.98-7.06 (2H, m), 6.63-6.74 (2H, m), 3.89-3.95 (1H, m), 3.52-3.60 (2H, m), 3.25 (1H, s), 3.04-3.14 (2H, m), 2.93-3.02 (4H, m), 1.76 (1H, d, J=14.50 Hz), 1.51 (1H, d, J=12.30 Hz), 1.11 (9H, s). Orthogonal HPLC purity: RT=7.34 min, 100% (Method A); RT=6.09 min, 99% (Method B).

Example 43

Methyl 7-hydroxy-1'-neopentyl-1-(2-(5-(4-(trifluoromethyl)phenyl)-1,3,4-thiadiazol-2-ylamino)phenyl)spiro[indoline-3,4'-piperidine]-4-carboxylate To Example 3 (7.0 mg, 11 μmol) was added to 1 N NaOH (1 mL, 1 mmol) at rt. MeOH (0.3 mL, 7 mmol) was added to the suspension and the reaction mixture became clear. The mixture was stirred at 40° C. in a capped vial for 1 day. After cooling, 1 N HCl was added to neutralize the reaction. It was extracted with CH$_2$Cl$_2$ (2×). The residue was dissolved in CH$_3$CN and was purified by RPHPLC with CH$_3$CN/H$_2$O/ 0.1% TFA to give pure Example 43 (5.10 mg, 7.83 μmol, 74.0% yield). LC-MS ESI 652.7 (M+H) (Method A, RT=3.35 min).

Example 44

Methyl 1-(2-(5-(4-tert-butylphenyl)-1,3,4-thiadiazol-2-ylamino)phenyl)-7-hydroxy-1'-neopentylspiro[indoline-3,4'-piperidine]-4-carboxylate

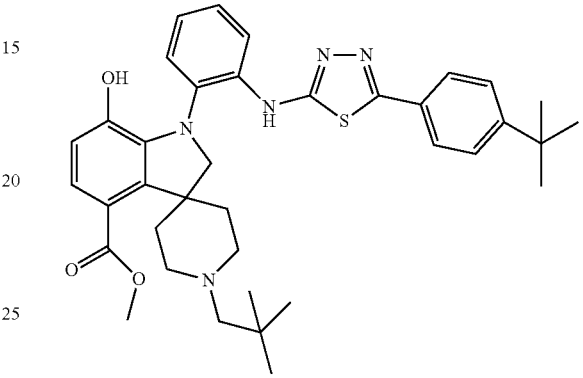

Example 44 (29.0% yield) was obtained by following the same procedure as example 43 using Example 2 as the starting material. LC-MS ESI 640.7 (M+H) (Method B, RT=1.90 min).

Example 45

7-Hydroxy-1'-neopentyl-1-(2-(5-(4-(trifluoromethyl)phenyl)-1,3,4-thiadiazol-2-ylamino)phenyl)spiro[indoline-3,4'-piperidine]-4-carbonitrile

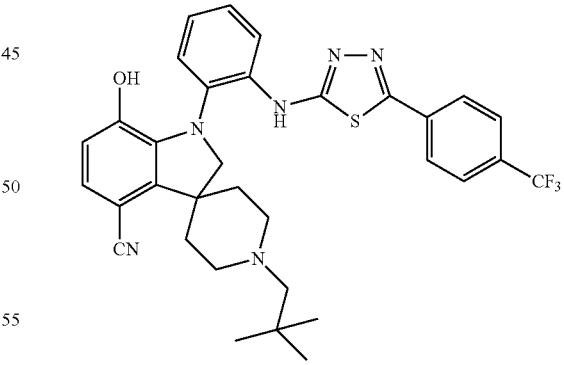

To Example 3 (6 mg, 9 μmol) was added to 1 N NaOH (1 mL, 1 mmol) at rt. Ammonium hydroxide (0.50 mL, 13 mmol) was added to the suspension and the reaction mixture became clear. The mixture was stirred at 25° C. in a capped vial for 2 days. After cooling, 1 N HCl was added to neutralize the reaction. It was extracted with CH$_2$Cl$_2$ (2×), washed with H$_2$O, brine, dried over MgSO$_4$, filtered and concentrated. The residue was dissolved in CH$_3$CN and was purified by RPHPLC with CH$_3$CN/H$_2$O/0.1% TFA to give Example 45

(4.3 mg, 7.0 µmol, 77% yield). LC-MS ESI 619.6 (M+H) (Method A, RT=3.14 min). $^{19}$F NMR (376.5 MHz, acetone) δ ppm −63.22.

Example 46

1-(2-(5-(4-tert-Butylphenyl)-1,3,4-thiadiazol-2-ylamino)phenyl)-7-hydroxy-1'-neopentylspiro[indoline-3,4'-piperidine]-4-carbonitrile

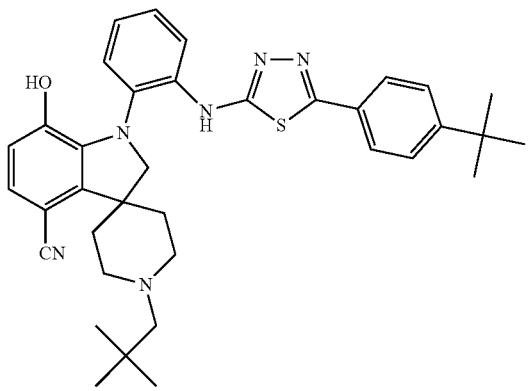 [SMILES: CC(C)(C)CN1CCC2(CC1)CN(c1ccccc1Nc1nnc(-c3ccc(C(C)(C)C)cc3)s1)c1c(O)ccc(C#N)c12]

Example 46 (76% yield) was obtained by following the same procedure as example 45 using Example 2 as starting material. LC-MS ESI 607.7 (M+H) (Method B, RT=1.82 min).

What is claimed is:
1. A compound of Formula (I):

(I)

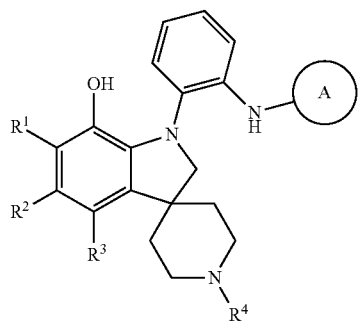

or a stereoisomer, a tautomer, or a pharmaceutically acceptable salt thereof, wherein:
ring A is independently selected from

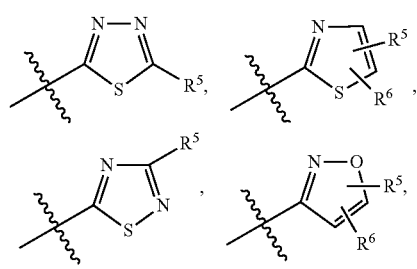

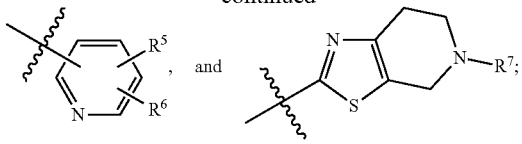

and
$R^1$ is independently selected from H, halogen and OH;
$R^2$ is independently H or halogen;
$R^3$ is independently selected from H, halogen, $C_{1-6}$ haloalkyl, CN and $CO_2(C_{1-4}$ alkyl);
$R^4$ is independently $C_{2-6}$ alkyl substituted with 0-3 F atoms;
$R^5$ is, independently at each occurrence, selected from $C_{1-6}$ alkyl, $C_{1-6}$ alkenyl, $CO_2(C_{1-4}$ alkyl), phenyl, pyridyl, benzyl, pyrazolyl, N—($C_{1-4}$ alkyl)-pyrazolyl, pyrazinyl, quinoxalinyl, and

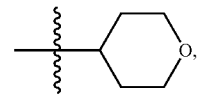 [SMILES: *C1CCOCC1]

wherein each ring moiety is substituted with zero to three substituents independently selected from the group consisting of: halogen, $C_{1-6}$ alkyl, $C_{1-6}$ haloalkyl, $C_{1-6}$ haloalkoxy, and $N(C_{1-4}$ alkyl)$_2$;
$R^6$ is, independently at each occurrence, selected from H, $C_{1-6}$ alkyl,
$C_{1-6}$ haloalkyl, CN and $CO_2(C_{1-4}$ alkyl); and
$R^7$ is independently $C_{1-6}$ alkyl.

2. A compound according to claim 1, wherein the compound is of Formula (II):

(II)

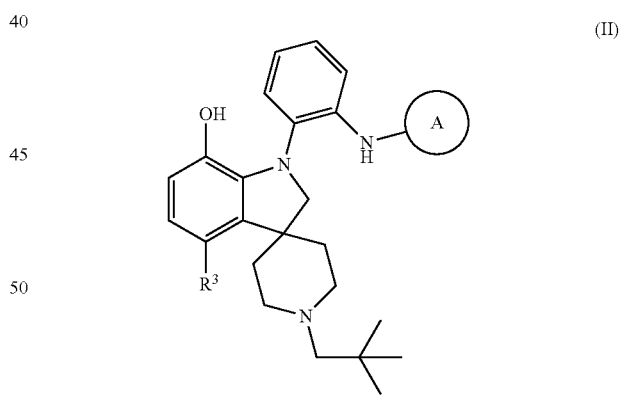

or a stereoisomer, a tautomer, or a pharmaceutically acceptable salt thereof.

3. A compound according to claim 1, wherein:
ring A is independently selected from

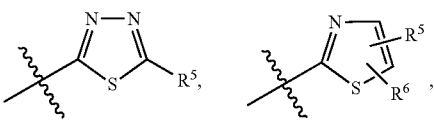

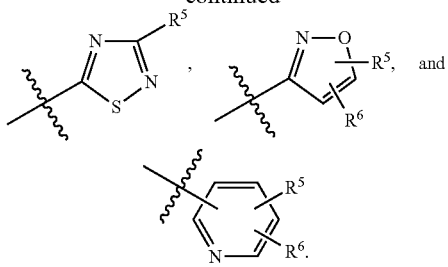

4. A compound according to claim 1, wherein: ring A is independently selected from

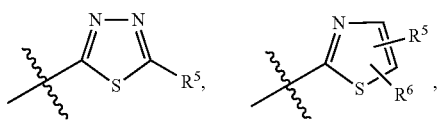

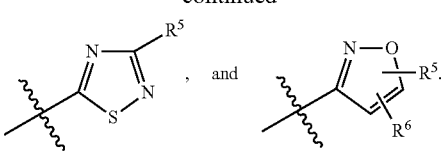

5. A compound according to claim 1, wherein the compound is selected from the exemplified examples or a stereoisomer, a tautomer, or a pharmaceutically acceptable salt thereof.

6. A pharmaceutical composition, comprising: a pharmaceutically acceptable carrier and a compound of claim 1, or a stereoisomer, a tautomer, or a pharmaceutically acceptable salt thereof.

* * * * *